United States Patent
Gabriel et al.

(10) Patent No.: US 9,181,310 B2
(45) Date of Patent: *Nov. 10, 2015

(54) USE OF BACTERIOPHAGE OUTER MEMBRANE BREACHING PROTEINS EXPRESSED IN PLANTS FOR THE CONTROL OF GRAM-NEGATIVE BACTERIA

(71) Applicants: Integrated Plant Genetics, Inc., Alachua, FL (US); University of Florida Research Foundation, Inc., Gainesville, FL (US)

(72) Inventors: Dean W. Gabriel, Alachua, FL (US); Yingnan Jiang, Alachua, FL (US)

(73) Assignees: University of Florida Research Foundation, Inc., Gainesville, FL (US); Integrated Plant Genetics, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/801,088

(22) Filed: Mar. 13, 2013

(65) Prior Publication Data

US 2015/0252380 A1    Sep. 10, 2015

Related U.S. Application Data

(63) Continuation-in-part of application No. 13/487,595, filed on Jun. 4, 2012, now Pat. No. 8,507,650, which is a continuation-in-part of application No. 12/176,874, filed on Jul. 21, 2008, now Pat. No. 8,212,110, which is a continuation-in-part of application No. 10/556,563, filed as application No. PCT/US2004/015099 on May 14, 2004, now Pat. No. 7,919,601.

(60) Provisional application No. 60/470,799, filed on May 14, 2003, provisional application No. 60/950,749, filed on Jul. 19, 2007.

(51) Int. Cl.
  *C12N 15/82* (2006.01)
  *C07K 14/415* (2006.01)
  *C07K 14/005* (2006.01)

(52) U.S. Cl.
  CPC ............. *C07K 14/415* (2013.01); *C07K 14/005* (2013.01); *C12N 15/8281* (2013.01)

(58) Field of Classification Search
  USPC .................................................. 800/288, 279
  See application file for complete search history.

(56) References Cited

U.S. PATENT DOCUMENTS

| | | |
|---|---|---|
| 6,783,930 B1 | 8/2004 | Pelletier et al. |
| 6,858,707 B1 | 2/2005 | Wei et al. |
| 7,919,601 B2 | 4/2011 | Ramadugu et al. |
| 8,212,110 B2 | 7/2012 | Gabriel et al. |
| 2009/0036307 A1 | 2/2009 | Gabriel et al. |
| 2009/0136914 A1 | 5/2009 | Ramadugu et al. |
| 2012/0316104 A1 | 12/2012 | Gabriel et al. |

FOREIGN PATENT DOCUMENTS

WO   WO 2004/104169 A2   12/2004

OTHER PUBLICATIONS

Guo et al. PNAS, 101: 9205-9210 (2004).*
Keskin et al. Protein Science, 13:1043-1055, (2004).*
English translation of Office Action in Chinese Patent Application No. 200880107780.2, mailed on Nov. 30, 2012.
Fourgoux-Nicol et al. "Isolation of rapeseed genes expressed early and specifically during development of the male gametophyte", (1999) Plant Molecular Biology 40:857-872.
Grundling et al., "Dimerization between the Holin and Holin Inhibitor of Phage λ," J. Virol. 182(21):6075-6081 (2000).
Guo et al. "Protein tolerance to random amino acid change", PNAS (2004), 101:9205-9210.
Keshin et al. "A new, structurally nonredundant, diverse data set of protein-protein interaces and its implications", Protein Science (2004), 13:1043-1056.
Masaya Oki, et al., "Functional and structural features of the holing HOL protein of the *Lactobacillus plantarum* phage Φgle: analysis in *Escherichia coli* system", GENE 197 (1997) pp. 137-145.
Pompejus et al., Genbank Accession No. AAB79429 (2001).
The Written Opinion of the International Searching Authority based on International Application PCT/US2008/070612 (Nov. 10, 2008).

* cited by examiner

*Primary Examiner* — Medina A Ibrahim
(74) *Attorney, Agent, or Firm* — Cooley LLP

(57) ABSTRACT

The present invention provides compositions and methods for killing or suppressing growth of Gram-negative bacteria that infect, infest or cause disease in plants, including pathogenic, saprophytic and opportunistic microbes that cause disease in plants and food borne illness in people or in animal feed.

16 Claims, 14 Drawing Sheets

USE OF BACTERIOPHAGE OUTER MEMBRANE BREACHING PROTEINS EXPRESSED IN PLANTS FOR THE CONTROL OF GRAM-NEGATIVE BACTERIA

CROSS-REFERENCE TO RELATED APPLICATIONS

This application is a Continuation-In-Part of U.S. application Ser. No. 13/487,595, filed Jun. 4, 2012, now issued as U.S. Pat. No. 8,507,605, which is a Divisional of U.S. application Ser. No. 12/176,874, filed Jul. 21, 2008, now as U.S. Pat. No. 8,212,110, which is a Continuation-In-Part of U.S. application Ser. No. 10/556,563, filed Nov. 14, 2005, now issued as U.S. Pat. No. 7,919,601, which claims benefit as a U.S. National Stage Application under 35 U.S.C. 371 of PCT/US2004/015099, filed May 14, 200.4, which claims the benefit of U.S. Provisional Application Ser. No. 60/470,799, filed May 14, 2003, each of which are herein incorporated by reference in their entireties for all purposes. U.S. application Ser. No. 12/176,874 also claims the benefit of U.S. Provisional Application No. 60/950,749, filed Jul. 19, 2007, which is herein incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename INTE_004_03US_SeqList_ST25.txt, date recorded: May 30, 2013, file size 35 kilobytes.)

FIELD OF THE INVENTION

The present invention relates to methods for killing or suppressing growth of Gram-negative bacteria that infect, infest or cause disease in plants, including pathogenic, saprophytic and opportunistic microbes that cause disease in plants and food borne illness in people or in animal feed.

BACKGROUND OF THE INVENTION

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Plants grown for commercial agricultural purposes are nearly always planted as uniform monocultures; that is, single varieties of a given crop are mass-produced by vegetative propagation or by seed and are planted on a very large scale. When a pathogen or pest arrives that can overcome the natural disease or pest resistance of a given variety, severe economic losses can occur because of the practice of monoculture, sometimes involving loss of the entire crop in a given area. Control of diseases and pests using massive applications of agricultural chemicals is expensive, environmentally unsound and often impossible. For example, citrus canker disease, caused by a quarantined Gram-negative bacterial pathogen, *Xanthomonas citri*, has spread uncontrollably throughout Florida. As a second example, the Gram-negative bacterial pathogen Ca. Liberibacter *asiaticus* was a USDA Select Agent (potential bioterrorist agent-until it was introduced into Florida in 2005 and spread uncontrollably throughout Florida. This pathogen threatens world citrus production. As a third example, the Gram-negative bacterial pathogen *Ralstonia solanacearum* Race 3 Biovar 2 has been introduced into the U.S. numerous times and is such a serious threat to U.S. potato production that it is also a listed USDA Select Agent. This pathogen has been introduced into the U.S. by infecting geranium plants, but asymptomatically, so that detection of the pathogen is delayed.

As a fourth and final example, serious human illness and even deaths have been reported due to the Gram-negative bacterium *Escherichia coli*, which is capable of internally infecting—not just contaminating—certain crop plants such as spinach, alfalfa sprouts and mung bean sprouts. Several outbreaks of *Salmonella* and *E. coli* O157:H7 associated with organically grown sprouts and mesclun lettuce have been reported (Doyle, M. P. 2000. Nutrition 16: 647-9). According to the FDA in its web report of the 2006 outbreak of *E. coli* in contaminated spinach "To date, 204 cases of illness due to *E. coli* O157+17 infection have been reported to the CDC including 31 cases involving a type of kidney failure called Hemolytic Uremic Syndrome (HUS), 104 hospitalizations, and three deaths. The first death was an elderly woman in Wisconsin; the second death, a two-year-old in Idaho; and the third death, an elderly woman in Nebraska." Conventional plant breeding to control such diseases of plants or food-borne contamination has proven to be impossible. There is therefore an urgent and pressing need for gene engineering techniques to provide plants, including carrier plants such as geraniums, with disease and pest resistance against diseases and pests that they naturally are susceptible to, or tolerant of.

A wide variety of antibacterial and antifungal proteins have been identified and their genes isolated from both animals and plants. Because of the major differences in the structures of fungal, Gram-positive bacterial and Gram-negative bacterial cell walls, many of these proteins attack only fungi or Gram positive bacteria, which have cell walls that are exposed directly to the environment. Gram-negative bacteria do not have cell walls that are exposed directly to the environment. Instead, their cell walls are enveloped and protected by a unique outer membrane structure, the lipopolysaccharide (LPS) barrier, which provides a very effective additional barrier to protect their cell walls against most eukaryotic defenses, particularly plant defenses. Mutations affecting the LPS of several Gram negative bacterial plant pathogens have been shown to compromise the critically important barrier function of OMs and allow detergents, salts, toxic chemicals and host defense compounds, including phytoalexins and/or reactive oxygen species, to be much more effective—typically effective at 5-fold to 100-fold lower concentrations—against bacteria suffering these mutations (Kingsley et al., 1993, Balsanelli et al. 2010). The LPS typically consist of a hydrophobic domain known as lipid A (or endotoxin), which anchors the LPS to the outer membrane. Covalently attached to lipid A is a nonrepeating "core" oligosaccharide, which is in turn covalently attached to the repeating distal polysaccharide (or O-antigen), which can be quite lengthy, and which extends outwards from the bacterium. The composition of the polysaccharide side chains varies greatly between bacteria, and some bacteria modify the composition of these chains during stress. The great majority of the pathogens listed by the USDA as Select Agents are bacterial plant pathogens, and all of these are Gram negative. Indeed, the great majority of bacterial plant pathogens are Gram negative.

The LPS also provides an effective defense to Gram-negative bacteria against externally produced enzymes that can effectively degrade the bacterial cell wall (also called the murein layer), including the relatively thick but exposed cell walls of Gram-positive bacteria and fungi. For example, lysozymes are antimicrobial agents found in mammalian cells, insects, plants, bacteria and viruses that break bacterial and fungal cell walls, specifically cleaving bonds between the amino sugars of the recurring muropeptides (C-1 of N-acetylmuramic acid and C-4 of N-acetylglucosamine of microbial cell walls (Ibrahim et al. 2001 and references therein). Some lysozymes also are pleiotropically lytic proteins, meaning they are active in killing Gram-negative and Gram-positive bacteria, but this activity is not due to the enzymatic action of lysozyme, but specifically due to a short, linear peptide fragment that is a degradation product of some lysozymes; it is the linear degradation product of the lysozyme that penetrates the LPS barrier and the cell wall (but without harming either), reaching the inner membrane and permeabilizing the inner membrane, resulting in lysis (During et al, 1999; Ibrahim et al. 2001). However, this linear peptide activity does not work well in plants (see below).

Proteins fold to form complex, irregular three dimensional structures that are often lacking symmetry; to date, the three dimensional structure cannot typically be predicted from the amino acid sequence. However, there are certain local regions of sequence that form secondary structures that can be predicted, and identical secondary structures can reliably be formed using conservatively substituted amino acids.

Proteins are an amazing means for translating linear coded information (i.e., DNA sequence) into biological function. However, the primary (linear) protein sequence does not readily reveal which parts of the protein are important for function (enzymatic activities or nonenzymatic activities such as antibody binding sites), which parts are important for conserved structural functions (such as anchoring to membranes, cell walls, outer membranes or organelles) and which parts are merely occupying space as fillers. Critical functional domains often involve two relatively distant portions of the linear protein being brought into close proximity by folding, often assisted by the action of other proteins, into an active, three dimensional (tertiary) structure.

It has long been known that many proteins have a modular structure (Moore, I., et al. 1998, and references therein). By modular structure is meant that one portion or region, usually termed a "domain" of the protein may serve a structural purpose, such as a membrane anchor, say, and another domain of the protein may be enzymatic or possess a unique nonenzymatic function. Domains are the structural subunits that come together to form the functional parts of a protein. Long polypeptides will fold into compact, semi-independent, structural domain units. Domains with identical function, say as a membrane anchor, can be present in multiple proteins, and all be of very different sequence. Globular domains are structurally compact, typically with a hydrophobic core, and have more interactions among the amino acids within the domain than with the rest of the protein (Janin and Wodak, 1983). Globular domains can be identified by computer programs that calculate several characteristics, particularly localized compactness or globularity and extent of isolation (Taylor, 1999). Some structural features, such as secretion signal sequences and transmembrane domains, are readily interchangeable with other such domains from different proteins, despite being of completely different primary amino acid sequence and the gene region encoding the domain being of completely different DNA coding sequence. The term "transmembrane domain" typically denotes a single transmembrane alpha helix of a transmembrane protein. The alpha-helical domains of transmembrane proteins are found in all types of biological membranes, including outer membranes.

However, the transmembrane domains of proteins found in the outer membranes of Gram-negative bacteria can also be comprised of a completely different structure, called a beta strand, which typically consists of a membrane-spanning stretch of 5-10 amino acids in length, whose peptide backbones are almost fully extended with the sidechains of two neighboring residues projected in the opposite direction from the backbone. Two or more hydrogen bonded (parallel or anti-parallel) beta strands form a beta sheet. A linker is a peptide sequence composed of flexible amino acids residues like glycine and serine such that the adjacent protein domains are free to move relative to one another to ensure that two adjacent domains do not sterically interfere with one another. Linkers must be flexible, keeping individual beta strands domains apart, while allowing them to move in order to form a parallel or anti-parallel beta sheet. A beta barrel is formed by a beta sheet that encloses a central pore. Beta barrels consist usually of an even number of beta strands (between 8 and 24).

The beta-barrel domains of transmembrane proteins are distinctive in that they are found only in the outer membranes of Gram-negative bacteria, the lipid-rich cell walls of a few Gram-positive bacteria (the outermost portion of the Gram-positive bacterial cell), and the outer membranes of mitochondria and chloroplasts. Beta barrels are typically comprised of antiparallel beta strands, which typically contain alternating polar and hydrophobic amino acids. When a protein is predicted to form a beta barrel, that protein is likely targeted to the bacterial outer membrane.

Computer software can be used to identify secondary structural (domain) elements such as amphipathic alpha helices and beta strands within the structure of a protein and then to design or utilize pre-existing similar domains to swap with a natural domain module and still retain overall protein function. These secondary structural domain elements are identified not only by primary amino acid sequence (methionine, alanine, leucine, glutamate and lysine all have especially high alpha helix-forming propensities, whereas proline, glycine and aspartic acid all have poor helix-forming propensities (Pace and Scholz, 1998), but also by rules which require amino acids with certain properties (say hydrophobic) be in certain positions, and other amino acids with different properties (say hydrophilic) be in other positions. In these transmembrane domains, it is unimportant as to which specific hydrophobic or hydrophilic amino acid actually occupies a particular position, and one can readily predict which amino acids would likely serve as conservative substitutes for another in such a physical structures. For example, in an amphipathic alpha helix, one side of the helix contains mainly hydrophilic amino acids and the other side contains mainly hydrophobic amino acids. The amino acid sequence of amphipathic alpha helix alternates between hydrophilic and hydrophobic residues every 3 to 4 residues, since the a helix makes a turn for every 3.6 residues.

Similarly, a beta strand is a stretch of ca. 5-10 amino acids (most likely are A, Ala; R, Arg; C, Cys; Q, Gln; H, His; I, Ile; L, Leu; M, Met; F, Phe; T, Thr; W, Trp; Y, Tyr; V, Val (Lifson and Sander, 1979), with a peptide backbone that is almost fully extended and stabilized by hydrogen bonds with another beta strand that is arranged parallel or anti-parallel to the first strand. The aromatic amino acids W, Trp; Y, Tyr and F, Phe usually demarcate the interfacial boundaries between the hydrophobic and aqueous domains on both sides of the outer membrane (Schultz, 2002). In many cases the strands contain alternating polar and hydrophobic amino acids. Residues pointing inwards in the barrel can also be non-polar (Schulz, 2000). As with alpha helices, it is (and has been since 1992) relatively easy to one skilled in the art to access publically available software to identify predicted beta strands (for example, PredictProtein; Rost & Liu, 2003).

Outer membrane proteins carry secondary structural regions that form beta strands that are used to either anchor an enzymatically active portion of the molecule on one side or another of the outer membrane, or to form a pore-like barrel structure. Computer software such as PRED-TMBB (Bagos, 2004) can be used to predict transmembrane beta strand domains that are likely to be localized to the bacterial outer membrane. As with the alpha helix, it is usually unimportant as to which specific hydrophobic or hydrophilic amino acid actually occupies a particular position, and we can readily predict which amino acids would likely serve as conservative substitutes for another in such a physical secondary structure domain. Designing or utilizing pre-existing similar domain module and using them to swap with a natural domain module and still retain overall protein function is readily accomplished by the simple expedient of ordering the gene encoding the substituted protein synthesized from a commercial vendor Those antimicrobial proteins demonstrated to kill Gram-negative bacteria, called "lytic peptides", are mostly small peptides (proteins of less than 50 amino acids in length) that target the bacterial inner membrane. These proteins are amphipathic and positively charged, so that they are attracted to the negatively charged Gram-negative outer membrane, are small enough to penetrate both the outer membrane and the relatively thin Gram-negative cell wall, where they then contact and act to permeabilize the inner membrane, directly causing cell death. During the last two decades, over 500 lytic peptides have been discovered in viruses, insects, plants and animals (Jaynes et al, 1987; Mitra and Zhang, 1994; Broekaert et al. 1997; Nakajima et al, 1997; Vunnam et al, 1997). The best described of these are peptides having broad spectrum activity in the source organism and in artificial media against viruses, bacteria, fungi, parasites and even tumor cells (Hancock and Lehrer, 1998).

The largest described group by far of these lytic peptides is linear in structure (eg., cecropins, attacins and magainins). However, linear peptides are not found naturally in plants and most linear peptides are rapidly degraded by plant proteases. For example, cecropin B is rapidly degraded when incubated with intercellular plant fluid, with a half-life ranging from about three minutes in potato to about 25 hours in rice (Owens & Heutte, 1997). Transgenic tobacco plants expressing cecropins have only slightly increased resistance to (Gram-negative) *Pseudomanas syringae* pv. *tabaci*, the cause of tobacco wildfire (Huang et al 1997). Synthetic cecropin analogs Shiva-1 and SB-37, expressed from transgenes in potato plants, only slightly reduced bacterial infection caused by (Gram-negative) *Erwinia carotovora* (Arce et al 1999). Transgenic apple expressing the SB-37 peptide showed only slightly increased resistance to (Gram-negative) *E. amylovora* in field tests (Norelli et al 1998). Similarly, transgenic potatoes expressing attacin showed resistance to bacterial infection by *E. carotovora* (Arce et al 1999) and transgenic pear and apple expressing attacin genes have also shown slightly enhanced resistance to *E. amylovora* (Norelli et al 1994; Reynoird et al 1999). Attacin E was also found to be rapidly degraded by plants (Ko et al 2000). Transgenic tobacco plants expressing a synthetic magainin analog that had been modified to be less sensitive to extracellular plant proteases were only slightly resistant to the bacterial pathogen *E. carotovora* (Li et al 2001).

The disulfide-linked lytic peptides (e.g. defensins, prophenins and thaumatins) show more promise of stability when expressed in plants, but resistance has either been weak, not demonstrated, or cytotoxicity issues have emerged. Hen egg-white lysozyme genes (with lytic ability) have been used to confer weak Gram-negative bacterial disease resistance to transgenic tobacco plants (Trudel et al 1995; Kato et al 1998). Bacteriophage T4 lysozyme has also been reported to slightly enhance resistance in transgenic potato against *E. carotovora* (During et al 1993; Ahrenholz et al., 2000) and in transgenic apple plants against *E. amylovora* (Ko 1999). However, as mentioned previously, the action of lysozyme against Gram-negative bacteria is specifically due to a short lytic peptide fragment (Ibrahim et al. 2001) that is presumably sensitive to protease. Thaumatins exhibit the widest range of antimicrobial activity so far characterized, but also exhibit potent cytotoxic effects on eukaryotic cells (Taguchi et al 2000). Defensins, produced by plants, mammals and insects, are characterized by complex $\beta$-sheet structures with several disulfide bonds that bind and disrupt microbial plasma membranes. A plant defensin from alfalfa gave robust resistance to a fungal pathogen (Guo et al 2000) and defensins from spinach were active in vitro against Gram positive and Gram-negative bacteria (Segura et al. 1998). However, human illnesses have resulted from both alfalfa and spinach infected with enteric bacteria; evidently these defensins are either not triggered by these bacteria or they are ineffective against these bacteria. More effective antibacterial agents are urgently needed to protect crop plants.

Lytic peptides are abundant in nature but of limited value in transgenic plants, primarily due to degradation by plant proteases. In addition, some Gram-negative bacteria are resistant to antimicrobial peptides even in culture media, due to variations in the chemical structure of the LPS (Gutsmann et al., 2005). This may help explain why plant pathogenic bacteria can overcome host plant defensins. To date, no lytic peptide has proved more than marginally effective against Gram-negative bacteria when expressed in plants. More efficacious methods to control plant disease are urgently needed.

By contrast with bacterial pathogens of animals, the vast majority of bacterial pathogens of plants are Gram-negative. As mentioned above, the distinguishing feature of Gram-negative bacteria is the presence of the LPS, which forms an outer membrane that completely surrounds the cell wall. Mutations affecting the structure of the LPS of a (Gram-negative) bacterial plant pathogen of citrus caused the pathogen to die out very quickly on citrus, but not on bean (Kingsley et al., 1993), indicating the importance of the LPS structure in evading specific plant phytochemical defenses. In addition, mutations affecting multidrug efflux in Gram-negative bacteria cause the bacteria to die out rapidly in plants, highlighting the role of low molecular weight plant defense compounds (phytoalexins) in plant defense, and further indicating the importance of the intact LPS of Gram-negative in resisting plant defense compounds (Reddy et al., 2007). Multidrug efflux requires an intact LPS for function.

Animals have a unique set of innate defenses against microbial invasion that is independent of prior exposure to pathogens (Hoffman et al., 1999). Among these are the lytic peptides discussed above, and also the neutrophil, a white blood cell that is part of the innate immune system. Neutrophils produce a variety of protein and peptide antibiotics that kill microorganisms. Among these is the bactericidal/permeability increasing (BPI) protein, which is a potent antimicrobial protein that is primarily active towards Gram-negative bacteria (Levy, 2000). BPI is not toxic to Gram positive bacteria, fungi or animal cells, but rather attacks the LPS layer of Gram-negative cells, disrupting its structure, and eventually attacking the inner membrane and causing lysis (Mannion et al., 1990). A hallmark of BPI proteins is their strongly cationic, lysine rich nature and their opsonic or immune system activation ability (Levy et al., 2003). Members of the BPI protein family include lipopolysaccharide binding protein (LBP), lung specific X protein (LUNX), palate, lung and nasal epithelial clone (PLUNC) and parotid secretory protein (PSP), many of which have been identified by bioinformatics techniques with up to 43% identity between family members (Wheeler et al. 2003). There are numerous patents covering use of BPI and certain smaller peptide derivatives (for example, U.S. Pat. No. 5,830,860 and U.S. Pat. No. 5,948,408).

Antimicrobial bacteriophage proteins.

All bacteriophages must escape from bacterial host cells, either by extrusion from the host cell, as with filamentous phages, or by host cell lysis from within. Host cell lysis from within requires two events: ability to penetrate the inner membrane of both Gram-negative and gram positive bacteria, and ability to depolymerize the murein layer, which is relatively thick in gram positive cell walls.

Bacteriophage penetration of, and egress through, the inner membrane is accomplished in many, but evidently not all, phage by use of small membrane-localized proteins called "holins" that appear to accumulate in the bacterial inner membrane until reaching a specific concentration, at which time they are thought to self-assemble to permeabilize the inner membrane (Grundling et al., 2001; Wang et al. 2000; Young et al., 2000). The terms "holin" and "holin-like" are not biochemically or even functionally accurate terms, but instead in refer to any phage protein with at least one transmembrane domain that is capable of permeabilizing the inner membrane, thereby allowing molecules other than holins that are normally sequestered in the cyctoplasm by the inner membrane, including proteins such as endolysins, to breach or penetrate the inner membrane to reach the cell wall. The biochemical function(s) of holins is speculative; most, if not all of the current knowledge on holins is based on the λ phage S protein (Haro et al. 2003).

Holins are encoded by genes in at least 35 different families, having at least one transmembrane domain and classified into three topological classes (classes I, II, and III, with three, two and one transmembrane domains [TMD], respectively), all with no detected orthologous relationships (Grundling et al., 2001). At least two holins are known to be hemolytic and this hemolytic function has been hypothesized to play a role in the pathogenesis of certain bacteria towards insects and nematodes (Brillard et al., 2003). Only a few have been partially characterized in terms of in vivo function, leading to at least two very different theories of how they may function. The most widely accepted theory is that holins function to form oligomeric membrane pores (Graschopf & Blasi, 1999; Young et al., 2000).

Depolymerization of the murein layer is accomplished by lytic enzymes called endolysins. There are at least three functionally distinct classes of endolysins: 1) glucosaminidases (lysozymes) that attack the glycosidic linkages between the amino sugars of the peptidoglycan; 2) amidases that attack the N-acetylmuramoyl-L-alanine amide linkage between the glycan strand and the cross-linking peptide, and 3) endopeptidases that attack the interpeptide bridge linkages (Sheehan et al., 1997). Endolysins are synthesized without an export signal sequence that would permit them access to the peptidoglycan (murein) layer, and they therefore usually accumulate in the cytoplasm of phage infected bacteria until they are released by the activity of holins (Young and Blasi, 1995).

Lysozymes have been suggested as useful antibiotics that can be used as external agents against both Gram-positive and Gram-negative bacteria because at least some of them are multifunctional (During et al., 1999). This dual functionality is based on the finding that both phage T4 and hen egg white lysozyme have both glucosaminidase activity as well as amphipathic helical stretches that allow them to penetrate and disrupt bacterial, fungal and plant membranes (During et al., 1999). The microbicidal activity of lysozymes can be affected by C-terminal additions; additions of hydrophobic amino acids decreased activity against Gram positive bacteria, but increased activity against Gram-negative E. coli (Arima et al., 1997; Ito et al., 1997). Additions of histidine, a hydrophilic amino acid, to T4 lysozyme doubled its antimicrobial activity against Gram-positive and Gram-negative bacteria (During et al., 1999).

The nonenzymatic, microbicidal function of lysozymes appeared to be due to amphipathic C-terminal domains that could be mimicked by small synthetic peptides modeled after the C-terminal lysozyme domains (During et al., 1999). As described above, transgenic plants have been created that express lysozymes and give some resistance to certain plant pathogens. Since most endolysins accumulate to high titers within the bacterial cell without causing lysis, endolysins other than certain lysozymes such as T4 would not be expected to attack Gram-negative bacteria if externally applied, since Gram-negative bacteria are surrounded with an outer membrane comprised of LPS and a lipid bilayer that would protect its murein layer from enzymatic attack just as effectively as its inner membrane does.

In addition to mechanisms that allow phage particles egress from their hosts, all bacteriophages must also find a way to infect their host cells. Infection involves phage adsorption to the host cell surface, injection of the phage genome into the host cell, followed by replication of the phage genome and production of phage particles. Cell lysis and liberation of progeny phage particles complete the phage lytic cycle. Some host cells are surrounded by difficult-to-penetrate biofilms, consisting of a complex of exopolysaccharides (EPS), capsular polysaccharides (KPS or K-antigens) and DNA (Rendueles & Ghigo, 2012 and references therein). The extracellular matrix immediately surrounding the potential bacterial host (usually termed "capsule") contains acidic EPSs that are released into the cell's milieu. Some phages are known to release polysaccharide depolymerases that can degrade the biofilm EPS/KPS matrix, thereby allowing the phage to penetrate biofilms and capsules to reach and adsorb to the host cell surface (Donlan, 2009). Although there is evidence that an EPS depolymerase can also depolymerize similar glucans in the EPS and the O-antigenic side chains of the LPS (Grimmecke et al., 1993), there is no teaching or suggestion that degradation of the LPS is an additional targeted function in some phage, as presented in the Examples provided herein.

Phage EPS-depolymerases have been described (Kim et al., 2004 and references therein) and even used in an attempt to treat Erwinia amylovora bacterial infections of pear and apple trees through the use of transgenic plants expressing a depolymerase derived from an E. amylovora phage. However, the level of resistance achieved was weak, at best, and the phage EPS-depolymerase was very specific for the EPS from E. amylovora (Flachowsky et al., 2008). More efficacious, and more generally applicable, strategies are clearly needed.

Attempts have been made to treat bacterial diseases of both animals and plants by use of intact bacteriophage. All of these attempts have severe limitations in their utility. For examples, U.S. Pat. No. 5,688,501 discloses a method for treating an infectious disease of animals using intact bacteriophage specific for the bacterial causal agent of that disease. U.S. Pat. No. 4,957,686 discloses a method for preventing dental caries by using intact bacteriophage specific for the bacterial causal agent of dental caries. Flaherty et al. (2000) describe a method for treating an infectious disease of plants using intact bacteriophage specific for the bacterial causal agent of that disease. In all these cases and in similar cases using intact bacteriophage, the bacteriophage must attach to the bacterial host, and that attachment is highly host specific, limiting the utility of the phage to specific bacterial host species, and sometimes specific bacterial host strains. In addition, for attachment to occur, the bacteria must be in the right growth phase, and the phage must be able to gain access to the bacteria, which are often buried deep within tissues of either animals or plants, or shielded by bacterial biofilms, formed in part by the secretion of bacterial extracellular polysaccharides (EPS).

Attempts have been made to treat gram-positive bacterial diseases of animals, but not plants, by use of lytic enzyme preparations extracted from bacteriophage infected bacteria or from bacteria expressing bacteriophage genes. These, too, have serious limitations. For example, U.S. Pat. No. 5,985,271 discloses a method of treating an animal disease caused by a specific gram positive bacterium, *Streptococcus*, by use of a crude specific endolysin preparation. Similarly, U.S. Pat. No. 6,017,528 discloses a method of preventing and treating *Streptococcus* infection of animals by use of a crude specific endolysin preparation. Similarly, WO 01/90331 and US 2002/0058027 disclose methods of preventing and treating *Streptococcus* infection of animals by use of a purified preparation consisting of a specific endolysin. In all of these cases, the enzyme preparations must be purified, buffered, prepared for delivery to the target areas and preserved at the target site. In addition, the enzyme must be able to gain access to the infecting bacteria, and be present in sufficient quantity to kill the growing bacteria. None of these methods would be useful in the treatment of Gram-negative bacteria, because the endolysins could not penetrate the outer membrane of such bacteria.

Attempts have been made to treat both gram-positive and gram-negative bacterial diseases of animals, but not plants, by use of lytic enzyme preparations extracted from bacteriophage infected bacteria or from bacteria expressing bacteriophage genes. WO 01/51073, WO 01/82945, WO 01/019385, US 2002/0187136 and US 2002/0127215 disclose methods of preventing and treating a variety of gram positive and Gram-negative bacterial infections of animals by use of lytic enzymes that may optionally include specific "holin lytic enzymes" or "holin enzymes".

Since holins are not known to exhibit enzymatic function, and since examples of such holin lytic enzymes are not demonstrated or taught in WO 01/51073, WO 01/82945, WO 01/19385, US 2002/0187136 and US 2002/0127215, such enzymes appear to represent a theoretical and undemonstrated enzyme defined by reference to a desirable characteristic or property. As correctly stated elsewhere by the same inventors: "Holin has no enzymatic activity" (refer WO 01/90331, page 9 line 12). Lytic enzymes, which form the basis for the methods disclosed in all of these PCT publications, are internally defined: "The present invention is based upon the discovery that phage lytic enzymes specific for bacteria infected with a specific phage can effectively and efficiently break down the cell wall of the bacterium in question. At the same time, the substrate for the enzyme is not present in mammalian tissues . . . " (WO 01/51073 paragraph 3, page 4). "The lytic enzymes produced by bacterial phages are specific and effective for killing select bacteria." (paragraph 2, page 7).

WO 02/102405 discloses a method of preventing food poisoning in animals by inclusion of a purified preparation consisting of specific lytic enzymes and optionally, specific lytic "holin enzymes". Again, since holins are not known to exhibit enzymatic function, it is unclear as to what is taught or specified in the claims, other than a theoretical and undemonstrated enzyme defined by reference to a desirable characteristic or property.

It has been suggested that a specific endolysin from a bacteriophage that attacks a Gram-negative bacterial plant pathogen might be effective in providing resistance to that pathogen if the endolysin gene were cloned and expressed in plants (Ozawa et al., 2001). This suggestion is most unlikely, since endolysins other than T4 lysozyme are not known to penetrate bacterial membranes, and Gram-negative bacteria have a distinctive outer membrane, the LPS barrier, that provides a strong environmental barrier that is impermeable to most molecules.

It has been demonstrated that a gene from a bacteriophage infecting *Ralstonia solanacearum* encodes a lytic peptide that is capable of lysing several *R. solanacearum* strains (Ozawa et al. 2001). These authors suggested that this lytic peptide of undisclosed sequence might be used to enhance resistance against *R. solanacearum* in transgenic tobacco plants. However, there is no teaching or suggestion that this lytic peptide has bacteriocidal or bacteriostatic ability against any bacteria other than certain strains of *R. solanacearum*. Indeed, this evidently species-specific lytic peptide was expressed in *E. coli* without report of damage to the producing *E. coli* strains (Ozawa et al. 2001. This is not unexpected, since phage are highly specific for their bacterial host strains, and are normally limited in host range to a small subset of strains within a given host species. Methods are urgently needed to enhance resistance of plants against a broader range of pathogenic bacteria than a few strains of one pathogenic species.

Thus, the prior art fails to teach or describe the identification or use of phage proteins with wide anti-microbial activity against Gram-negative bacteria. The prior art also fails to teach the use genes encoding phage proteins with wide anti-microbial activity against Gram-negative bacteria. In particular, the prior art fails to teach the use of phage proteins that are capable of destabilizing or permeabilizing the outer bacterial membrane (the bacterial lipopolysaccharide or LPS barrier) for the control of Gram-negative bacterial infections of plants.

SUMMARY OF THE INVENTION

As described elsewhere herein, the present invention provides a method for outer membrane (LPS barrier) destabilization and permeabilization based upon the action of a previously undescribed bacteriophage protein called herein a Bacteriophage Outer Membrane Breaching (BOMB) protein. The present invention is based, in part, on our discovery that BOMBs carry two antiparallel beta strands in one domain, which is identifiable because the strands are predicted to form transmembrane beta-strands that are characteristic of localization to the outer membranes of Gram negative bacteria. In addition, we discovered that BOMBs carry a second domain, which is a globular enzymatic domain that not only breaches but degrades and destabilizes the Gram-negative bacterial outer membrane. This action occurs not only if the BOMB is synthesized from within the bacterial cell, but in addition, occurs if the BOMB is applied externally as well. Activity of BOMBs in destabilization of the outer membrane presumably allows natural defense molecules secreted by plants and/or by other microbes to also breach the outer membrane of the target cells, thereby compromising the "barrier function" of the Gram-negative outer membrane. Kingsley et al., (1993) provide strong evidence that the outer membrane of a plant pathogenic bacterium can function as a barrier in preventing plant defense molecules from the killing the bacteria. The invention also provides the incorporation of enzymatic cell wall depolymerization based upon peptidoglycan degrading proteins comprising BOMBs or functional fragments or variants thereof in a series of gene fusions and completely synthetic genes modeled on the gene fusions.

This invention provides: 1) methods for the identification of broad-spectrum BOMBs to breach microbial outer membranes and thereby increase the efficacy of both natural plant defense compounds and artificially applied compounds; 2) conditions required for maintaining and increasing the antimicrobial and anti-pest efficacy of BOMBs in gene fusions; 3) methods for effective targeting of BOMBs expressed in plants through use of a plant leader peptide to direct the BOMB protein to specific tissue or specific organ of the plant, such as apoplast; 4) methods for the control of Gram-negative bacterial diseases of plants by expression of gene fusions involving BOMBs and BOMB fragments, C-terminal additions and leader peptides, and optionally, endolysins, chitinases and/or lipases, and 5) transgenic plants useful for the production of novel antimicrobial proteins based upon BOMBs and BOMB fragments.

It has now been found by the present inventors that certain bacteriophage carry genes that encode proteins other than holins and endolysins that assist the phage in disrupting host cells, and specifically in disrupting the bacterial outer membrane or LPS layer found only in Gram-negative bacteria. It has further been found that at least some of these can be identified by the fact that they encode recognizable beta strand-linker-beta strand structural domains fused to a globular enzymatic domain and that this combination specifically binds to LPS and also degrades LPS. It has further been found that all such bacterial outer membrane breaching (BOMB) proteins works from the outside of the cell to compromise the integrity of the bacterial LPS outer membrane. It has further been found that expression of a BOMB protein in Gram-negative bacteria inhibits the growth of the bacteria in culture, and that when coupled with detergents, lytic proteins such as certain lysozymes or plant defense compounds such as berberine chloride, growth inhibition and/or lysis occurs. Thus it has been discovered that a BOMB protein not only can have a direct inhibitory effect on growth of Gram-negative bacteria in culture medium, but the effect is synergistic with enzymes that cause lysis and with compounds that are toxic and are otherwise blocked by an intact and functional LPS barrier.

It has further been found that BOMB proteins compromise the integrity of the bacterial LPS barrier, but not the inner membrane. Further, the present inventors have: 1) identified, cloned and expressed *Xanthomonas pelargonii* phage Xp15 BOMB protein BC in *E. coli;* 2) operably fused the bombBC gene separately to plant promoters in a gene expression cassette; 3) expressed functional BombBC in multiple different transgenic plants, both monocot and dicot, including tomato, tobacco, geranium, citrus and rice; 4) killed or inhibited growth of many different Gram-negative pathogens of said plants, conferring enhanced disease resistance or immunity to said plants. Thus it has been discovered that BombBC, and more generally, BOMBs, may be functionally expressed in both monocot and dicot plants to enhance a plant's natural disease resistance mechanisms.

This invention therefore provides a general method for strongly enhancing disease resistance in plants against Gram-negative bacteria, whether plant pathogens or not, comprising introducing into the plant a gene expression cassette operably fusing: 1) a promoter that functions in plants; 2) a BOMB gene or gene fragment that functions to express active BOMB protein in plants; 3) a transcriptional terminator region that functions in plants; and 4) obtaining expression of said gene for BOMB production in said plants.

In one embodiment, the above expression cassette containing a BOMB gene or gene fragment that functions to express active BOMB protein in plants has a plant secretion signal sequence that functions in plants, operably fused to the amino terminus of the BOMB gene or gene fragment.

The present invention further provides nucleic acid molecules, operably linked to one or more expression control elements, including vectors comprising the isolated nucleic acid molecules. The nucleic acid sequences of the present invention can be naturally produced or synthetically produced using methods well know to those skilled in the art of nucleic acid preparation.

The invention further includes host cells transformed to contain the nucleic acid molecules of the invention and methods for producing a peptide, polypeptide or protein comprising the step of culturing a host cell transformed with a nucleic acid molecule of the invention under conditions in which the protein is expressed.

This invention provides vectors comprising the nucleic acid constructs of the present invention, as well as host cells, recombinant cells and transgenic tissues and organisms comprising the vectors of the present invention. More particularly, this invention provides such cells and transgenic tissues and organisms that are hemizygotic, heterozygotic or homozygotic for the nucleic acid constructs, wherein if the organism is a plant it can be monoploid, diploid or polyploid. It is an object of the present invention to provide such cells and transgenic tissues and organisms wherein they express a single copy or multiple copies of one or more BOMB proteins, or BOMB-like ortholog protein products of the present invention. Cells or transgenic tissues and organisms which express multiple copies of one of the BOMB proteins, or BOMB-like proteins, mutant BOMB or BOMB-like proteins, or BOMB or BOMB-like ortholog proteins, or which express more than one of the BOMB or BOMB-like proteins, mutant BOMB or BOMB-like proteins, or BOMB or BOMB-like ortholog proteins, or which express a translational or transcriptional gene fusion carrying an BOMB or BOMB-like protein may be desirable, for example, to produce broad-spectrum resistance or tolerance to a variety of different Gram-negative bacteria, whether pathogens, opportunistic or saprophytic.

Gram-negative bacteria are in particular bacteria with an LPS, including but not limited to the following genera: *Agrobacterium, Burkholderia, Candidatus* Liberibacter, *Erwinia, Escherichia, Pseudomonas, Ralstonia, Salmonella, Shigella, Xanthomonas* and *Xylella.*

According to the invention it is possible to impart into virtually all plants resistance, or increased resistance, to Gram-negative bacteria, including, but not limited to, the above named pathogenic genera. There is a particular demand for the generation of such resistance in crop plants, both agronomic as well as horticultural, both for food crop use as well as ornamental. There is also a particular demand for the elimination of Gram-negative bacteria that are pathogenic to humans and animals that may be carried asymptomatically in some plants, such as fresh alfalfa and bean sprouts, lettuce and spinach. There is also a particular demand for the elimination of Gram-negative bacteria that may be carried asymptomatically in some plants, such as ornamental plants, including geraniums, but that can cause disease on other plants, such as crop plants, including potatoes. There is also particular demand for the elimination of USDA Select Agents that may be carried in crop plants such as citrus or geranium. There is also particular demand for the extension of shelf life of cut flowers, due to attack by Gram-negative bacteria that are saprophytic.

The present invention therefore also relates to a method for preparing transformed plant cells and plants, including seeds and all parts of plants, having increased resistance or immunity to Gram-negative bacterial infection or infestation, whether plant pathogenic or not. This method provides one or more BOMB genes, BOMB gene fusions, and the introduction of these genes and fusions into the genome of plant cells, followed by introduction of said genes into plant cells, regeneration of whole transformed plants from said cells, providing transgenic plants with resistance or immunity to disease, infection or infestation by Gram-negative bacteria. This invention describes the use of BOMB genes to control disease, infection and infestation in transgenic plants to: 1) control diseases otherwise affecting said transgenic plants, 2) to eliminate said transgenic plants from being carriers of diseases that affect other plants or animals (eg., nosocomial infestations or in animal feed), and 3) to prolong the shelf life of said transgenic plants if said plants are detached from roots (eg., cut flowers, grafting).

Multiple methods are used by those skilled in the art for introducing BOMB genes into plants or plant cells of dicots or monocots, including, but not limited to, use of *Agrobacterium tumefaciens* and various Ti-plasmid variations, use of *Rhizobium* spp, *Sinorhizobium* spp or *Mesorhizobium* spp. (Broothaerts et al., 2005) and various Ti-plasmid variations, use of electroporation, particle bombardment, fibrous silicon carbide whiskers or nonfibrous silicon carbide powder. Multiple methods are available to those skilled in the art for the regeneration of fully transgenic plants, including both dicots and monocots. The term "plants" as used herein denotes complete plants and also parts of plants, including seeds, tubers, cuttings, etc.

The invention further provides nucleic acid probes for the detection of expression of the BOMB or BOMB-like proteins of the present invention, or mutants, or homologs, or orthologs thereof, in for example, plants which either have been genetically altered to express at least one of said proteins or which may naturally express BOMB or BOMB-like proteins, or mutants, or homologs, or orthologs thereof.

This invention also provides the complete nucleic acid sequences for: 1) plant transformation vectors carrying functional, codon optimized, phage P15 bombBC for use in *Sinorhizobium* and in *Agrobacterium* (i.e., SEQ ID NO.: 1), 2) functional, codon optimized bombBC interrupted with the catalase intron (e.g., SEQ ID NO.: 2; see U.S. Pat. No. 7,919,601 and PCT/US08/70612, which are incorporated by reference herein in their entireties) illustrating a portion of bombBC sequence (e.g., SEQ ID NO.: 2) with only 80% sequence identity to native bombBC (refer U.S. Pat. No. 8,212,110, which is incorporated by reference herein in its entirety); 3) codon optimized bombBC (e.g., SEQ ID NO.: 3) with only 82% sequence identity to native bombBC (refer U.S. Pat. No. 8,212,110), and 4) strains for purposes of plant transformation, together with a demonstration that the codon optimized bombBC gene functions well in plants to provide plant resistance. This invention also provides demonstrations that truncated versions of bombBC (e.g., SEQ ID NOs. 4, 5, 6, and 7) suffering deletions of up to 45% of the entire length of the predicted BombBC protein still retained anti-microbial activity. This invention also provides the isolated nucleic acid sequence and its complement for Phage PhiKMV ORF 35 from *Pseudomonas aeruginosa* (e.g., Lavigne et al. 2003; SEQ ID No.: 8) and its corresponding amino acid sequence (e.g., Uniprot accession Q7Y2D0; "putative uncharacterized protein"; SEQ ID No.: 9) encoding the BombORF35PA peptide. This invention also provides the isolated nucleic acid sequence and its complement for Phage RSB1 ORF gp35 from *Ralstonia solanacearum* (e.g., Kawasaki et al. 2009; SEQ ID No.: 10) and its corresponding amino acid sequence (e.g., Genbank accession YP_002213724; "hypothetical protein; SEQ ID No.: 11) encoding the BombORF35RS peptide. This invention also provides the isolated nucleic acid sequence and its complement for Phage 13 ORF 9 from *Xanthomonas campestris* pv. *pelargonii* (e.g., SEQ ID No.: 12) and its corresponding amino acid sequence (e.g., SEQ ID No.: 13) encoding the BombOrf9 peptide. This invention also provides the isolated nucleic acid sequence and its complement for Phage 15 ORF L from *Xanthomonas campestris* pv. *pelargonii* (e.g., GenBank Accession AY986977.1; SEQ ID No.: 14) and its corresponding amino acid sequence (e.g., SEQ ID No.: 15) encoding the BombOrfL peptide (GenBank Accession AAX84855.1).

The invention further provides a means for prediction of swappable beta strand-linker-beta strand domains that are important for outer membrane targeting and may be desirable for outer membrane localization but may be dispensable if only the LPS degradation domain of the Bomb proteins is desired. The (dispensable) outer membrane targeting and LPS degradation domains are predicted and demonstrated for BombBC, and predicted for SEQ ID Nos.: 9, 11, 13 and 15.

The invention further provides the means to identify additional Bomb proteins in bacteriophage genome, including but not limited to utilizing the steps of: 1) identification of the beta strand-linker-beta strand domain by bioinformatics and 2) expression of phage protein in *E. coli* using an assay for quasilysis.

The invention further provides variations and iterations of SEQ ID No. 2, 3, 8, 10, 12 or 14, including but not limited to its corresponding DNA sequences, coding sequences, codon optimized coding sequences, genomic sequences, RNA sequences, interfering RNA (RNAi) sequences, double stranded RNAi (dsRNA) sequences, microRNA (miRNA) sequences, small interfering RNA (siRNA) sequences, expressed RNAi (eRNAi or eiRNA) sequences, antisense sequences, complementary DNA (cDNA) sequences, inverse cDNA sequences, etc.

The present invention also provides primers prepared from SEQ ID No. 1, 2, 3, 8, 10, 12 or 14 that can be used to locate and identify homologs and orthologs in any prokaryotic or eukaryotic organism. The present invention also provides methods of using such primers to obtain and isolate such homologs and orthologs to SEQ ID No. 1, 2, 3, 8, 10, 12 or 14.

The present invention also provides methods of using all or part of the sequence of SEQ ID No. 1, 2, 3, 8, 10, 12 or 14 to identify homologs or orthologs by searching nucleic acid sequence data bases. Examples of such databases include but are not limited to the genomic sequence databases for corn, rice and *Arabidopsis*. Such sequence searching methods are well known to those skilled in the art.

The present invention also provides any nucleic acid sequences that hybridize to SEQ ID No. 1, 2, 3, 8, 10, 12 or 14 under stringent conditions. Such conditions are well known to those practiced in the art, using methods taught by, for example, Sambrook et al (1989), but are normally a combination of temperature and salt concentration that is approximately 20 degrees Celsius below the calculated melting temperature ($T_m$) of the target molecule. The melting temperature is typically calculated using the formula of Bolton and McCarthy (1962).

The present invention further provides isolated nucleic acid molecules and their complements that encode a sequence with at least about 60% sequence identity to SEQ ID No. 1, 2, 3, 8, 10, 12 or 14, or at least about 65% sequence identity, or at least about 70% sequence identity, or at least about 75% sequence identify, or at least about 80% sequence identity, or at least about 85% sequence identity, or at least about 86% sequence identity, or at least about 87% sequence identity, or at least about 88% sequence identity, or at least about 89% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity, or at least about 99.5% sequence identity, or at least about 99.9% sequence identity with SEQ ID No. 1, 2, 3, 8, 10, 12 or 14. The present invention also provides any such nucleic acids which encode a peptide or protein with BOMB activity.

The present invention further provides isolated amino acids that encode a sequence with at least about 65% sequence identity to SEQ ID No. 1, 2, 3, 8, 10, 12 or 14, or at least about 70% sequence identity, or at least about 75% sequence identify, or at least about 80% sequence identity, or at least about 85% sequence identity, or at least about 86% sequence identity, or at least about 87% sequence identity, or at least about 88% sequence identity, or at least about 89% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity, or at least about 99.5% sequence identity, or at least about 99.9% sequence identity with SEQ ID No. 2. The present invention also provides the peptides and proteins encoded by such amino acid sequences including those with BOMB activity.

The invention also provides a DNA coding region consisting of bombBC (SEQ ID No. 3) or any DNA sequence consisting of a stretch of 70% DNA sequence identity over a stretch of 50 base pairs. This is a practical standard that is used by the Food Allergy Research Resource Program to determine if a protein is likely to be similar to any known allergens, based either on protein or DNA coding sequences.

The invention also provides a peptide fragment consisting of at least the 94 contiguous amino acids of functional mutant D2 of BombBC (SEQ ID No. 7), OR any peptide fragment or protein having 35%, 40%, 45%, 50%, 55%, 60%, 65%, 70%, 75%, 80%, 85%, 90%, 95%, 99%, 99.5%, 99.9% similarity over the 94 amino acids of functional mutant D2 of BombBC (SEQ ID No. 7), OR any peptide fragment or protein from SEQ ID No. 9, 11, 13 or 15 having the equivalent 94 contiguous amino acids of the corresponding regions of functional mutant D2 of BombBC.

The present invention provides an isolated nucleic acid sequence comprising, consisting essentially of, or consisting of a nucleic acid sequence of SEQ ID No. 1, 2, 3, 8, 10, 12 or 14 and conservative substitutions thereof; a nucleic acid sequence with at least 70% nucleic acid sequence identity to SEQ ID No. 1, 2, 3, 8, 10, 12 or 14; a contiguous nucleic acid sequence with at least 70% nucleic acid sequence identity to a contiguous nucleic acid sequence of at least 50 base pairs of SEQ ID No. 1, 2, 3, 8, 10, 12 or 14; a nucleic acid sequence which hybridizes to the nucleic acid sequence of SEQ ID No. 1, 2, 3, 8, 10, 12 or 14 under stringent hybridization conditions; or encodes the amino acid sequence of SEQ ID No. 4, 5, 6, 7, 9, 11, 13 or 15. The present invention also provides nucleic acid constructs, vectors, plant cells, plant parts, plant tissues and whole plants comprising such nucleic acid sequences. The plant can be any plant, such as any monocotyledonous plant or any dicotyledonous plant. Examples of such plants useful in the present invention include but are not limited to a geranium, tobacco, citrus and rice. The present invention also provides methods of transforming a plant cell comprising introducing into the plant cell the isolated nucleic acid sequences of the present invention.

The present invention may also find use in transforming or treating algae for bacterial infections, including by transforming algae with the sequences provided by the present invention.

The present invention also provides methods for enhancing the resistance of a plant to infection or infestation by Gram-negative bacteria, whether pathogenic or not, comprising introducing into the plant genome of said plant the nucleic acid sequences of the present invention.

The present invention also provides isolated peptides, polypeptides or proteins comprising, consisting essentially of, or consisting of an amino acid sequence of SEQ ID No. 4, 5, 6, 7, 9, 11, 13 or 15, or an amino acid sequence having 35% or greater amino acid sequence similarity over at least 80 amino acids with the amino acid sequence of SEQ ID No. 4, 5, 6, 7, 9, 11, 13 or 15.

The present invention also provides isolated peptides, polypeptides or proteins which are derived from a bacteriophage; lack a bacterial secretion signal amino acid sequence; lack an alpha helical transmembrane domain; that when expressed in a bacterium grown in the presence of a phytoalexin, antibiotic, detergent or other chemical, physical or biological agent at a concentration or level that is normally prevented from damaging a Gram negative bacterial cell by LPS barrier of the intact outer membrane, does not cause lysis, but instead causes "quasilysis", whereby the optical density of the culture continues to increase shortly after induction and thereafter declines to approximately the starting optical density or slightly below.

The plant cells, plant parts, plant tissues or whole plants of the present invention can also cause insects and nematodes to fail to thrive or to avoid feeding on said plant cell, plant part, plant tissue or whole plant due to inhibition or killing of symbiotic Gram-negative bacteria that are important for digestion or survival of the insect or nematode.

The present invention also provides methods of preventing, treating or reducing a Gram-negative bacterial infection or infestation of a plant cell, plant part, plant tissue or whole plant, said method comprising contacting the plant cell, plant part, plant tissue, or whole plant with the isolated peptide, polypeptide or protein of the present invention.

The present invention also provides compositions comprising the isolated peptides, polypeptides or proteins of the present invention. Examples of such compositions include but are not limited to seed treatments, such as seed coatings, and other forms of such compositions including but not limited to sprays, powders, slurries, dustings and the like.

The present invention provides methods of preventing, treating or reducing microbial infection of an animal cell, animal tissue, or whole animal, said method comprising contacting the animal cell, animal tissue, or whole animal with the isolated peptides, polypeptides or proteins of the present invention. The peptides, polypeptides or proteins may be included in compositions used to treat such animals. Examples of such compositions include but are not limited to sprays, powders, slurries, patches, implants and the like.

The present invention provides methods of preventing, treating or reducing microbial infection of a surface or device, such as a countertop used to prepare food or a medical device, said methods comprising contacting the surface or device with the isolated peptides, polypeptides or proteins of the present invention. The peptides, polypeptides or proteins may be included in compositions used to treat such surfaces and devices. Examples of such compositions include but are not limited to paints, detergents, sprays, powders, slurries, patches, implants and the like.

The present invention provides methods for enhancing the resistance of a plant cell, plant part, plant tissue or whole plant to infection or infestation by Gram-negative bacteria comprising introducing into the plant cell, plant part, plant tissue or whole plant an expression cassette comprising as operably linked components: a) a promoter region functional in plants; b) a nucleic acid sequence of claim 1, claim 2 or claim 3; and c) a terminator region functional in plants; and then allowing expression of the expression cassette; thereby obtaining enhanced resistance of the plant cell, plant part, plant tissue or whole plant to infection or infestation by Gram-negative bacteria. Such methods can further comprise self-pollinating the whole plants with the introduced expression cassette or cross-pollinating the whole plants with the introduced expression cassette to a plant of its same species. In addition, such methods can even further comprise testing the whole plants obtained by introducing the expression cassette for the presence of the expression cassette or enhanced resistance to infection or infestation by Gram-negative bacteria prior to self- or cross-pollinating the whole plants. The methods can further comprise harvesting any seeds produced as a result of the self- or cross-pollinations. Such methods can even further comprise germinating the harvested seeds to produced seedlings and testing plant cells, plant parts, plant tissues or whole plants of the germinated seedlings for the presence of the expression cassette or enhanced resistance to infection or infestation by Gram-negative bacteria.

The present invention also provides tissue cultures of the plant cells, plant parts, plant tissues or whole plants obtained by the methods of the present invention, wherein the so obtained plant cells, plant parts, plant tissues or whole plants contain the introduced expression cassette.

The whole plants obtained according to the methods of the present invention which contain the introduced nucleic acid sequences can further be self- or cross-pollinated to another plant of the same species. Any resultant seeds can be harvested and used to produce further plants for self- and cross-pollination.

The methods of the present invention can be used for both pathogenic and non-pathogenic Gram-negative bacteria.

The methods of the present invention can further comprise introducing into the plant genome a second nucleic acid sequence coding for a second peptide, polypeptide or peptide which enhances the resistance of the plant to infection or infestation by a plant pathogen. The second peptide, polypeptide or protein can include but not be limited to a nonenzymatic lytic peptide, an enzymatic lytic peptide, or an enzymatic peptidoglycan degrading peptide. For example, the second peptide, polypeptide or protein can be a lysozyme, an endolysin, a protease, a mureinolytic enzyme, an enzyme with transglycosylase activity, a lipase and an esterase.

BRIEF DESCRIPTION OF THE FIGURES

FIG. 4 shows a transgenic Florist's geranium (*Pelargonium* X *hortorum*) cultivar "Avenida" leaf expressing BombBC and inoculated at the same time and in the same manner as that described in the legend of FIG. 1. Following inoculation, plants were held at 32° C. The circular cut out region contained no detected *X. pelargonii* cells. Photo taken four weeks after inoculation.

FIG. 6 shows a comparison of nontransgenic Florist's geranium (*Pelargonium* X *hortorum*) cultivar "Avenida" leaf inoculated with *R. solanacearum* cells inoculated by syringe infiltration of $10^6$ cfu/ml directly into the spongy mesophyl of leaves using the blunt end of a tuberculin syringe. In addition, these same syringe inoculated plants were also inoculated by adding 5 ml of a $10^7$ cfu/ml liquid culture directly to the soil of the potted plants geranium plants. Following inoculation, plants were held at 32° C. to encourage pathogen growth and symptom development. Four weeks after inoculation, photographs were taken of both nontransgenic geranium variety "Avenida" (left) and transgenic geranium of the same variety "Avenida" expressing BombBC (right). Typical symptoms of bacterial wilt developed on the nontransgenic plants, which died after 12 weeks. No symptom development, other than that which initially developed in, and stayed restricted to, the region of inoculation was observed on the transgenic variety "Avenida" expression BombBC (right).

Figure 1:
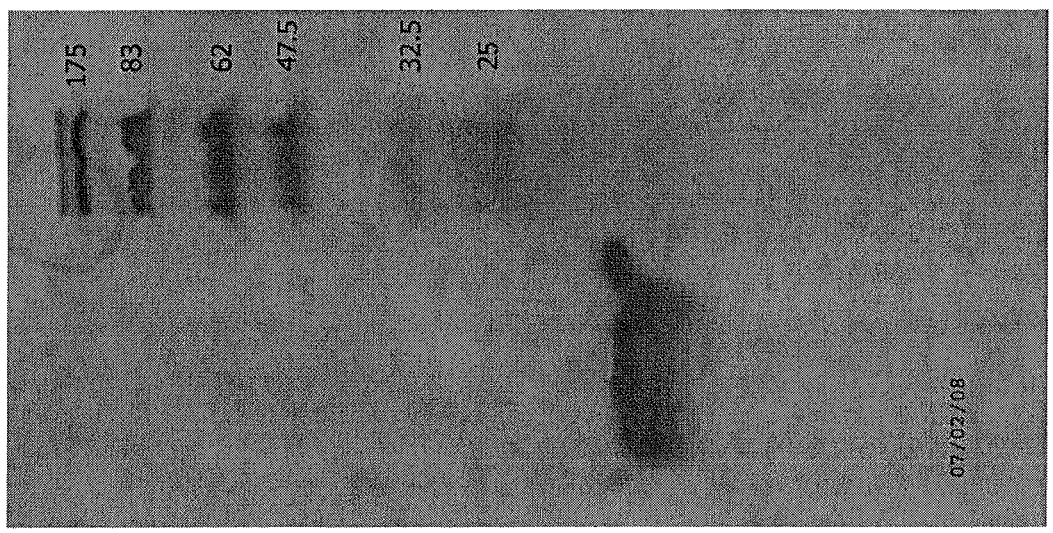
FIG. 1 shows purified BombBC protein (18 kDa) in lane 1 and molecular weight markers of indicated size in lane 2 of a polyacrylamide gel stained with Coomassie blue.

2. Following phage purification, the bacteriophage DNA is fragmented and fully sequenced, as exemplified by Phage 15 sequence deposited in GenBank as Accession NC_007024. There are a variety of strategies available for this purpose known to those skilled in the art; sequencing may be accomplished by shot-gun library sequencing or by subcloning, restriction mapping and sequencing using primer walking techniques. Phage genomic regions expressing BOMBs from Gram-negative bacteria may not be readily clonable in *E. coli* and are recognized by the fact that they can only be cloned either without their native promoters or cloned downstream of fully repressed promoters. These regions may be sequenced directly from phage DNA.

3. Following DNA sequencing of the bacteriophage genome, transcriptional direction is determined by identification of promoters and transcriptional terminators using programs well known to those skilled in the art. Phage genomes are typically transcribed as polycistronic messages in large blocks. All open reading frames (ORFs) are then identified using programs well known to those skilled in the art, and likely functional genes (LFGs) are also identified, based on length of the ORF, codon usage, third position codon bias, presence or absence of Shine-Delgarno sequences and transcriptional context, including likely promoters, transcriptional terminators and direction of transcription. The biochemical functions of some of the LFGs are then determined by comparisons with other, often characterized genes catalogued in large databases such as GenBank®. Since BOMBs have not previously been described, the BOMB genes are unlikely to be discovered by comparisons with any known genes in public or private databases.

4. The genes encoding BOMBs and/or BOMB-like genes are identified by examining every LFG of the phage, starting with those found in any DNA fragment that is not sub-clonable. BOMBs characteristically are: 1) small (20 kD or less) LFGs with 2) a domain consisting of a beta strand-loop-beta strand, 3) no alpha helical transmembrane domains, 4) a separate domain predicted to be globular and 5) no secretion leader sequences. LFGs with these characteristics are then selected for further testing using a functional gene expression assay. The predicted peptide coding regions of the putative BOMB genes are amplified by polymerase chain reaction (PCR) from the phage DNA and cloned without promoters in a suitable vector. These coding regions are then operably fused with strongly regulated, repressible promoters in suitable bacterial expression vectors. Repression of the promoter operably fused with the putative BOMB genes is then released, which should result in a noticeable reduction or termination of growth of the *E. coli* strains carrying the clones. Any such clones are then further tested for their effect on other bacteria.

5. Any DNA clones that, on induction, cause a noticeable reduction or termination of growth of the *E. coli* strains carrying the clones are further evaluated by measuring the optical density OD at 600 nanometers (nm) of the cultures over a 24 hour period of time starting with a low, but measurable OD at the time of induction. These measurements are taken in the presence and in the absence of a phytoalexin such as berberine or a detergent such as Silwet L77. Observations are made for evidence of cell lysis or lack thereof. Any DNA clones that, upon induction, cause a continuous decline in cell density over time (up to 24 hrs) are likely BOMB candidate genes. Such clones may be further confirmed as BOMB genes if the effect of added phytoalexin, such as berberine chloride, or wetting agent, such as Silwet L77 is synergistic with the DNA clone in reducing cell culture density continuously over time (up to 24 hrs). In one specific embodiment is a cloned bombBC. In another specific embodiment is a cloned bombORF35PA. In another specific embodiment is a cloned bombORF35RS. In another specific embodiment is a cloned bombORF9. In another embodiment is a cloned bombORFL.

6. Said select BOMB clones may be truncated by removing the beta strand-linker-beta strand portion of the BOMB clone. Such clones may be retested according to the methods illustrated in embodiments 5 and 6. In some embodiments, the present invention provides truncated BOMB polypeptides in which one or more dispensable fragments have been removed compared to the native BOMB polypeptides. In some embodiments, the dispensable fragments comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more amino acids within the beta strand-linker-beta strand region of the native BOMB polypeptide. In some embodiments, the truncated BOMB polypeptides without the dispensable region have the same, or substantially the same activity compared to the native BOMB polypeptides in causing quasilysis in *E. coli*. In some embodiments, the truncated BOMB polypeptides without the dispensable region cause statistically significant quasilysis in *E. coli* when compared to a blank control polypeptide which does not cause any quasilysis in *E. coli*. Any protein that does not cause any quasilysis in *E. coli* can be used as a blank control polypeptide. In some embodiments, the blank control polypeptide is a mutant BOMB polypeptide that does not cause any quasilysis in *E. coli*. In some embodiments, the native BOMB polypeptides are selected from the group consisting of Phage PhiKMV ORF 35 from *Pseudomonas aeruginosa* (BombORF35PA, SEQ ID NO. 9), Phage RSB1 ORF gp35 from *Ralstonia solanacearum* (BombORF35RS, SEQ ID NO. 11), Phage Xp13 BombOrf9 from *Xanthomonas campestris* pv. *pelargonii* (BombOrf9, SEQ ID NO. 13), Phage Xp15 BombOrfL from *Xanthomonas campestris* pv. *pelargonii* (BombOrfL, SEQ ID NO. 15), and BOMB polypeptide of *Xanthomonas* Bacteriophage P15 (BombBC, SEQ ID NO. 17).

In some embodiments, the dispensable regions include any fragment of the native BOMB polypeptides of the present invention. In some embodiments, the dispensable regions include, but are not limited to:

1) any fragment of aa 1-39 of the BombORF35PA peptide (SEQ ID NO. 9);
2) any fragment of aa 1-32 of the BombORF35RS peptide (SEQ ID NO. 11);
3) any fragment of aa 1-45 of the BombOrf9 peptide (SEQ ID NO. 13);
4) any fragment of aa 1-54 of the BombOrfL peptide (SEQ ID NO. 15); and
5) any fragment of aa 1-74 of BombBC (SEQ ID NO. 17).

These beta strand-linker-beta strand regions are clearly indicated by any of several publicly available protein analysis programs, for example, PRED-TMBB, as shown for BombBC in FIG. 6, which indicates that aa 1-74 of BombBC could be removed, resulting in mutant D2 (SEQ ID. 7).

7. Said selected BOMB clones are operably fused within a plant gene expression cassette, minimally comprising a promoter that is functional in plants, followed by the BOMB clone and followed by a plant terminator in a plant expression vector that may be used for transient gene expression in plants. Several plant promoters and promoters from plant viruses that are functional in plants are widely available for use to functionally express a foreign gene in plants in transient expression assays, for example, the CaMV promoter found in the pCAMBIA series of plant expression vectors (Cambia, Canberra, Australia). Several plant terminators are also available, including the widely available NOS terminator, also found in the pCAMBIA plant expression vector series. For transfer into plant cells, the plant expression vectors may optionally also contain T-DNA borders and ability to replicate in *Agrobacterium tumefaciens, Rhizobium* spp., *Sinorhizobium* spp. or *Mesorhizobium* spp., which are subsequently used to transfer the DNA region between the T-DNA borders into plants.

8. In another embodiment, an intron may be optionally used to increase gene expression. One example used herein is the catalase intron. Introns are known to be required for abundant expression of many genes in plants, including both dicots and ornamental plants and especially monocots, possibly by enhancing transcript stability or facilitating mRNA maturation (Callis et al., 1987; Mun, J. H. et al. 2002; Rose & Beliakoff, 2000; Rose, 2002, Simpson & Filipowicz, 1996).

9. In one embodiment, a plant secretion signal is added to the BOMB coding region. Some plant stress-associated and/or disease-associated proteins have been found to accumulate preferentially and most abundantly in the xylem of plants, presumably requiring a specific secretion signal sequence. Only a very few proteins are found in the xylem; it is unclear how they are secreted through the plant cell wall to reach the xylem. Such proteins have secretion signal peptides that are useful for targeting antimicrobial compounds to the plant apoplast and xylem; we call these "xylem secretion signal peptides". The xylem secretion signal peptide sequence is amplified from an appropriate plant source by PCR and cloned upstream of the BOMB sequence. One embodiment is a 24 amino acid plant signal peptide derived from one such protein, P12 (GenBank Accession # AF015782; Ceccardi et al., 1998).

10. Plant expression of an active, correctly folded BOMB is verified in any one of several plant species using transient gene expression (Wroblewski et al. 2005). The plant expression vector carrying the BOMB gene cloned in the gene expression cassette is transformed into *S. meliloti* or *A. tumefaciens*, and the resulting transformed cells are inoculated into plants by flooding a sizeable area of leaf tissue with diluted cell cultures. An empty vector control, consisting of the plant expression vector but without the BOMB gene cloned in the expression cassette, is also inoculated, preferably on the same leaf. After 3-4 days, protein is extracted from the plant tissue that has been inoculated and used for Western blot analysis. BOMB protein levels in the tissues inoculated with the BOMB clone are compared with BOMB levels in the tissues inoculated with the empty vector control.

11. The most active DNA constructs are then tested in host plant transient expression challenge assays using appropriate pathogenic species of Gram-negative bacteria; for example, *Xanthomonas pelargonii* inoculated into geranium or *Ralstonia solanacearum* inoculated into tobacco, geranium, tomato or pepper. Nonhost plant transient expression challenge assays may also be used, provided the nonhost plant produces a visible hypersensitive response (HR) to the challenge pathogen. In both cases, plant leaf tissues are inoculated by flooding with diluted cultures of *S. meliloti* or *A. tumefaciens* carrying the BOMB gene expression vector exactly as illustrated in embodiment 5, above, and the extent of the inoculated areas is marked. After 3-4 days, the plant tissue that has been inoculated is again super-inoculated in the same tissue zone, this time with a plant pathogen or target Gram-negative bacterium that has an antibiotic resistance marker different from that of the *A. tumefaciens* strain used. If a pathogen, visible pathogenic symptoms or the HR response observed on the empty vector control tissues is compared that observed with the BOMB clone tissues. Whether pathogen or non-pathogen, 1 cm leaf disks are removed from within the super-inoculated zones, ground in medium and cell count assays are performed, comparing cell counts from zones inoculated within the empty vector control tissues with those taken from zones inoculated with the BOMB clone.

12. Permanent transformation of plant cells, both monocots and dicots, followed by regeneration and propagation of transformed plants of the desired dicot and monocot species of interest are then undertaken.

It is also an object of the invention to prevent diseases of both monocot and dicot plants prophylactically by killing any Gram-negative bacterium that infects or feeds on the plant and causes plant disease. In one embodiment of the invention, the prophylactic and therapeutic treatment of a variety of diseases caused by various species and pathovars of *Xanthomonas, Pseudomonas, Erwinia, Agrobacterium*, Ca. Liberibacter, *Xylella, Ralstonia* and *Burkholderia* is achieved. Transgenic plants are created using plants that are hosts of the indicated pathogen genus, said host plants carrying one or more BOMB, or BOMB-like peptides fused with a xylem secretion signal peptide, operably linked with a plant promoter such that the BOMB-like peptides are made by the plants.

It is also an object of the invention to prevent food-borne diseases of humans and animals in both monocot and dicot plants by prophylactically killing any Gram-negative bacterium that infects or feeds on the plant and causes a food-borne disease of humans and/or animals. In one embodiment of the invention, the prophylactic and therapeutic elimination of fecal bacteria that can infect fresh vegetables such as spinach and bean sprouts and cause a variety of intestinal diseases, including *Escherichia, Shigella* and *Salmonella* is achieved. Transgenic plants are created using plants that are hosts of the indicated pathogen genus, said host plants carrying one or more BOMB or BOMB-like peptides fused with a xylem secretion signal peptide, operably linked with a plant promoter such that the BOMB-like peptides are made by the plants.

In another embodiment of the invention, transgenic plants are created that are hosts of the indicated genus, said host plants carrying one or more BOMB or BOMB-like peptides fused with a xylem secretions signal peptide together with an esterase, a lytic peptide or lytic enzyme, all operably linked with plant promoters such that the BOMB and/or BOMB-like peptides and lytic enzymes are made by the plant hosts. Lytic peptides or enzymes may be linear or compact and globular, and include but are not limited to lysozymes, cecropins, attacins, magainins, holins, permeability increasing proteins, etc.

It is a further object of the invention to prevent or to dampen epidemics or plagues by planting these transgenic plants as “trap” plants in an environment such that populations of infectious bacteria, fungi, nematodes or insects are reduced by feeding upon the transgenic plants. Such an environment may include commercial crops, including nontransgenic crops of the same or different plant species as the transgenic trap plants, gardens and inside buildings.

It is also an object of the invention to prophylactically prevent contamination of livestock feed and human foods by killing any Gram-negative bacterium that might contaminate the feed or foods. In another embodiment of the invention, livestock feeds may incorporate or consist of transgenic whole plants, transgenic plant parts or a crude, semi-pure or pure extract of transgenic plants expressing BOMB and/or BOMB-like enzymes or peptide fragments. In another embodiment of the invention, human foods such as eggs or sprouts may be treated with a spray preparation of BOMBs and or BOMB-like enzymes or peptide fragments made from transgenic plants.

DEFINITIONS

As used herein, the term "Bacterial Outer Membrane Breaching", "BOMB" or "Bomb" refers inclusively to any bacteriophage derived/originated protein or polypeptide: 1) without a bacterial secretion signal sequence; 2) without an alpha helical transmembrane domain and 3) with the capacity to negatively affect, breach, permeabilize or degrade the outer LPS barrier of Gram-negative bacteria. Expression of a BOMB protein in *E. coli* causes "quasilysis"—upon induction, and in the presence of a phytoalexin, antibiotic, detergent or other chemical, physical or biological agent that is used at a concentration or treatment dose normally prevented from damaging a Gram negative bacterial cell by the intact outer membrane, the optical density of the cell culture continues to increase for a certain period of time, for example, about one to two hours in a manner similar to that of an uninduced culture, but then the optical density drops back to, or below, the starting level at the time of induction. BOMBs lack the capacity to directly cause lysis, which would appear as an abrupt reduction of the optical density of the cell culture upon induction of the gene. BOMBs also lack the capacity to disrupt the inner membrane of bacteria in a manner similar to that of holins when produced or overproduced inside a bacterial cell.

As used herein, the term "derived", "deriving", "originated" or "originating" when used with in the context of a protein/polypeptide and a bacteriophage (phage), refers to that the protein/polypeptide is isolated from a bacteriaphage or is based on a BOMB found in a bacteriaphage.

As used herein, the term "quasilysis" refers to the phenomenon that after expression of a polypeptide of the present invention in *E. coli* or other Gram-negative bacteria, the optical density of the bacterial cell culture continues to increase for a period of time (e.g., for about one to about two hours) in a manner similar to that of a control cell culture in which the polypeptide is not expressed, but then the optical density of the bacterial cell culture expressing the polypeptide drops back to the starting level at the time of induction, or declines to a level below that of the starting optical density. Quasilysis is assayed using Gram negative bacterial cells grown in the presence of a phytoalexin, antibiotic, detergent or other chemical, physical or biological agent that is normally prevented from damaging a Gram negative bacterial cell by the intact outer membrane. Disruption or breaching of the outer membrane enables phytoalexins, antibiotics, detergents or other chemical, physical or biological agents to kill or inhibit growth of affected bacteria at significantly lower concentrations—typically 5× to 20× lower—than would otherwise be needed by the same agents to affect the cells.

As used herein, the term "significant" or "significantly" when used in a context of statistics, refers to that the probability of a difference between two numbers or groups of numbers is at least 95% (i.e., the Confidence Interval is at least 95%).

As used herein, the term "lysis" refers to the phenomenon that after expression of a polypeptide of the present invention in *E. coli* or other Gram-negative bacteria, the optical density of the bacterial cell culture drops abruptly.

As used herein, the term "holin" refers to any bacteriophage derived protein with at least one alpha helical transmembrane domain with the capacity to disrupt the inner membrane of bacteria when produced without a leader inside a bacterial cell. Disruption of the inner membrane of a bacterium is assayed by expression of both the holin gene and an endolysin gene simultaneously inside a bacterial cell; over-expression of a holin gene and endolysin simultaneously will result in cell lysis within several hours or less.

As used herein, the term "endolysin" refers to any enzyme capable of depolymerization of the murein or peptidoglycan cell wall. The term includes: 1) glucosaminidases (lysozymes) that attack the glycosidic linkages between the amino sugars of the peptidoglycan; 2) amidases that attack the N-acetylmuramoyl-L-alanine amide linkage between the glycan strand and the cross-linking peptide, and 3) endopeptidases that attack the interpeptide bridge linkages (Sheehan et al., 1997). Endolysins are synthesized without an export signal sequence that would permit them access to the peptidoglycan (murein) layer, and they therefore usually accumulate in the cytoplasm of phage infected bacteria until they are released by the activity of holins.

As used herein, the term "esterase" refers inclusively to any enzyme categorized as either a carboxylic-ester hydrolase (EC 3.1.1.1) or a triacylglycerol acylhydrolase (EC 3.1.1.3).

As used herein, the term "carboxylic-ester hydrolase" (EC 3.1.1.1), refers to a "carboxylesterase" and catalyzes the reaction of a carboxylic ester+$H_2O$ to an alcohol plus a carboxylate. Other common names for carboxylic-ester hydrolase are: ali-esterase; B-esterase; monobutyrase; cocaine esterase; procaine esterase; methylbutyrase; vitamin A esterase; butyryl esterase; carboxyesterase; carboxylate esterase; carboxylic esterase; methylbutyrate esterase; triacetin esterase; carboxyl ester hydrolase; butyrate esterase; methylbutyrase; carboxylesterase; propionyl esterase; nonspecific carboxylesterase; esterase D; esterase B; esterase A; serine esterase; carboxylic acid esterase; cocaine esterase.

As used herein, the term "lipase" refers to any triacylglycerol acylhydrolase (EC 3.1.1.3), commonly called "triacylglycerol lipase" and catalyzing the reaction of triacylglycerol plus $H_2O$ to diacylglycerol plus a carboxylate. Other common names for lipase are: tributyrase; butyrinase; glycerol ester hydrolase; tributyrinase; Tween hydrolase; steapsin; triacetinase; tributyrin esterase; Tweenase; amino N-AP; Takedo 1969-4-9; Meito MY 30; Tween esterase; GA 56; capalase L; triglyceride hydrolase; triolein hydrolase; tween-hydrolyzing esterase; amano CE; cacordase; triglyceridase; triacylglycerol ester hydrolase; amano P; amano AP; PPL; glycerol-ester hydrolase; GEH; meito Sangyo OF lipase; hepatic lipase; lipazin; post-heparin plasma protamine-resistant lipase; salt-resistant post-heparin lipase; heparin releasable hepatic lipase; amano CES; amano B; tributyrase; triglyceride lipase; liver lipase; hepatic monoacylglycerol acyltransferase.

As used herein, the term "Gram-negative bacterium" refers to any bacterium producing lipopolysaccharide (LPS).

As used herein, the verb "comprise" and its conjugations as is used in this description and in the claims are used in their non-limiting sense to mean that items following the word are included, but items not specifically mentioned are not excluded.

The invention provides plant parts. As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, brassica leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other brassica leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of *cucumis* melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, quinoa, oil palm), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fiber crops (e.g. hemp, cotton), ornamentals, citrus, geranium, tobacco, tomato, the legumes, peas, alfalfa, clover, soybeans, oaks, maples, roses, mints, squashes, daisies, walnuts, cacti, violets, buttercups and the like.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "plant promoter" is a promoter capable of initiating transcription in plant cells whether or not its origin is a plant cell, e.g. it is well known that Agrobactenum promoters are functional in plant cells. Thus, plant promoters include promoter DNA obtained from plants, plant viruses and bacteria such as *Agrobacterium* and *Bradyrhizobium* bacteria. A plant promoter can be a constitutive promoter or a non-constitutive promoter.

As used herein, a "constitutive promoter" is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or scorable markers, allowing easy detection and quantification; high level of production of a transcription factor that is part of a regulatory transcription system; production of compounds that requires ubiquitous activity in the plant; and production of compounds that are required during all stages of plant development. Non-limiting exemplary constitutive promoters include, CaMV 35S promoter, opine promoters, ubiquitin promoter, actin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues, such as stems, leaves, roots, or seeds.

As used herein, "inducible" or "repressible" promoter is a promoter which is under chemical or environmental factors control. Examples of environmental conditions that may effect transcription by inducible promoters include anaerobic conditions, or certain chemicals, or the presence of light.

As used herein, the term "disease resistance" refers to any reduction in disease symptoms or pathogen numbers in the plant or material tested caused by the treatment, as compared with the most susceptible phenotypic symptoms or pathogen numbers known in comparable tests of untreated plants or materials.

As used herein, the term "alpha helical transmembrane domain" refers to a transmembrane domain comprising one or more alpha helical structures; alpha helical transmembrane domains are commonly referred to as "transmembrane domains".

As used herein, the term "beta-barrel domains" refers to any domain containing a set of beta strands that are predicted to form beta barrels.

As used herein, the term "beta strand-linker-beta strand domains" when used regarding a polypeptide refers to a specific region of the polypeptide identified as encoding at least two membrane-spanning beta strands, each separated by a variable length of amino acids that function to physically and flexibly link the two or more beta strands and allowing the formation of at least a two stranded, anti-parallel beta sheet.

As used herein, the term "linker" or "linker region" when used regarding a polypeptide refers to a peptide sequence composed of flexible amino acids residues like glycine and serine such that the adjacent protein domains are free to move relative to one another to ensure that two adjacent domains do not sterically interfere with one another and can form at least a beta sheet.

As used herein, the term "beta strand" when used regarding a polypeptide refers to a membrane-spanning stretch of amino acids, typically 5-10 amino acids long, whose peptide backbones are almost fully extended with the sidechains of neighboring residues projected in alternating opposite directions from the backbone.

As used herein, the term "resistance" to bacteria refers to any reduction in bacterial numbers in the plant or material tested caused by the treatment, as compared with untreated plants or materials.

As used herein, the term "immunity" to bacteria refers to elimination of detectable bacterial cell counts in the plant or material tested caused by the treatment, as compared with untreated plants or materials.

As used herein, the term "allele" refers to any of several alternative forms of a gene.

As used herein, the term "amino acid" refers to the aminocarboxylic acids that are components of proteins and peptides. The amino acid abbreviations are as follows: A (Ala); C (Cys); D (Asp); E (Glu); F (Phe); G (Gly); H (His); I (Iso); K (Lys); L (Leu); M (Met); N (Asn); P (Pro); Q (Gln); R (Arg); S (Ser); T (Thr); V (Val); W (Trp), and Y (Tyr).

As used herein, "Homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." In addition, when the terms "homology" or "identity" are used herein to refer to the nucleic acids and proteins, it should be construed to be applied to homology or identity at both the nucleic acid and the amino acid sequence levels. A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul et al. (1990, J. Mol. Biol. 215:403-410), and can be accessed, for example, at the BLAST site of the National Center for Biotechnology Information (NCBI) world wide web site at the National Library of Medicine (NLM) at the National Institutes of Health (NIH). BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blasts" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used as available on the website of the National Center for Biotechnology Information of the National Library of Medicine at the National Institutes of Health.

The percent identity between two sequences can be determined using techniques similar to those described above, with or without allowing gaps. In calculating percent identity, typically exact matches are counted.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "crop plant" refers to any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food or food additives, smoking products, pulp production and wood production.

As used herein, the term "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include citrus; geranium; tobacco; tomato; the legumes, including peas, alfalfa, clover and soybeans; oaks; maples; roses; mints; squashes; daisies; walnuts; cacti; violets and buttercups.

As used herein, the term "ER retention signal" refers to an amino acid sequence (the ER retention signal peptide) attached to a polypeptide which causes the polypeptide to be retained and accumulated in the endoplasmic reticulum (ER).

As used herein, the term "female plant" refers to a plant that produces ovules. Female plants generally produce seeds after fertilization. A plant designated as a "female plant" may contain both male and female sexual organs. Alternatively, the "female plant" may only contain female sexual organs either naturally (e.g., in dioecious species) or due to emasculation (e.g., by detasselling).

As used herein, the term "filial generation" refers to any of the generations of cells, tissues or organisms following a particular parental generation. The generation resulting from a mating of the parents is the first filial generation (designated as "F1" or "$F_1$"), while that resulting from crossing of F1 individuals is the second filial generation (designated as "F2" or "$F_2$").

As used herein, the term "gamete" refers to a reproductive cell whose nucleus (and often cytoplasm) fuses with that of another gamete of similar origin but of opposite sex to form a zygote, which has the potential to develop into a new individual. Gametes are haploid and are differentiated into male and female.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms. As used herein, the term "globular domain" refers to an identifiable protein domain that is structurally compact, typically with a hydrophobic core, and having more interactions among the amino acids within the domain than with the rest of the protein.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the term "lytic protein" refers to any enzyme, in whole or in part, or lytic peptide that: 1) degrades or penetrates the peptidoglycan or murein layer that forms the bacterial cell wall of both Gram positive or Gram-negative bacteria, and 2) has the ability to permeabilize or disrupt the bacterial inner membrane. Said proteins may be linear, partially degraded or compact and globular, and include but are not limited to lysozymes, cecropins, attacins, magainins, permeability increasing proteins, etc.

As used herein, the term "male plant" refers to a plant that produces pollen grains. The "male plant" generally refers to the sex that produces gametes for fertilizing ova. A plant designated as a "male plant" may contain both male and female sexual organs. Alternatively, the "male plant" may only contain male sexual organs either naturally (e.g., in dioecious species) or due to emasculation (e.g., by removing the ovary).

As used herein, the term "mass selection" refers to a form of selection in which individual plants are selected and the next generation propagated from the aggregate of their seeds.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the terms "mutant" or "mutation" refer to a gene, cell, or organism with an abnormal genetic constitution that may result in a variant phenotype.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. The term "nucleic acid" also encompasses polynucleotides synthesized in a laboratory using procedures well known to those skilled in the art.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the terms "ortholog" and "orthologue" refer to a nucleic acid or peptide sequence which functions similarly to a nucleic acid or peptide sequence from another species. For example, where one gene from one plant species has a high nucleic acid sequence similarity and codes for a protein with a similar function to another gene from another plant species, such genes would be orthologs.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "phytoalexin" refers to any antimicrobial chemical compound made by a plant, whether preformed or made in response to presence of a microbe.

As used herein, the term "plant line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "promoter" refers to a region of DNA involved in binding RNA polymerase to initiate transcription.

As used herein, the terms "protein," "peptide" or polypeptide" refer to amino acid residues and polymers thereof. Unless specifically limited, the terms encompass amino acids containing known analogues of natural amino acid residues that have similar binding properties as the reference amino acid and are metabolized in a manner similar to naturally occurring amino acid residues. Unless otherwise indicated, a particular amino acid sequence also implicitly encompasses conservatively modified variants thereof (e.g. conservative substitutions) as well as the sequence explicitly indicated. The term "polypeptide" also encompasses polypeptides synthesized in a laboratory using procedures well known to those skilled in the art.

As used herein, the term "recombinant" refers to a cell, tissue or organism that has undergone transformation with recombinant DNA. The original recombinant is designated as "R0" or "$R_0$." Selfing the R0 produces a first transformed generation designated as "R1" or "$R_1$."

As used herein, the term "secretion signal" refers to an amino acid sequence (the secretion signal peptide) attached to a N-terminus of a polypeptide, which is needed for secretion of the mature polypeptide from the cell.

As used herein, the term "self pollinated" or "self-pollination" means the pollen of one flower on one plant is applied (artificially or naturally) to the ovule (stigma) of the same or a different flower on the same plant.

As used herein, the term "transcript" refers to a product of a transcription process.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, the term "transposition event" refers to the movement of a transposon from a donor site to a target site.

As used herein, the term "variety" refers to a subdivision of a species, consisting of a group of individuals within the species that are distinct in form or function from other similar arrays of individuals.

As used herein, the terms "untranslated region" or "UTR" refer to any part of a mRNA molecule not coding for a protein (e.g., in eukaryotes the poly(A) tail).

As used herein, the term "vector" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

Variant Bomb gene sequences may be produced by standard DNA mutagenesis techniques. In one specific, non-limiting, embodiment, M13 primer mutagenesis is performed. Details of these techniques are provided in Sambrook et al. (In *Molecular Cloning: A Laboratory Manual*, Cold Spring Harbor Laboratory Press, New York, 1989), Ch. 15. By the use of such techniques, variants may be created that differ from a naturally isolated Bomb gene. DNA molecules and nucleotide sequences that are derivatives of those specifically disclosed herein, and which differ from those disclosed by the deletion, addition, or substitution of nucleotides while still encoding a protein having the biological activity of the prototype enzyme. The resulting product gene can be cloned as a DNA insert into a vector.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (*J. Bacteriol.*, 169: 751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., *Proc. Natl. Acad. Sci. USA*, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows non-limiting exemplary conservative amino acid substitutions.

| | Conservation Amino Acid Substitution | | |
|---|---|---|---|
| Original Residue | Very Highly - Conserved Substitutions | Highly Conserved Substitutions (from the Blosum90 Matrix) | Conserved Substitutions (from the Blosum65 Matrix) |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can be replaced with a different hydrophobic residue (such as Leu, Ile, Val, Met, Phe, or Trp) to create a variant functionally similar to any of the BOMB proteins as mentioned herein.

In some embodiments, variants may differ from the BOMB proteins described herein by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the BOMB proteins described herein. For example, because of the degeneracy of the genetic code, four nucleotide codon triplets (GCT, GCG, GCC and GCA) code for alanine. The coding sequence of any specific alanine residue within a BOMB protein, therefore, could be changed to any of these alternative codons without affecting the amino acid composition or characteristics of the encoded protein. Based upon the degeneracy of the genetic code, variant DNA molecules may be derived from the nucleic acid sequences disclosed herein using standard DNA mutagenesis techniques, as described herein, or by synthesis of DNA sequences.

Based on the polynucleotide sequences of BOMB genes and polypeptide sequences of BOMB proteins described in the invention, variant nucleic acid sequences encoding a protein having similar function of BOMB protein can be designed by virtue of the degeneracy of the genetic code. Variant nucleic acid sequences encoding a protein having similar function of BOMB protein from a species other than those mentioned herein. In some embodiments, homologous genes from other species can be cloned by the classical approach, wherein it involves the purification of the target protein, obtaining amino acid sequences from peptides generated by proteolytic digestion and reverse translation of the peptides. The derived DNA sequence, which is bound to be ambiguous due to the degeneracy of the genetic code, can then be employed for the construction of probes to screen a gene library. In some embodiments, PCR methods can be used to isolate fragments of homologous genes containing at least two blocks of conserved amino acids. The amino acid sequence of a conserved region is reverse translated and a mixture of oligonucleotides is synthesized representing all possible DNA sequences coding for that particular amino acid sequence. Two such degenerate primer mixtures derived from appropriately spaced conserved blocks are employed in a PCR reaction. The PCR products are then, usually after enrichment for the expected fragment length, cloned and sequenced. In some embodiments, a homologous BOMB gene or protein can be isolated based on hybridization of two nucleic acid molecules under stringent conditions. More detailed methods of cloning homologous genes based on a known gene is described in "Gene Cloning and DNA Analysis: An Introduction", (Publisher: John Wiley and Sons, 2010, ISBN 1405181737, 9781405181730), and "Gene cloning: principles and applications" (Publisher: Nelson Thornes, 2006).

Plant Transformation

As discussed herein, several embodiments of the present invention employ expression units (or expression vectors or systems) to express an exogenously supplied nucleic acid sequence in a plant. Methods for generating expression units/systems/vectors for use in plants are well known in the art and can readily be adapted for use in the instant invention. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefacians*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as RUBISCO small and large subunit promoters, prolifera promoter, fruit-specific promoters, Ap3 promoter, heat shock promoters, seed-specific promoters, etc. can also be used.

Either a gamete-specific promoter, a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)).

The resulting expression unit is ligated into or otherwise constructed to be included in a vector that is appropriate for higher plant transformation. The vector may also contain a selectable marker gene by which transformed plant cells can be identified in culture. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as ampicillin, kanamycin or tetracycline.

Other DNA sequences encoding additional functions may also be present in the vector, as is known in the art. For instance, in the case of *Agrobacterium, Rhizobium, Mesorhizobium* and *Sinorhizobium* transformations, T-DNA sequences will also be included for subsequent transfer to plant chromosomes.

The sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., FEBS Lett. 405(2):129-132 (1997); *Arabidopsis thaliana* Database. For a discussion of the analysis of gene-expression patterns derived from large EST databases, see, e.g., M. R. Fannon, TIBTECH 14:294-298 (1996).

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; *Agrobacterium-, Rhizobium-, Mesorhizobium-* and *Sinorhizobium*-mediated transformation. See, for example, U.S. Pat. Nos. 5,405,765; 5,472,869; 5,538,877; 5,538,880; 5,550,318; 5,641,664; 5,736,369; 5,736369; US 2005/0289672; US 2005/0289667, PCT Publication WO 2006/004914; Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); Raineri et al., Bio/Tech. 8:33-38 (1990), and Broothaerts et al., Nature 433:629-633 (2005), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. It can also insert foreign DNA into plants through the use of its modified or "disarmed" natural DNA insertion system, but without forming crown gall disease. Most species of plants can now be transformed using this method. See, for example, Wang et al., Australian Journal of Plant Physiology 23(3): 265-270 (1996); Hoffman et al., Molecular Plant-Microbe Interactions 10(3): 307-315 (1997); and, Trieu et al., Plant Cell Reports 16:6-11 (1996).

*Rhizobium* spp., *Mesorhizobium* spp. and *Sinorhizobium* spp. are naturally occurring bacteria that are also capable of inserting foreign DNA (genetic information) into plants. Many species of plants can now be transformed using this method. See, for example, Broothaerts et al., Nature 433:629-633 (2005).

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method, including alfalfa (U.S. Pat. No. 5,324,646) and clover (Voisey et al., Biocontrol Science and Technology 4(4): 475-481 (1994); Quesbenberry et al., Crop Science 36(4): 1045-1048 (1996); Khan et al., Plant Physiology 105 (1): 81-88 (1994); and, Voisey et al., Plant Cell Reports 13(6): 309-314 (1994)).

Developed by ICI Seeds Inc. (Garst Seed Company) in 1993, WHISKERS™ is an alternative to other methods of inserting DNA into plant cells (e.g., the Biolistic® Gene Gun, *Agrobacterium tumefaciens*, the "Shotgun" Method, etc.); and it consists of needle-like crystals ("whiskers") of silicon carbide. The fibers are placed into a container along with the plant cells, then mixed at high speed, which causes the crystals to pierce the plant cell walls with microscopic "holes" (passages). Then the new DNA (gene) is added, which causes the DNA to flow into the plant cells. The plant cells then incorporate the new gene(s); and thus they have been genetically engineered.

The essence of the WHISKERS™ technology is the small needle-like silicon carbide "whisker" (0.6 microns in diameter and 5-80 microns in length) which is used in the following manner. A container holding a "transformation cocktail" composed of DNA (e.g., agronomic gene plus a selectable marker gene), embryogenic corn tissue, and silicon carbide "whiskers" is mixed or shaken in a robust fashion on either a dental amalgam mixer or a paint shaker. The subsequent collisions between embryogenic corn cells and the sharp silicon carbide "whiskers" result in the creation of small holes in the plant cell wall through which DNA (the agronomic gene) is presumed to enter the cell. Those cells receiving and incorporating a new gene are then induced to grow and ultimately develop into fertile transgenic plants.

Not surprisingly, the fibrous, needle-like "whiskers" form of silicon carbide is a pulmonary health hazard and therefore must be handled much differently from non-fibrous silicon carbide powders that contain no whiskers. The two silicon carbide forms, powder and fibrous whiskers, are regulated much differently, with the British Columbian (Canadian) Occupational Health and Safety (OHS) regulating the fibrous form the same as asbestos at 0.1 fiber per cc (f/cc) exposure limit, whereas the ordinary, non-fibrous form has an exposure limit of 3-10 mg/cubic meter. Silicon carbide whiskers were shown to generate mutagenic reactive hydroxyl radicals in a manner similar to asbestos and to cause DNA strand breakage; silicon carbide powder did not cause such effects (Svensson et al., 1997).

Breaching the plant cell wall using silicon carbide powder does not direct any DNA associated with the powder to the plant nucleus, although this will happen at a low frequency. This problem can be overcome if the DNA is directed to the nucleus, as occurs in natural infections of *A. tumefaciens* or by certain viruses. Nuclear localization signal sequences (NLSs) guide the protein and any associated nucleic acid to the plant nucleus.

Genes successfully introduced into plants using recombinant DNA methodologies include, but are not limited to, those coding for the following traits: seed storage proteins, including modified 7S legume seed storage proteins (see, for example, U.S. Pat. Nos. 5,508,468, 5,559,223 and 5,576, 203); herbicide tolerance or resistance (see, for example, De Greef et al., Bio/Technology 7:61 (1989); U.S. Pat. No. 4,940, 835; U.S. Pat. No. 4,769,061; U.S. Pat. No. 4,975,374; Marshall et al. (1992) Theor. Appl. Genet. 83, 435; U.S. Pat. No. 5,489,520; U.S. Pat. No. 5,498,544; U.S. Pat. No. 5,554,798; Powell et al., Science 232:738-743 (1986); Kaniewski et al., Bio/Tech. 8:750-754 (1990)); Day et al., Proc. Natl. Acad. Sci. USA 88:6721-6725 (1991)); phytase (see, for example, U.S. Pat. No. 5,593,963); resistance to bacterial, fungal, nematode and insect pests, including resistance to the lepidoptera insects conferred by the Bt gene (see, for example, U.S. Pat. Nos. 5,597,945 and 5,597,946; Johnson et al., Proc. Natl. Acad. Sci. USA, 86:9871-9875 (1989); Perlak et al., Bio/Tech. 8:939-943 (1990)); lectins (U.S. Pat. No. 5,276, 269); flower color (Meyer et al., Nature 330:677-678 (1987); Napoli et al., Plant Cell 2:279-289 (1990); van der Krol et al., Plant Cell 2:291-299 (1990)); Bt genes (Voisey et al., supra); neomycin phosphotransferase II (Quesbenberry et al., supra); the pea lectin gene (Diaz et al., Plant Physiology 109(4): 1167-1177 (1995); Eijsden et al., Plant Molecular Biology 29(3):431-439 (1995)); the auxin-responsive promoter GH3 (Larkin et al., Transgenic Research 5(5):325-335 (1996)); seed albumin gene from sunflowers (Khan et al., Transgenic Research 5(3):179-185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra), each of which is expressly incorporated herein by reference in their entirety.

For certain purposes, different antibiotic or herbicide selection markers may be preferred. Selection markers used routinely in transformation include the nptII gene which confers resistance to kanamycin and related antibiotics (see, for example, Messing & Vierra, Gene 19: 259-268 (1982); Bevan et al., Nature 304:184-187 (1983)), the bar gene which confers resistance to the herbicide phosphinothricin (White et al., Nucl Acids Res 18: 1062 (1990), Spencer et al., Theor Appl Genet 79: 625-631(1990)), and the dhfr gene, which confers resistance to methotrexate (Bourouis et al., EMBO J. 2(7): 1099-1104 (1983)).

A transgenic plant formed using *Agrobacterium, Rhizobium, Mesorhizobium* or *Sinorhizobium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Assuming normal hemizygosity, selfing will result in maximum genotypic segregation in the first selfed recombinant generation, also known as the R1 or $R_1$ generation. The R1 generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few R1 plants need to be grown to find at least one resistance phenotype (U.S. Pat. Nos. 5,436,175 and 5,776,760).

As mentioned above, self-pollination of a hemizygous transgenic regenerated plant should produce progeny equivalent to an F2 in which approximately 25% should be homozygous transgenic plants. Self-pollination and testcrossing of the F2 progeny to non-transformed control plants can be used to identify homozygous transgenic plants and to maintain the line. If the progeny initially obtained for a regenerated plant were from cross-pollination, then identification of homozygous transgenic plants will require an additional generation of self-pollination (U.S. Pat. No. 5,545,545).

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, *In Hybridization of Crop Plants*.

It should be understood that the examples and embodiments described herein are for illustrative purposes only and that various modifications or changes in light thereof will be suggested to persons skilled in the art and are to be included within the spirit and purview of this application.

EXAMPLES

Example 1

Use of a Plant Pathogen to Isolate Bacteriophage Capable of Infecting a Gram-Negative Plant Pathogen, *Xanthomonas Pelargonii*

An overnight culture of *X. campestris* pv. *pelargonii* (syn. *X. pelargonii*) strain CHSC was grown at 30° C. in PYGM medium (peptone, yeast extract, glycerol and morpholinepropanesulfonic acid; DeFeyter et al. 1990) with moderate shaking. Five ml of this overnight culture plus 50 ml of unsterilized water taken from the edge of a large pond in an agricultural setting was added to 50 ml of PYGM plus 2.5 g $CaCO_3$ and allowed to incubate at 30° C. for 48 hours without shaking. Following incubation, 1 ml of this enrichment culture was centrifuged for 1 minute at 5000 g to remove most bacteria and debris, and 500 μl of the supernatant was removed and sterilized with a drop of chloroform. Droplets of this supernatant were placed atop an overlay plate containing strain CHSC in top agar. Overlay plates were PYGM agar plates overlayed with 200 μl of overnight CHSC broth culture added to 3 ml 0.7% water agar held at 50° C. and allowed to cool and solidify. Plaques were observed after 24 hrs. incubation; these were collected by scraping the plaques from the plates, titered and stored according to standard procedures (Sambrook et al., 1989). These mixtures of phage were then purified from single plaques, and individual phage tested for bacterial host range against *X. citri* strain B21.2, *X. campestris* strain 528, and *Ralstonia solanacearum* strain G2. All phage were specifically able to attack only *X. pelargonii* strain CHSC and did not infect the other strains.

Example 2

Use of Agar Plate Overlay Assays to Characterize Phage Host Range and to Identify Phage with an Ability to Kill Bacterial Hosts that they Cannot Infect PYGM plates were overlaid with *X. pelargonii* CHSC and droplets of various purified phage samples obtained from Example 1 were added to the plates and incubated at 30° C. for 48 hours. All phage were able to infect CHSC and cause clear zones of lysis. Cell suspensions of overnight broth cultures of *X. citri* B21.2, *X. campestris* 528 and *R. solanacearum* G2 were added to 0.7% water agar as described in Example 1 and individually overlayed on the phage infected CHSC plates.

Plates were incubated an additional 48 hrs at 30° C. and phage were evaluated for ability to kill Gram-negative bacteria that they could not infect from the outside. Some phage exhibited presence of a strong, apparently diffusible killing factor for all bacteria tested. Phage isolate 15 (P15) was selected for sequencing and further evaluation.

Example 3

Use of Genomic Sequencing and Annotation Techniques to Identify Gene Candidates from Phage P15 Encoding Proteins with Ability to Kill Bacteria from the Outside The P15 genome was completely sequenced in order to identify the gene(s) expressing the diffusible killing factor. P15 DNA was made according to standard protocols using *X. pelargonii* strain CHSC as the host bacterium. The P15 DNA was digested with EcoRV, yielding eleven fragments, ranging in size from 12.4 kb to 357 bp. Most of the fragments were cloned; some were not cloned, despite repeated attempts, most likely due to the presence of restriction endonucleases and holins. The cloned DNA fragments were used directly for sequencing, using vector-based primers initially, and primer walking thereafter until each fragment was completed. Fragments that were not cloned were sequenced using P15 genomic DNA. Fragment assembly was accomplished using P15 genomic DNA and primers extending outside each fragment in both directions. P15 has a double stranded DNA genome which is 55,770 bp in length (GenBank NC_007024). The sequence of P15 is also provided as SEQ ID No. 1 in priority document PCT/US2004/015099, wherein both the sequence per se and PCT/US2004/015099 are incorporated in their entireties herein for all purposes.

ORF analysis of the sequenced phage was done using a combination of several programs including PromScan, Terminator (GCG), GeSTer (Unniraman et al. 2001, 2002), Glimmer, Genie, Codon preference (GCG), ORF finder (NCBI) and Blast (NCBI) analyses. Potential Shine-Delgarno sequences were identified manually by examining the sequence. Using default Glimmer settings, only 32 ORFs were identified; none of these ORFs corresponded to functional genes later identified as holins or BOMB by functional analyses, although lysY, predicted to encode an endolysin, was identified. After identifying the promoters and terminators in the genome, manual analysis of all ORFs using Codon preference (GCG) allowed the identification of an additional 52 ORFs, including those predicted to encode holins. The genome encoded 84 putative ORFS (GenBank NC_007024). There were several predicted ORFs of unknown function. Phage P15 ORF "BC" (bombBC; SEQ ID No. 1) was predicted to encode a 17.9 kD protein with a charge of −0.5 at neutral pH (BombBC; SEQ ID No. 2). SEQ ID No. 2 of the present continuation-in-part application is the same as SEQ ID No. 82 in U.S. application Ser. No. 10/556,563 and PCT/US2004/015099. The present application claims priority to each of these applications and both applications are incorporated in their entireties (i.e., including but not limited to their sequence listings) herein for all purposes. This ORF was among several Phage P15ORFs cloned, expressed and functionally evaluated for evidence of effect on the *E. coli* outer membrane.

Example 4

Use of a Phytoalexin and Inducible Gene Expression Systems to Identify Candidate Genes Encoding Proteins with Ability to Kill from the Outside As detailed above, bacteriophage are known to encode proteins that are able to degrade the bacterial cell wall (endolysins) and proteins that are able to degrade or breach the bacterial inner membrane (holins). Unknown until now are bacteriophage proteins with ability to degrade or breach the bacterial outer membrane (i.e., "BOMB" proteins), nor are any assays described to identify such proteins. The predicted peptide coding regions of the P15 putative holin, holZ (SEQ ID No. 27 in U.S. application Ser. No. 10/556,563 and PCT/US2004/015099) its endolysin, lysY (SEQ ID No. 26 in U.S. application Ser. No. 10/556,563 and PCT/US2004/015099), and its BOMB, bombBC (SEQ ID No. 82 in U.S. application Ser. No. 10/556,563 and PCT/US2004/015099) were amplified by polymerase chain reaction (PCR) from the P15 phage DNA and cloned in pGemT without promoters. These coding regions were operably fused with a repressible promoter in a modified pET27b expression vector system using *E. coli* strain BL21DE3 (Novagen). In the case of bombBC, two versions were created, one of them with, and the other without, a pelB leader sequence. This leader sequence assured export of bombBC across the inner membrane to the bacterial periplasm. Experiments were conducted to compare the effect of expression of these three genes in pET27b by comparison with the empty vector in liquid cultures. In addition, experiments were conducted to compare the effect of expression of the holin, holZ with the BOMB, bombBC, in BL21 DE3 cells that also constitutively expressed an endolysin gene, lysS. Cells were cultured on agar plates under glucose repression, and then grown in liquid culture medium without repression. Cells were then induced by addition of 1 mM IPTG and the optical density (OD) of the cultures at 600 nm were compared at different times after induction. Results are presented in Table 1 below.

Induced expression of the holin, HolZ, without the endolysin LysS, caused quasilysis; the optical density of the culture increased somewhat and then declined to the starting density. There was no evidence of cell debris in these cultures. By contrast, induced expression of HolZ with LysS caused immediate lysis, with obvious cell debris in the cleared lysate. These effects are characteristic of holins, which kill the cell by disrupting the inner membrane, but which cannot degrade the bacterial cell wall, and so cellular contents remain contained and there is no appearance of a lysate in the culture.

Induced expression of the endolysin, LysY, caused a slow reduction in cell density (not shown), and by contrast with the effects of HolZ expressed alone, cell lysis debris was apparent in these cultures. Since LysY was cloned without a leader sequence, this endolysin appeared to behave similarly to lysozyme, and exhibited some ability to penetrate or permeabilize the bacterial inner membrane, allowing it to reach and degrade the bacterial cell wall, causing lysis.

Induced expression of the BOMB protein BombBC caused quasilysis that looked similar to that caused by HolZ; the optical density of the culture increased somewhat and then declined to the starting density. There was also no evidence of cell debris in these cultures. However, and by contrast with HolZ combined with LysS, BombBC combined with LysS did not cause lysis, but rather BombBC combined with LysS appeared to have no lytic effect, indicating that the inner bacterial membrane was intact and LysS could not reach the periplasm and attack the cell wall. This strongly suggested that the activity of BombBC was qualitatively different from that of a holin, which breaches the inner membrane, or an endolysin, which degrades the murein or peptidoglycan cell wall.

In addition, berberine chloride, a commercially prepared, plant derived, antimicrobial compound (a "phytoalexin") worked synergistically with BombBC to reduce culture density. This synergistic effect was not seen with either a holin nor an endolysin. Berberine may be used to assay for defects in the LPS barrier and/or efflux pumping ability of phytopathogenic bacteria (Reddy et al., 2007). Bacteria are sensitive to berberine in a concentration dependent manner. Any berberine that leaks through the LPS must be actively pumped out (effluxed) for bacterial survival; if either the LPS is breached or the efflux pumps are disabled, bacteria are unable to grow in the presence of berberine. When berberine (5,6-dihydro-9,10-dimethoxybenzo-1,3-benzodioxoloquino-lizimium, an alkaloid DNA intercalating agent; Schmeller et al., 1997), was added (5 micrograms/10 to cells carrying bombBC and grown in liquid culture in these experiments, cell death was much more rapid when BombBC was expressed. Addition of berberine at the same concentration to BL21 DE3 cells carrying the pET vector alone had little effect. The synergistic effect of berberine with expressed BombBC demonstrated that BombBC acted on the outer membrane, or LPS protective layer, of the bacterial cells and suggested that berberine and other agents that must be actively effluxed from bacterial cells may be used as part of an additional gene expression assay to distinguish Bomb genes from other bacteriophage genes that kill bacterial cells upon expression (eg., endolysin and holin genes).

| | | 0 hr PI | 3 hr PI | 18 hr PI | 24 hr PI |
|---|---|---|---|---|---|
| BL21DE3/ pET vector only | Uninduced | 0.5 | 1.0 | 0.9 | 0.9 |
| | Induced | 0.5 | 0.9 | 0.8 | 0.8 |
| | Induced + berberine | 0.5 | 0.9 | 0.7 | 0.7 |
| BL21DE3/ P15 holZ (holin) | Uninduced | 0.6 | 1.0 | 1.0 | 1.0 |
| | Induced | 0.6 | 0.8 | .6 | .6 |
| | Induced + berberine | ND | ND | ND | ND |
| BL21DE3/ plysS/holZ (holin + endolysin) | Uninduced | 0.4 | 0.7 | ND | ND |
| | Induced | 0.4 | 0.1 | ND | ND |
| | Induced + berberine | ND | ND | ND | ND |
| BL21DE3/ bombBC (BOMB) | Uninduced | 0.5 | 1.0 | 0.8 | 0.8 |
| | Induced | 0.5 | 0.8 | 0.7 | 0.6 |
| | Induced + berberine | 0.5 | 0.6 | 0.5 | 0.4 |
| BL21DE3/ plysS/ bombBC (BOMB + endolysin) | Uninduced | 0.34 | 1.1 | 1.2 | 1.4 |
| | Induced | 0.34 | 0.8 | 0.35 | 0.4 |
| | Induced + berberine | ND | ND | ND | ND |

Table 1. Effect of expression of holin HolZ, endolysin LysY and BOMB BombBC genes cloned from phage P15 on growth of *E. coli* BL21 DE3 cells in liquid culture in the presence or absence of the phytoalexin berberine. PI, Post-Inoculation; ND, Not Determined.

Example 5

Use of P3rpoH::lacZ Reporter to Confirm Effect of BOMB Protein on Bacterial LPS

*E. coli* strains ADA410 carries a P3rpoH::lacZ reporter gene that is selectively activated when the LPS or outer membrane of the cells are damaged (Shapiro and Baneyx, 2002). The bombBC coding region was recloned into the pMAL expression vector (New England Biolabs, Ipswich, Mass.), overexpressed in *E. coli* BL21 DE3 cells, and purified (FIG. 1). Ten microliter droplets of the purified protein preparation were dropped onto a fresh suspension of ADA410 cells plated on LB agar containing 5-bromo-4-chloro-3-indolyl Beta-D-galactopyranoside (X-gal), along with resuspension buffer as a control. Blue color slowly developed and intensified over a 24 hr period of growth around the ADA410 cells, confirming a detrimental effect of BombBC on the bacterial LPS.

Example 6

Construction of BombBC Expression Cassettes in Plant Expression Vectors

The CaMV promoter from pBI221 (Clontech, Palo Alto, Calif.) was enzymatically recloned into the polylinker cloning site of pCAMBIA0390 (Cambia, Canberra, AU), which has a left T-DNA border, the polylinker site, a NOS transcriptional terminator and right T-DNA borders, creating pIPG700. The phage P15 bombBC gene was enzymatically recloned into pIPG700 downstream from the CaMV promoter and upstream from the NOS terminator, creating pIPG780. A 24 amino acid plant signal peptide derived from a protein known to accumulate in the citrus xylem, P12 (GenBank Accession # AF015782; Ceccardi et al., 1998) was used to create a xylem secretion signal leader (SEQ ID No. 3 and SEQ ID No. 4). The xylem secretion signal peptide sequence was amplified from *Citrus sinensis* (sweet orange) by PCR and cloned upstream of the bombBC gene and resulting in a translational gene fusion between P12 and BombBC (SEQ ID No. 5) on pIPG780. Clone pIPG780 was subsequently used for transient expression assays in the dicots: pepper, citrus and geranium.

The P12::BombBC gene (SEQ ID No. 5) was enzymatically recloned from pIPG780 into pCAMBIA1305.2 (Cambia, Canberra, AU), such that the gene was driven from the reverse CaMV promoter of pCAMBIA1305.2, forming pIPG787. pCAMBIA1305.2 carries the hygromycin resistance gene driven by a dual CaMV promoter for plant selection. The P12::BombBC (SEQ ID No. 5) gene was also enzymatically recloned from pIPG780 into pCAMBIA2301 (Cambia, Canberra, AU), such that the BombBC gene was driven from the reverse CaMV promoter of pCAMBIA2301, forming pIPG786.

pCAMBIA2301 carries the kanamycin resistance gene driven by a dual CaMV promoter for plant selection. pIPG786 was used for transformation and regeneration of tobacco and citrus, while pIPG787 was used for transformation of geranium and rice.

Example 7

Use of Transient Expression of bombBC in Sweet Pepper Plants to Demonstrate Enhanced Resistance to *Xanthomonas* and *Ralsionia*

For transient expression assays, the plant transformation and expression vector pIPG780 was moved into *A. tumefaciens* strain GV2260 by either electroporation or bacterial conjugation as described (Kapila et al., 1997). GV2260 carrying pIPG780 was used for transient expression in pepper and geranium plants as described (Kapila et al. 1997; Duan et al., 1999; Wroblewski et al. 2005). Cultures of *Agrobacterium* harboring the constructs of interest were grown in minimal medium in the presence of acetosyringone to induce the *Agrobacterium* vir genes. The optical density of the cultures was maintained at 0.008 for pepper and at 0.25 for geranium. Strain GV2260 carrying pIPG780 or empty vector control was first flooded into the apoplastic spaces of sweet pepper (*Capsicum*) leaves through open stomata by injection using a tuberculin syringe without a needle. An area of from 2 to 10 cm$^2$ of leaf was flooded and the area inoculated was then circled with a permanent marker. This was followed 3 days later by challenge inoculations within the previously inoculated area, again by syringe injection, this time with ca. 2×10$^6$ colony forming units (cfu) of either *X. pelargonii* strain CHSC or *R. solanacearum*, both grown overnight in liquid cultures. This gave an inoculum density of each pathogen of about $2 \times 10^4$ cfu/cm$^2$. Both strains used were published reference strains, confirmed pathogenic on their hosts: *X. pelargonii* attacks only geranium and causes bacterial blight disease of geranium, while *R. solanacearum* attacks primarily plants in the Solanaceae family (potato and tomato). Sweet pepper is a nonhost of both pathogens. (Plants that are attacked in nature are considered to be "hosts" of the indicated pathogens. All other plants are considered to be "nonhosts" of the indicated pathogens. When these same pathogens are inoculated at the indicated densities onto nonhost plants or onto host plants carrying certain resistance (R) genes, a rapid hypersensitive response (HR), is observed. The HR appears as a confluent, necrotic, collapsed zone at the inoculation site within 24-48 hrs.).

Results were assessed visually according to presence or absence of HR symptoms observed after 48 hrs. In all cases, a "split leaf" assay was used in which pIPG780 was inoculated on one half of the leaf and the empty vector control was inoculated on the other half of the same leaf. In repeated experiments; HR symptoms elicited on the control side of the inoculated leaf by either *X. pelargonii* or *R. solanacearum* were abolished in the presence of transiently expressed BombBC on pIPG780.

Due to the effects of BombBC in compromising the LPS barrier of *E. coli* to allow the phytoalexin berberine to penetrate and kill the bacterium in Example 4 and the indirect evidence of damaging the LPS barrier of *E. coli* in Example 5, we deduce that the native phytoalexins of pepper plants, in combination with the BombBC transiently expressed in pepper plants, killed or inhibited growth of both *Xanthomonas* and *Ralstonia*, thereby preventing the HR in these experiments.

Example 8

Use of Transient Expression of bombBC in Geranium (*Pelargonium* X *Hortorum*) Plants to Demonstrate Enhanced Resistance to *Ralstonia*

In order to determine if *Ralstonia* pathogens were also affected by BombBC expressed in host plants, as opposed to nonhost plants such as pepper, assays similar to those described in Example 7 above were performed, this time using Florists' geranium (*Pelargonium* X *hortorum*). This was done in order to confirm that the killing or disabling of this pathogen's ability to elicit an HR on nonhosts also extended to pathogens of susceptible host plants. Assays identical to those described in Example 7 were performed using florist's geranium plants, except that for these pathogenicity assays in a plant that is highly susceptible to disease from this pathogen, the results were examined daily for a period of from 2 to 7 days after challenge inoculation. Again, the results were similar to those described for the HR in Example 7. Pathogenic symptoms caused by *X. pelargonii* were greatly reduced when pIPG780 was used. In addition, cell counts taken from these regions demonstrated a 100× drop in the number of colony forming units in plant leaves expressing BombBC vs. control leaves. These results confirmed and extended the concept that BombBC can be expressed in plants for the purpose of killing or disabling Gram-negative pathogenic bacteria to include host plants, most likely due to the combined effects of native phytoalexins produced by the host plant and transient expression of BombBC to disable the LPS barrier of the pathogen.

Example 9

Use of Transient Expression of bombBC in Citrus Plants to Demonstrate Enhanced Resistance to *Xanthomonas citri*

In order to determine if *Xanthomonas* pathogens were also affected by BombBC expressed in host plants, as opposed to nonhost plants such as pepper, assays similar to those described in Examples 7 and 8 above were performed, this time using grapefruit (*Citrus paradisi*) plants inoculated with *X. citri*, causal agent of citrus canker disease. This agent is a regulated pathogen, and such inoculations had to be performed under strict quarantine.

These experiments were done in order to confirm that the degradation or breaching of the LPS of *Xanthomonas* and subsequent killing of the pathogen, affecting its ability to elicit an HR on nonhosts also extended to pathogens of susceptible host plants. Assays identical to those described in Examples 7 and 8 were performed using citrus, except that for these pathogenicity assays in a plant that is highly susceptible to disease from this pathogen, the results were examined daily for a period of from 6 to 14 days after challenge inoculation. Again, the results were similar to those described for the HR in Example 7 or the pathogenic reaction in Example 8. Pathogenic symptoms caused by *X. citri* were greatly reduced when pIPG780 was used. These results confirmed and extended the concept that BombBC can be expressed in plants for the purpose of killing or disabling Gram-negative pathogenic bacteria to include host plants, most likely due to the combined effects of native phytoalexins produced by the host plant and transient expression of BombBC to disable the LPS barrier of the pathogen.

Example 10

Creation of Transgenic Geranium (*Pelargonium* X *Hortorum*) Using bombBC

Figure 2:
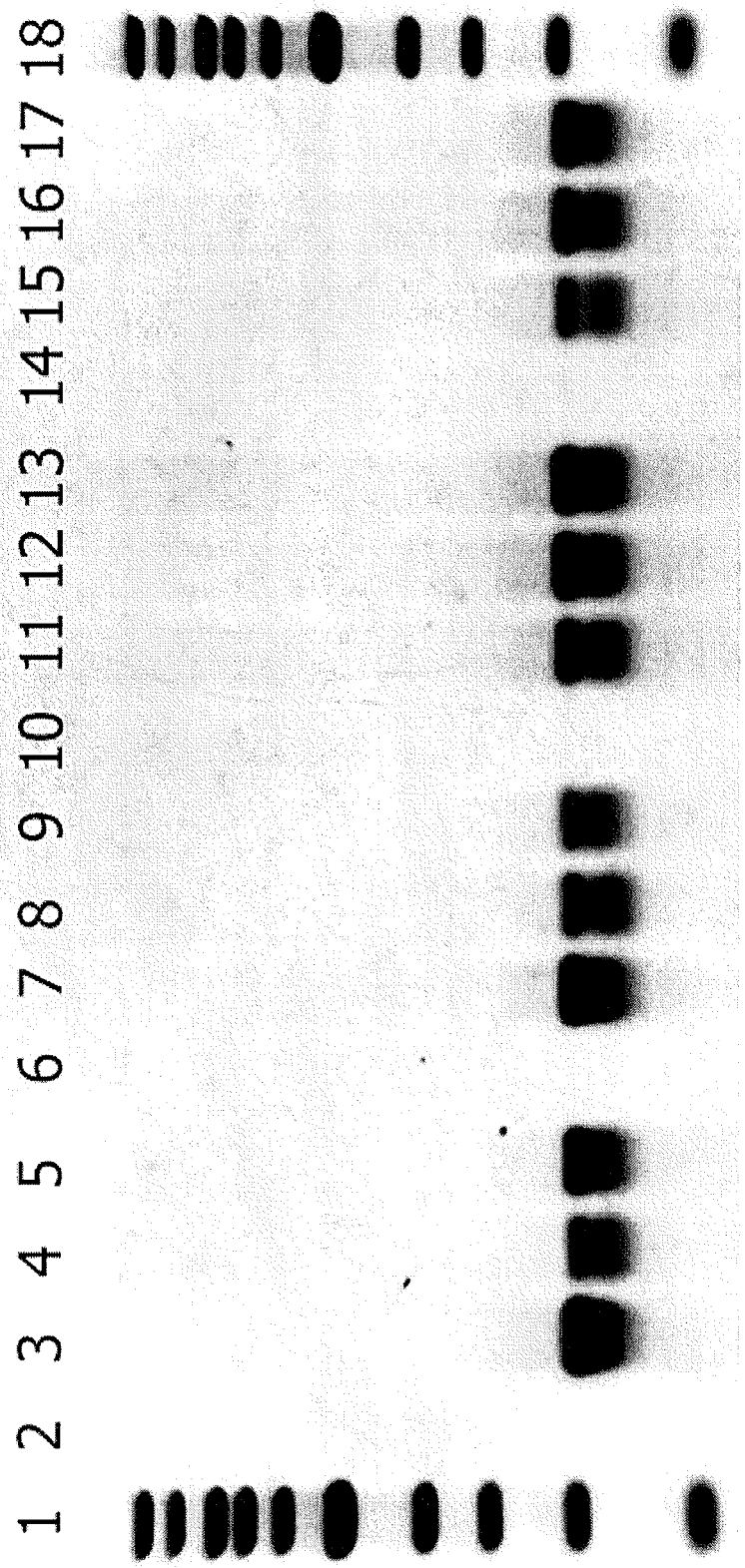
FIG. 2 shows PCR confirmation of transformation of four plant species using bombBC, including 3 plants each of Florist's geranium (*Pelargonium* X *hortorum*) cv. Avenida (Lanes 3, 4, 5), citrus (*Citrus sinensis* x *Poncirus trifoliata*) cv. Carizzo, tobacco (*Nicotiana tobacum*) cv. *Xanthi*, and rice (*Oryza sativa japonica*) cv. TP309. Lane 1, 1 kb DNA ladder; 2, nontransgenic Avenida control; 3, Av250; 4, Av386; 5, Av387; 6, nontransgenic Carizzo control; 7, C12; 8, C17; 9, C18; 10, nontransgenic *Xanthi* control; 11, X473; 12, X480; 13, X901; 14, nontransgenic TP309 control, 15, TP147; 16, TP170; 17, TP192; 18, 1 kb DNA ladder. PCR primers used were IPG872 (5'-tca gcc act cga tgc cgt c) and IPG911 (5'-gca cga ttc aag agt agg). The expected PCR product in all cases is 974 bp.

Transgenic geranium (*Pelargonium* X *hortorum*) cv. Avenida were created using *Agrobacterium tumefaciens* and *Rhizobium* spp. using bombBC gene cloned into pIPG787. The most efficient methods for production of transgenic geraniums were achieved using either *A. tumefaciens* (Robichon et al., 1995. Approximately 9% PCR positive geranium petiole explants were confirmed (of the 360 total petioles subjected to the transformation protocols. A total of 33 transgenic geranium were obtained, based on PCR amplification of the bombBC gene (FIG. 2). Selected plants were asexually reproduced and challenge inoculated with different pathogens as described below. These results demonstrated that the bombBC gene, shown to be expressed in transient expression assays, could be stably transformed and presumably expressed in geraniums at efficiencies equivalent to those obtained using empty vector or another gene construct, indicating that BombBC was not detrimental to geranium plants.

Example 11

Creation of Transgenic Tobacco (*Nicotiana Tabaccum*) Using bombBC

Transgenic *Nicotiana tabaccum* cv. Xanthi plants were created using *Agrobacterium tumefaciens* and *Rhizobium* spp. using the bombBC gene cloned into pIPG786. The most efficient methods for production of transgenic tobacco were achieved using the leaf disc method with *A. tumefaciens* as described (Horsch et al. 1985). Transformants were selected on MS media (Murashige and Skoog 1962) containing kanamycin at 100 µg/ml. Approximately 21% PCR positive tobacco explants were confirmed (of the 235 total leaf discs subjected to the transformation protocols. A total of 50 transgenic tobacco plants were obtained, based on PCR amplification of the bombBC gene FIG. 2). Selected plants were both sexually and asexually reproduced and challenge inoculated with different pathogens as described below. These results demonstrated that the bombBC gene, shown to be expressed in transient expression assays, could be stably transformed and presumably expressed in tobacco at efficiencies equivalent to those obtained using empty vector or another gene construct, indicating that BombBC expression was not detrimental to tobacco plants.

Example 12

Creation of Transgenic Citrus (*Citrus sinensis* x *Poncirus trifoliata*) Using bombBC Transgenic citrus (*Citrus sinensis* x *Poncirus trifoliata*) cv. Carizzo plants were created using *Agrobacterium tumefaciens* and *Rhizobium* spp. using bombBC gene cloned into pIPG786. The most efficient methods for production of transgenic citrus were achieved using *A. tumefaciens* applied to etiolated citrus stem sections as described (Moore et al., 1992). Approximately 6% PCR positive citrus stem explants were confirmed (of the 650 total stem sections subjected to the transformation protocols. A total of 40 transgenic citrus plants were obtained, based on PCR amplification of the bombBC gene (FIG. 2). Selected plants were asexually reproduced and challenge inoculated with different pathogens as described below. These results demonstrated that the bombBC gene, shown to be expressed in transient expression assays, could be stably transformed and presumably expressed in citrus at efficiencies equivalent to those obtained using empty vector or another gene construct, indicating that BombBC was not detrimental to citrus plants.

Example 13

Creation of Transgenic Rice (*Oryza sativa Japonica*) Using bombBC

Transgenic rice (*Oryza sativa japonica*) cv. TP309, were created using *Agrobacterium tumefaciens* and *Rhizobium* spp. using bombBC gene cloned into pIPG787. The most efficient methods for production of transgenic rice were achieved using *A. tumefaciens* applied to rice callus produced from seed as described (Hiei et al., 1997). Approximately 20% PCR positive rice explants were confirmed (of the 305 total number of calli subjected to the transformation protocol. A total of 60 transgenic rice plants were obtained, based on PCR amplification of the bombBC gene. Selected plants were sexually reproduced and challenge inoculated with different pathogens as described below. These results demonstrated that the bombBC gene, shown to be expressed in transient expression assays, could be stably transformed and presumably expressed in rice at efficiencies equivalent to those obtained using empty vector or another gene construct, indicating that BombBC was not detrimental to rice plants.

Example 14

Use of Asexually Reproduced Progeny of Transgenic Geranium, Citrus and Tobacco Plants to Obtain Cloned bombBC Plants Transgenic geranium, citrus and tobacco plants were obtained as set forth in Examples 10, 11 and 12. The transgenic geranium, citrus and tobacco plants were asexually propagated to produce progeny clones using techniques well known to one skilled in the art of geranium, citrus or tobacco propagation. For geranium, tobacco and other vegetative species that are normally propagated by taking cuttings, an internode with two nodes are cut from a mother plant and rooted, normally using a support medium, with or without root inducing hormones, producing a single new plant for each such clone or "cutting". The cuttings were in all cases genetically identical to the mother plant (i.e., 100% PCR positive for BombBC). For citrus and similarly propagated woody species, a "scion" cutting is taken from a transgenic stem section with leaves and grafted or spliced onto a nontransgenic rootstock, such that the roots and lower main stem are comprised of the nontransgenic rootstock, while the upper main stem and shoots are comprised of the transgenic scion. The scion cuttings were in all cases genetically identical to the mother plant (i.e., 100% PCR positive for BombBC); the genetic modifications performed in the mother plant were stable. These results demonstrated that the genetic modifications performed in the mother plant were stable through at least one asexual generation.

Example 15

Use of Sexually Reproduced Progeny of Transgenic Rice and Tobacco Plants to Obtain Cloned bombBC Plants Transgenic diploid rice and tobacco plants were obtained as set forth in Examples 11 and 13. The transgenic ($T_0$ generation) rice and tobacco plants were self-pollinated and the seed ($T_1$ generation) was harvested from the self-pollinated plants, processed, planted, and progeny plants grown from the self-pollinated-seed. PCR assays were used to determine that the $T_1$ progeny plants all had a classical genetic 3:1 ratio, wherein ¾ of the plants (¼ homozygous transgenic and ½ heterozygous transgenic plants) were found to be transgenic by PCR tests, and ¼ of the plants were nontransgenic. These tests showed that that the introduced nucleic acid molecules encoding bombBC were stably integrated into both rice and tobacco using the methods of the present invention and that bombBC was also heritable.

Example 16

Use of BombBC Expressed in Transgenic Geranium (*Pelargonium* X *Hortorum*) Host Plants to Confer Resistance to *Xanthomonas Pelargonii* and *Ralstonia Solanacearum*

Pathogen challenge inoculations of transgenic Florist's geranium (*Pelargonium* X *hortorum*) plants expressing active BombBC and of asexually propagated Florist's geranium plants expressing active BombBC were conducted using *X. pelargonii* and *R. solanacearum*. The transgenic parental or asexually produced progeny clones obtained from the transgenic parental plants reduced disease symptoms.

Figure 3:
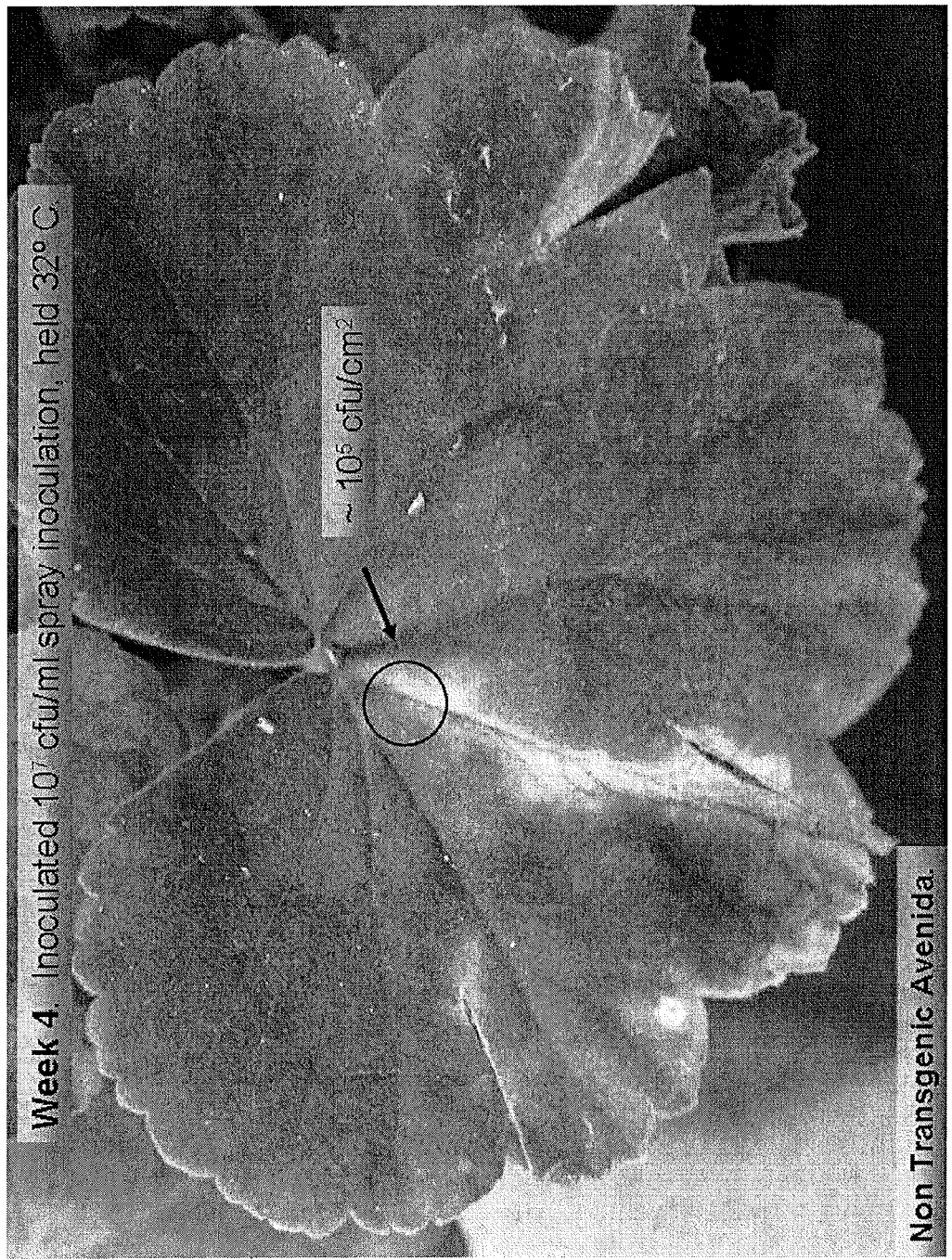
FIG. 3 shows typical symptoms of bacterial blight on a nontransgenic Florist's geranium (*Pelargonium* X *hortorum*) cultivar "Avenida" leaf inoculated with X *pelargonii* cells sprayed on the leaves at a concentration of $10^7$ colony forming units per milliliter (cfu/ml) and also inoculated using scissors dipped in $10^9$ cfu/ml of *X. pelargonii* cells to clip the leaves in several places. Following inoculation, plants were held at 32° C. The circled region was cut out, and contained ca. $10^5$ cfu/cm$^2$ live *X. pelargonii* cells (for details, refer Example 11 below). Photo taken four weeks after inoculation.
Figure 5:
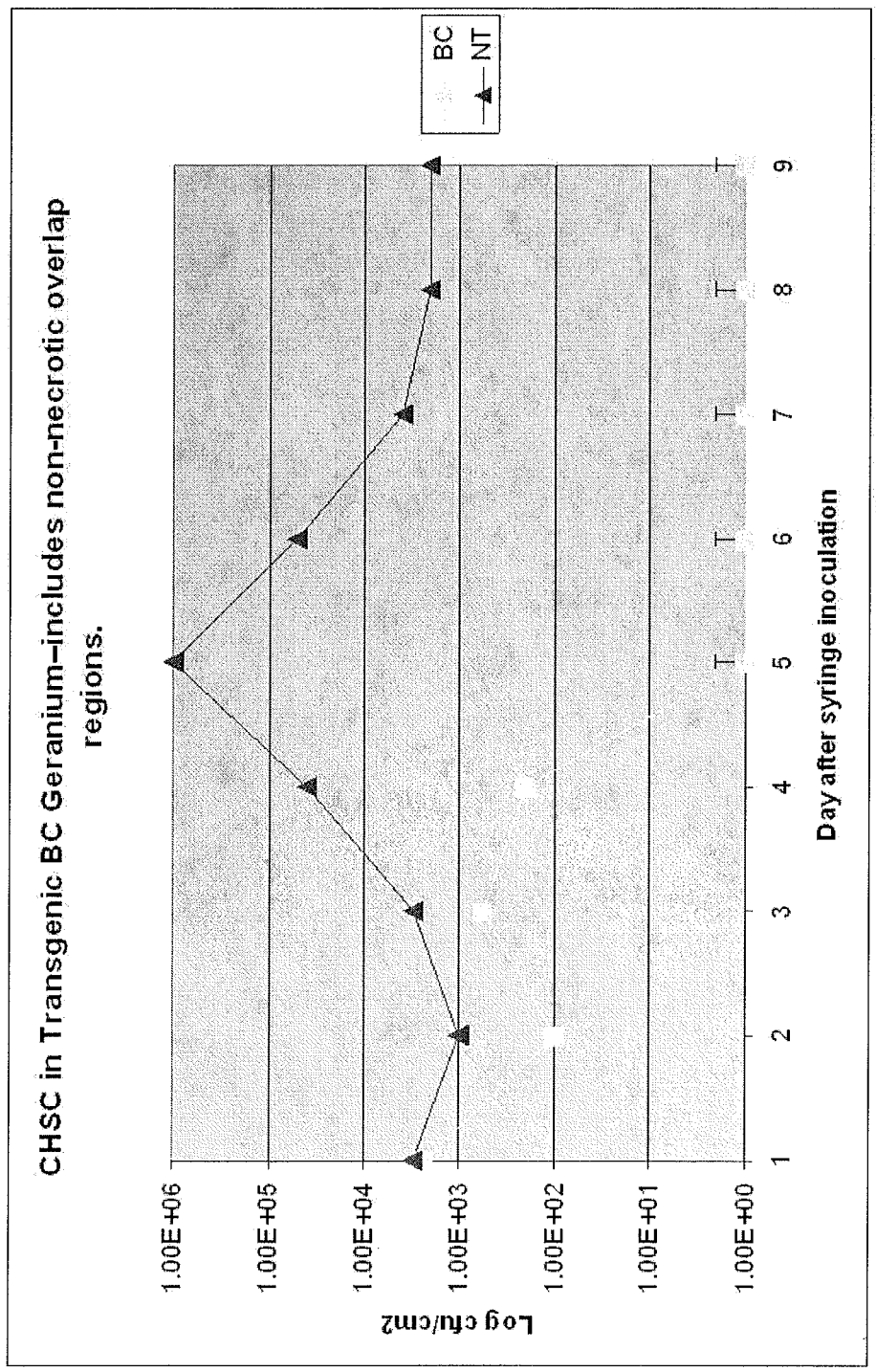
FIG. 5 shows growth of *X. pelargonii* strain CHSC inoculated on nontransgenic geranium (*Pelargonium* X *hortorum*) variety "Avenida" and rapid death of strain CHSC inoculated on transgenic variety "Avenida" expressing BombBC. Cell counts were taken daily for nine days by removing circular sections totaling 1 square centimeter (cm$^2$) using a cork borer from three inoculated leaves in the area most likely to contain pathogen cells (refer FIGS. 1 and 2). These leaf sections were macerated with a mortar and pestle and 1 milliliter of buffer, diluted using a 1:10 dilution series and 10 microliter drops placed on solid growth medium for counting. Consistently, a maximum cell density of $10^6$ cfu/ml of *X. pelargonii* was achieved in nontransgenic geranium variety "Avenida" plants after five days, and symptoms progressed steadily and systemically until the entire plant was dead, usually by 12 weeks after inoculation. However, no living *X. pelargonii* cells were recovered from transgenic geranium variety "Avenida" plants after five days following inoculation (FIG. 3), and there was no evidence of symptoms of geranium blight caused by *X. pelargonii*. These plants were both immune to *X. pelargonii* infection, and rapidly brought the artificially inoculated pathogen population to extinction.

Inoculations were performed using liquid culture grown *X. pelargonii* cells, sprayed on the leaves at a concentration of $10^7$ colony forming units per milliliter (cfu/ml) each. *X. pelargonii* was also inoculated using scissors dipped in $10^9$ cfu/ml of cells to clip the leaves in several places on the same plants that were sprayed. Following *X. pelargonii* inoculation, plants were held at 32° C. to encourage pathogen growth and symptom development. Four weeks after inoculation, photographs were taken of both nontransgenic geranium variety "Avenida" inoculated with *X. pelargonii* (FIG. 1) and transgenic geranium of the same variety "Avenida" expressing BombBC inoculated with *X. pelargonii* (FIG. 2), and circular sections totaling 1 square centimeter ($cm^2$) were removed using a cork borer from three inoculated leaves in the area most likely to contain pathogen cells (refer FIGS. 1 and 2). Consistently, $10^5$ cfu/ml of *X. pelargonii* was recovered from nontransgenic geranium variety "Avenida" plants at four weeks after inoculation (FIG. 3), and symptoms progressed systemically until the entire plant was dead, usually by 12 weeks after inoculation. However, no living *X. pelargonii* cells were recovered from transgenic geranium variety "Avenida" plants after five days following inoculation (FIG. 3), and there was no evidence of symptoms of geranium blight caused by *X. pelargonii*. These plants were immune to *X. pelargonii* infection.

Figure 4:
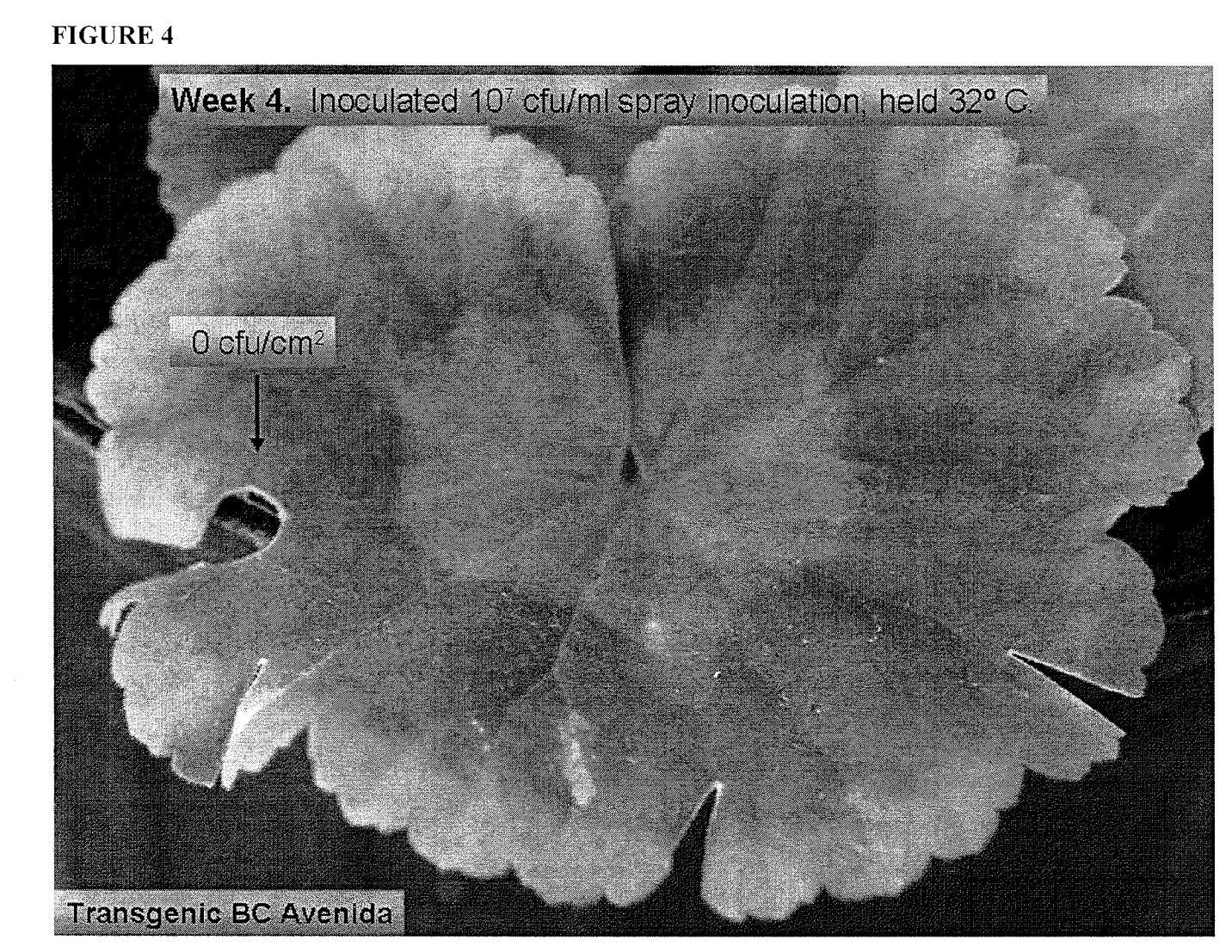

In separate experiments, *R. solanacearum* strain Rsp673, originally isolated from geranium and known to be strongly pathogenic to geranium, was inoculated by syringe infiltration of $10^6$ cfu/ml directly into the spongy mesophyl of leaves using the blunt end of a tuberculin syringe. In addition, these same syringe inoculated plants were also inoculated by adding 5 ml of a liquid culture containing $10^7$ cfu/ml of cells directly to the soil of the potted geranium plants (refer FIG. 4). Following inoculation, plants were held at 32° C. to encourage pathogen growth and symptom development. Symptoms on transgenic BombBC geranium variety "Avenida" plants inoculated with *R. solanacearum*, causal agent of bacterial wilt, failed to progress past the leaf area where the pathogen was directly infiltrated and the disease never became systemic. In addition to suppressing disease, BombBC expression evidently killed the pathogen, since there were no detected *R. solanacearum* cells twelve weeks after inoculation of *R. solanacearum* on transgenic BombBC "Avenida" plants. By contrast, symptoms on nontransgenic "Avenida" plants progressed normally and systemically; by twelve weeks after inoculation of *R. solanacearum*, all nontransgenic "Avenida" plants had died from wilt disease caused by this pathogen (FIG. 4).

These tests confirm that the introduced nucleic acid molecules coding for the BombBC protein have been stably integrated into geranium using the methods of the present invention, and demonstrate that transgenic geraniums, whether vegetatively propagated or not, are resistant or immune from disease caused by *X. pelargonii* and *R. solanacearum*.

These results further demonstrate that transgenic geraniums, whether vegetatively propagated or not, kill *X. pelargonii* and *R. solanacearum* cells. These results also confirm and extend the demonstration of disruption of the LPS of Gram-negative bacteria generally, as anticipated from tests of cells grown in culture and that such LPS disruption results in resistance to disease as anticipated from transient expression assays.

Example 17

Use of BombBC Expressed in Transgenic Tobacco Host Plants to Confer Resistance to *Ralstonia solanacearum*

Pathogen challenge inoculations of transgenic tobacco (*Nicotiana tabaccum* cv. *Xanthi*) plants expressing BombBC were conducted using *R. solanacearum*. Both sexually propagated (seeded, T1 generation from Example 15; Exp 3 in Table below) and asexually propagated (cuttings, T0 generation from Example 11; Exp. 1 and 2 in Table below)) tobacco plants were inoculated and compared, since the method of asexual propagation provides a healed over, but still significantly enlarged cut surface beneath the soil line that might facilitate entry by the soil-born pathogen.

*R. solanacearum* strain Rsp446, strongly pathogenic to tobacco, was In inoculated by adding 5 ml of a liquid culture containing $5×10^7$ to $2×10^8$ cfu/ml of cells directly to the soil of the potted tobacco plants. Following inoculation, plants were held at 32° C. to encourage pathogen growth and symptom development. Plants were examined daily and wilted plants exhibiting black vein symptoms were noted and discarded. The results, recorded as number of survivors/total tested, after 68 days were as follows:

|  | Inoculum level | Control Cutting | Control Seeded | BombBC Cutting | BombBC Seeded |
|---|---|---|---|---|---|
| Exp. 1 | $5 × 10^7$ | 7/19 (37%) |  | 10/15 (63%) |  |
| Exp. 2 | $1 × 10^8$ | 4/20 (20%) |  | 9/20 (45%) |  |
| Exp. 3 | $2 × 10^8$ |  | 9/24 (38%) |  | 0/21 (100%) |

These results demonstrated that BombBC provided resistance to tobacco against *R. solanacearum*, and was 100% effective in seeded tobacco. These results, combined with the results from transgenic geraniums against two different pathogenic genera in Example 16, confirm the utility of using BombBC to control disease, not just in geraniums, but in transgenic plants generally.

Example 18

Use of BombBC Expressed in Transgenic Citrus and Tobacco Host Plants to Confer Resistance to Candidatus Liberibacter *Asiaticus*

Citrus greening disease, or Huanglongbin, is caused by Ca. Liberibacter *asiaticus*. This uncultured bacterial pathogen is a USDA Select Agent. It is known to attack tobacco plants, which may be used as a proxy host to test genes for resistance against the bacterium in transgenic tobacco (Francischini et al., 2007). *Cuscuta* spp. (dodder) was used to transmit greening from a known positively infected source, a sweet orange plant, to each of 6 healthy plants of *Nicotiana tabacum* L. cv. *Xanthi*. Two of the tobacco plants were transgenic for BombBC (created using the methods of Examples 11 and 15) and the other four were controls. The tobacco plants were allowed to remain connected to dodder for 4 weeks, and the plants were assayed for greening by nested PCR as described (Zhou et al., 2007). Results were that three of the four control plants became symptomatic for greening and all three were PCR positive), and that neither of the two transgenic BombBC plants became symptomatic and neither were PCR positive. These plants were held for three weeks, and retested. The results were the same, and indicated that BombBC provides resistance against citrus greening disease.

Similar tests were performed using six healthy citrus Carrizo plants. Again, *Cuscuta* spp. (dodder) was used to transmit greening from a known positively infected source, a sweet orange plant, to each of 6 healthy plants of *Citrus sinensis* x *Poncirus trifoliata* cv. Carizzo. Two of the citrus plants were transgenic for BombBC (created using the methods of Example 12) and the other four were controls. The citrus plants were allowed to remain connected to dodder for 4 weeks, and the plants were assayed for greening by nested PCR as described (Zhou et al., 2007). Results were that none of the Carrizo plants became symptomatic for greening and only one control plant became PCR positive, and that neither of the two transgenic BombBC plants became PCR positive. These plants were held for three weeks, and retested. The results were the same, and again indicated that BombBC provides resistance against citrus greening disease Example 19

Figure 7:
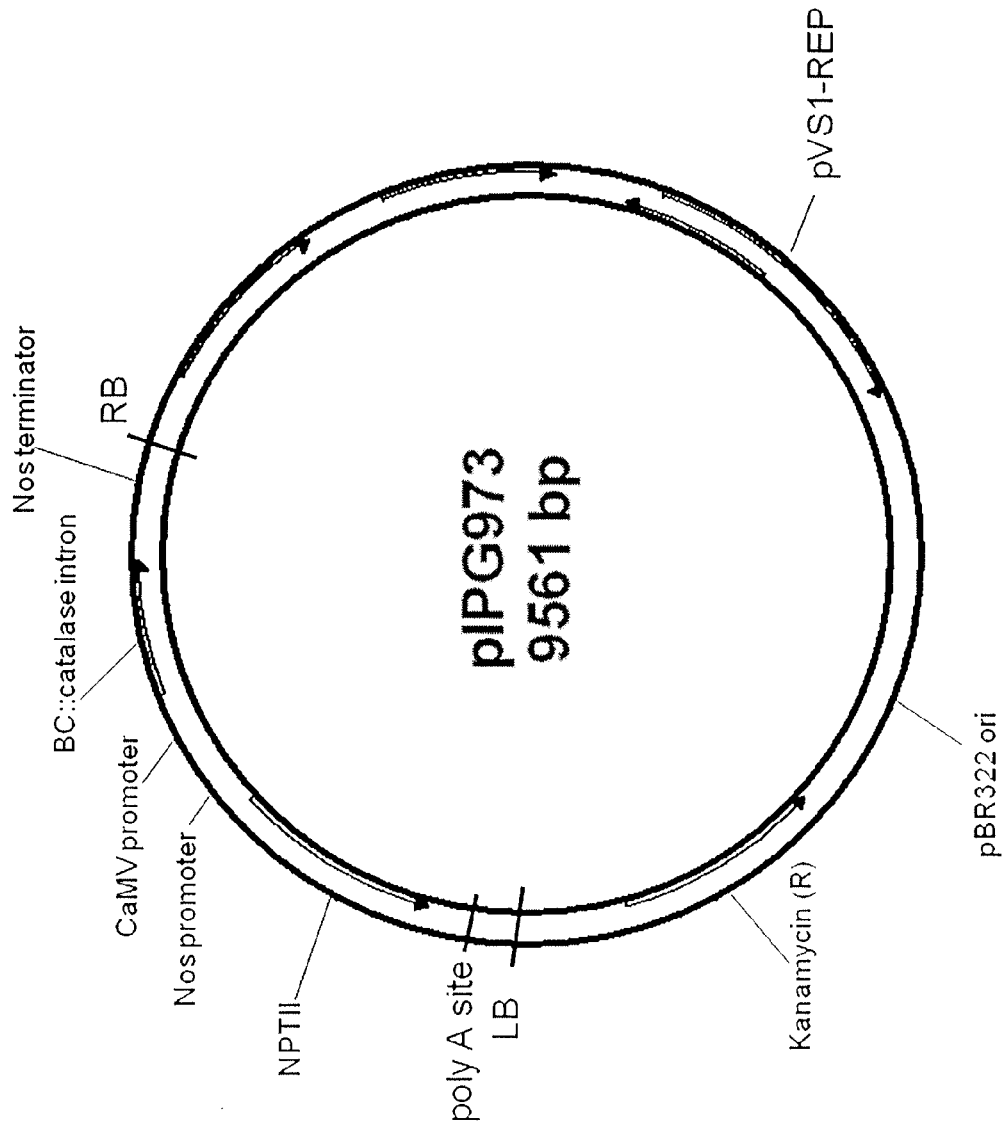
FIG. 7 shows a map of pIPG973 (SEQ ID No. 1) ill infecting. This is accomplished by a series of infection assays and overlay assays. Finally, phage nucleic acid is isolated and treated with DNAse and separately with RNAse using methods known to those skilled in the art. Only DNA based phage are selected.

Use of BombBC Expressed in Transgenic Citrus Host Plants to Confer Resistance to Citrus Canker Disease Six healthy Citrus sinensis x Poncirus trifoliata) cv. Carizzo plants were inoculated by dipping the entire top three inches of the 9-12 inch tall plants into a solution containing 200 ppm Silwet L-77 and *Xanthomonas citri* at $10^5$ cfu/ml. Symptoms on all plants appeared two weeks later, and were allowed to develop for four additional weeks. Two of the citrus plants were transgenic for BombBC (created using the methods of Example 12) and the other four were controls. Pathogenic symptoms caused by *X. citri* were greatly reduced in the two BombBC transgenic plants, both in terms of numbers of pustules (many fewer appeared in the BombBC plants) and in the size of the pustules (pustules remained tiny and were much less well developed in the BombBC plants).

These results confirmed and extended the concept that BombBC can be expressed in plants for the purpose of killing or disabling Gram-negative pathogenic bacteria to include host plants, most likely due to the combined effects of native phytoalexins produced by the host plant and expression of BombBC to compromise the LPS barrier of the pathogen.

Example 20

Use of Transgenic Rice Plants to Express Enzymatically Active BombBC

Transgenic rice plants expressing BombBC were created using *Agrobacterium tumefaciens* (Hiei et al., 1997) carrying the bombBC gene cloned into pIPG787. It is anticipated that these plants will be resistant to Gram-negative bacterial pathogens, including *X. oryzae* and *X. oryzicola*.

Example 21

Method of Using Bomb Proteins Expressed in Transgenic Plants to Extend the Shelf-Life of Cut Flowers We anticipate that Bomb proteins, when produced in transgenic plants that are typically marketed as cut flowers, such as roses, carnations, chrysanthemums, gladiolas, etc., will enhance longevity of the cut transgenic flowers by suppressing bacterial growth in the vase water caused by opportunistic or soft-rotting bacteria such as *Erwinia carotovora* and *Erwinia chrysanthemi*. Transgenic plants that will later be marketed as cut flowers will be produced by methods described in the above examples.

Example 22

Method of Using Bomb Proteins as an Additive to Extend the Shelf Life of Cut Flowers and Animal Feed We anticipate that Bomb proteins, possibly in combination with lytic proteins, when added to the vase or shipping container water of nontransgenic plants that are typically marketed as cut flowers, such as roses, carnations, chrysanthemums, gladiolas, etc., will enhance longevity of the cut transgenic flowers by suppression of fungal and bacterial growth in the vase water. Typical microbial species that shorten the shelf life of cut flowers are *Erwinia carotovora* and *Erwinia chrysanthemi*. For example, we anticipate that adding a dried protein to water used to sustain cut flowers will result in a longer shelf-life for the cut flowers when compared to cut flowers sustained in water from the same source without the addition of the dried protein.

The Bomb proteins will most likely be produced in transgenic plants. Crude extracts of protein will be harvested, and either dried using a granular additive or suspended in an appropriate liquid and packaged. In another example, when the dried protein is added to animal feed, it will control microbial contamination, including those microbes that may cause food poisoning. A dry or liquid preparation of Bomb proteins could be added to animal feed during factory preparation or afterwards by the animal owner by mixing. Either way, the result will be a longer shelf life of the feed and reduced opportunity for growth of microbes that can result in food poisoning.

Example 23

Method of Using Bomb Proteins in Transgenic Plants to Control Gram-Negative Bacteria, Whether Disease Agents of Plants or not We anticipate that when transgenic plants producing Bomb proteins, possibly in combination with production of a lytic protein, are planted in field situations, they will exhibit resistance not only to Gram-negative bacterial diseases of said plants through killing or inhibiting growth of these Gram-negative bacteria, but also they will kill or inhibit growth of Gram-negative bacteria such as *E. coli, Shigella* spp. and *Salmonella* spp. that may infect said plants, but without causing plant disease. Such transgenic plants may become part of a food security program aimed at reducing the possibility of spread of human diseases by food supply contamination. Resistance in all cases is anticipated to be achieved through the combined action of natural defense compounds produced by the transgenic plants and the Bomb proteins, together with any lytic enzymes produced by the transgenic plants.

Example 24

Binary Transformation Vectors

Binary transformation vectors were constructed using standard molecular techniques known to those skilled in the art. Plasmid constructs pIPG955 (U.S. application Ser. No. 13/594,728) and pIPG980 were made for use in *Sinorhizobium* strains. Plasmid constructs pIPG924 (see U.S. patent application Ser. No. 13/594,728) and pIPG973 (refer FIG. 7 and SEQ ID 1) were made for use in *Agrobacterium* strains. All constructs are based on pCAMBIA2301 (Cambia, Canberra, Australia), and all carry both a pVS1 wide host range replication origin and a pBR322 replication origin for high copy maintenance in *E. coli*. pIPG924 was constructed by first replacing the double 35S promoter of pCAMBIA2301 with the nopaline synthase (nos) promoter which was used to drive the neomycin phosphotransferase gene (nptII) gene, which confers resistance to kanamycin, for selection in plants. The 35S::GUS gene was then replaced with the virus coat protein controller element from Beet Yellows Closterovirus (BYV), from nucleotides 13499-13637 (Peremyslov et al., 1999), operationally fused to the codon optimized, antibacterial, bombBC (renamed as "BC" throughout the following text) gene interrupted with the catalase intron (SEQ ID 2; see U.S. Pat. No. 7,919,601 and PCT/US08/70612, which are incorporated by reference herein). pIPG973 was constructed by replacing the BYV promoter of pIPG924 with a single 35S promoter.

pIPG955 was constructed similarly to pIPG924, with the double 35S promoter of pCAMBIA2301 replaced with the nos promoter to drive the nptII gene for selection in plants, followed by replacing the GUS gene with a BC::intron fragment and with a glycine rich peptide (GRP) leader, operationally driven by the single 35S promoter. In addition, the kanamycin resistance gene used for selection in bacteria was replaced with a spectinomycin resistance gene fragment from pCAMBIA1105 for use in *Sinorhizobium* strains carrying pTWBi3. pIPG980 was constructed by replacing the bacterial kanamycin resistance gene in pIPG973 (refer FIG. 7 and SEQ ID 1) with the spectinomycin resistance gene. fragment from pCAMBIA1105.

Figure 8:
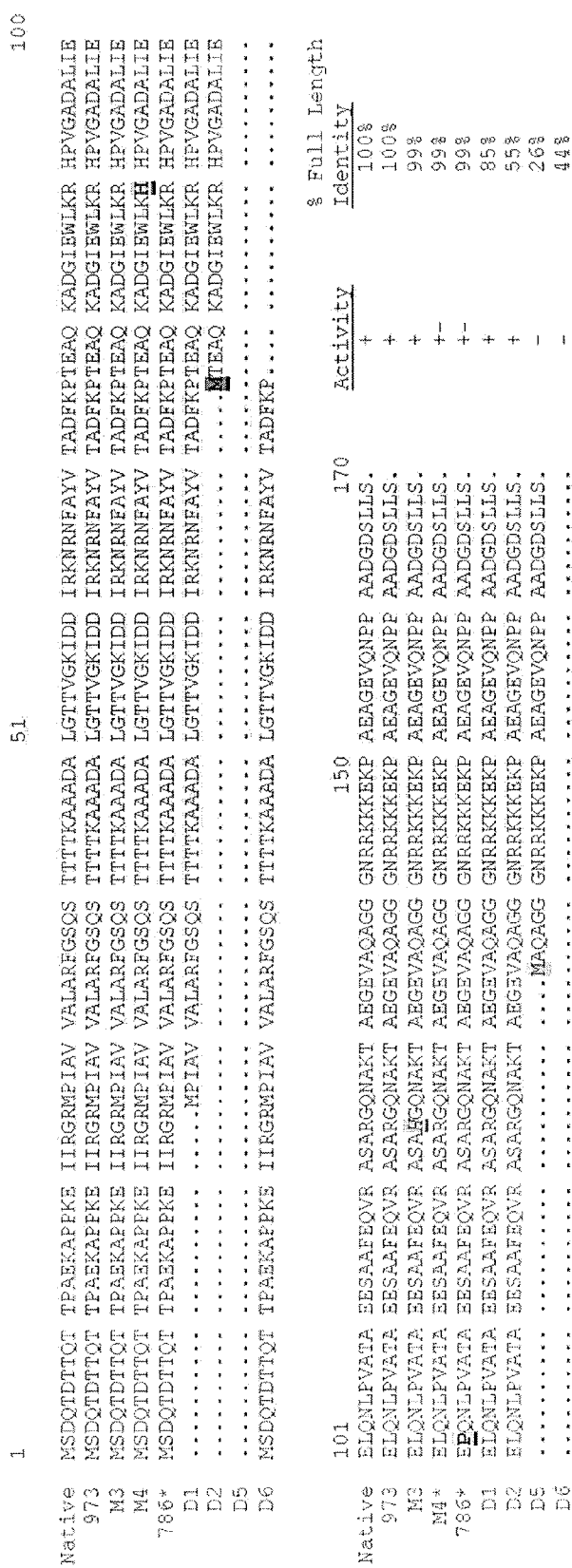
Figure 9:
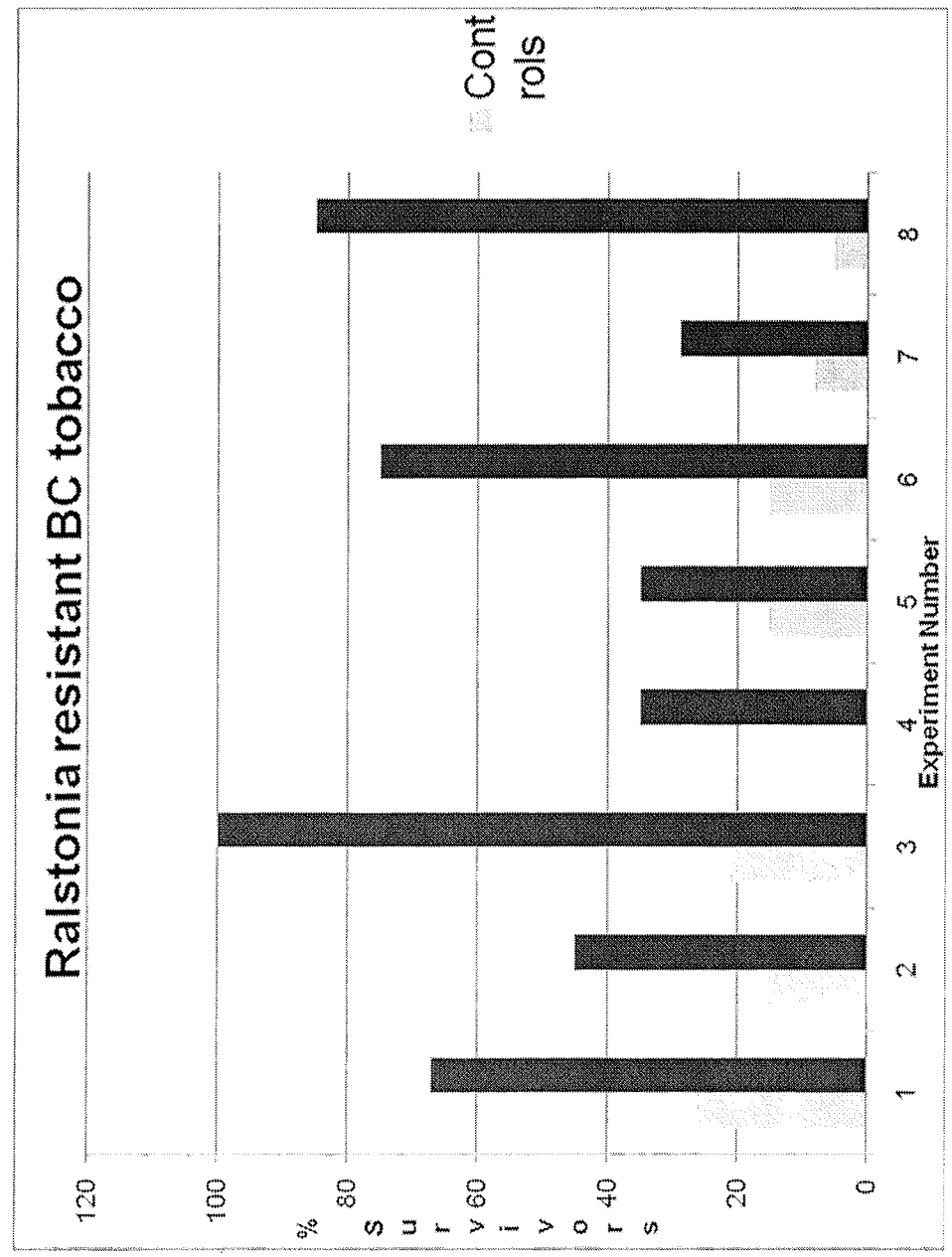
Figure 10:
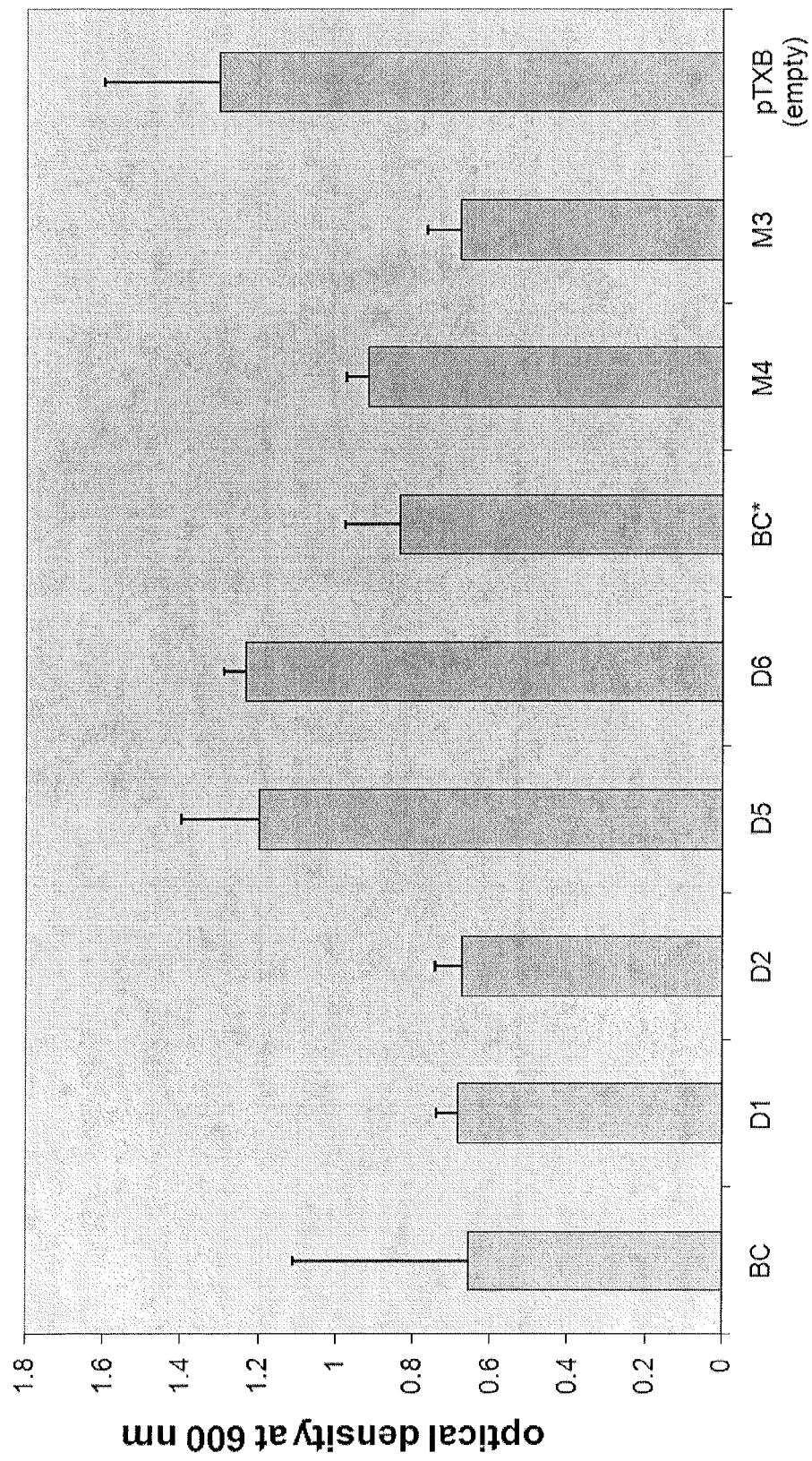
Figure 11:
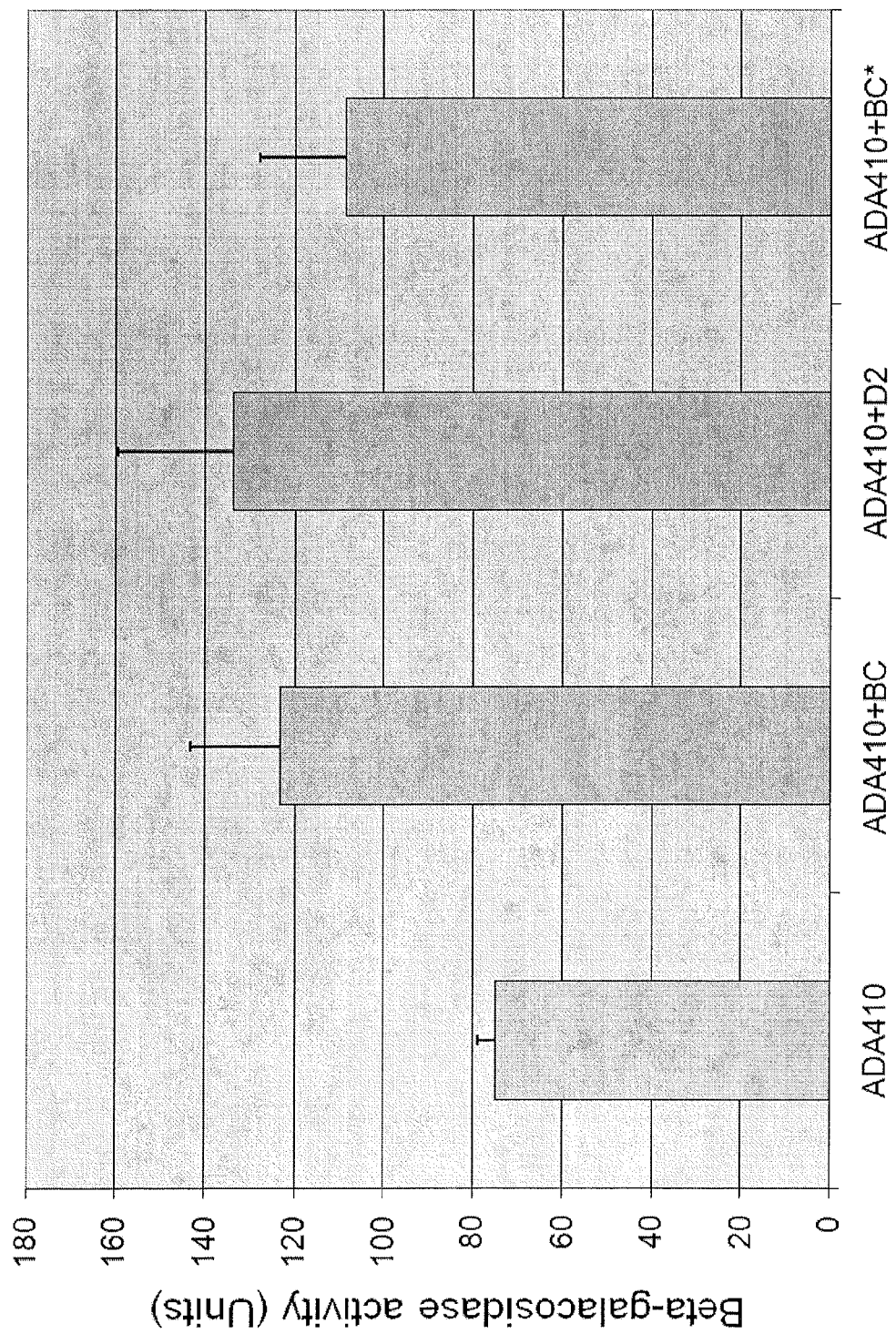
Figure 12:
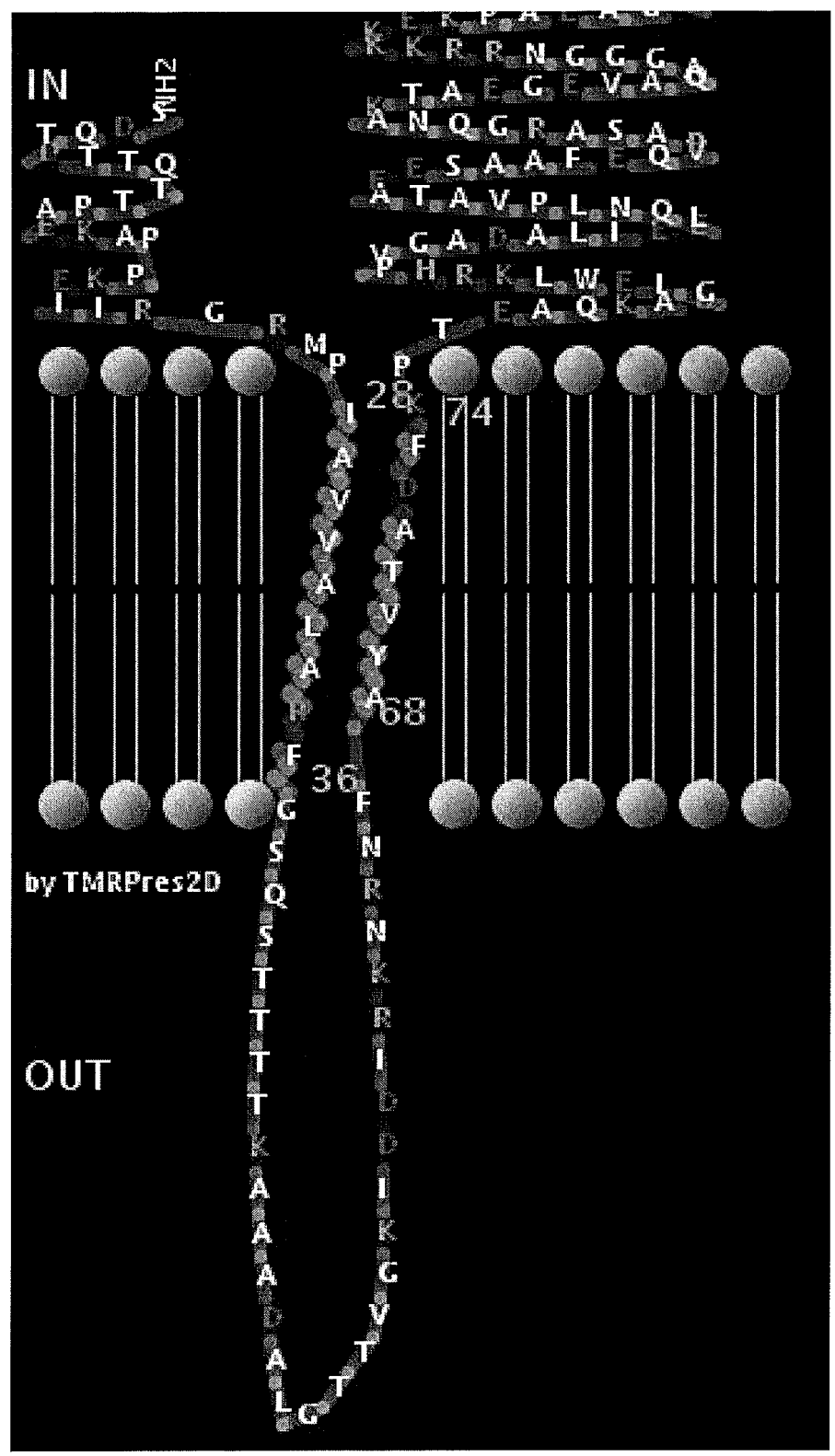
Figure 13:
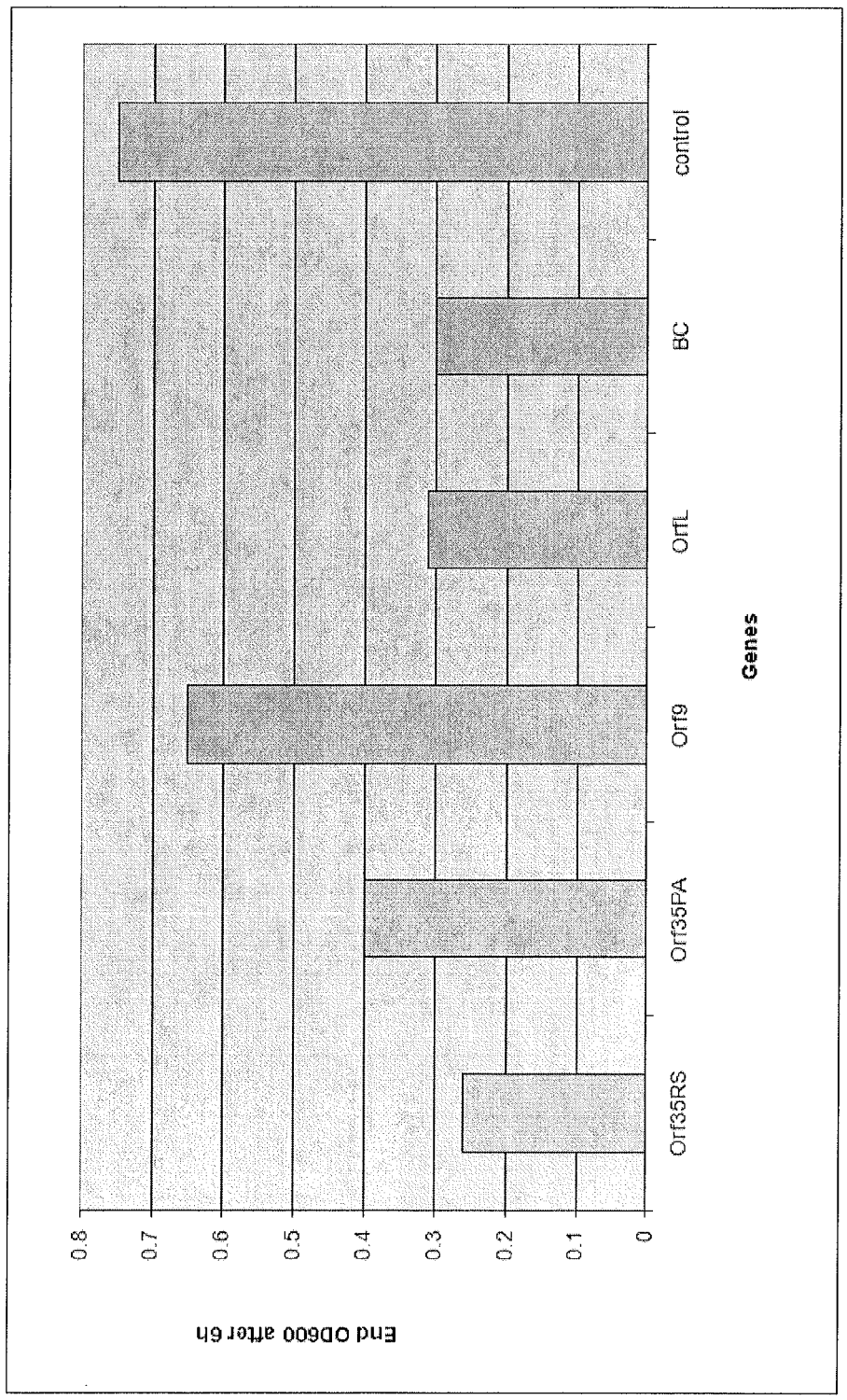
Figure 14:
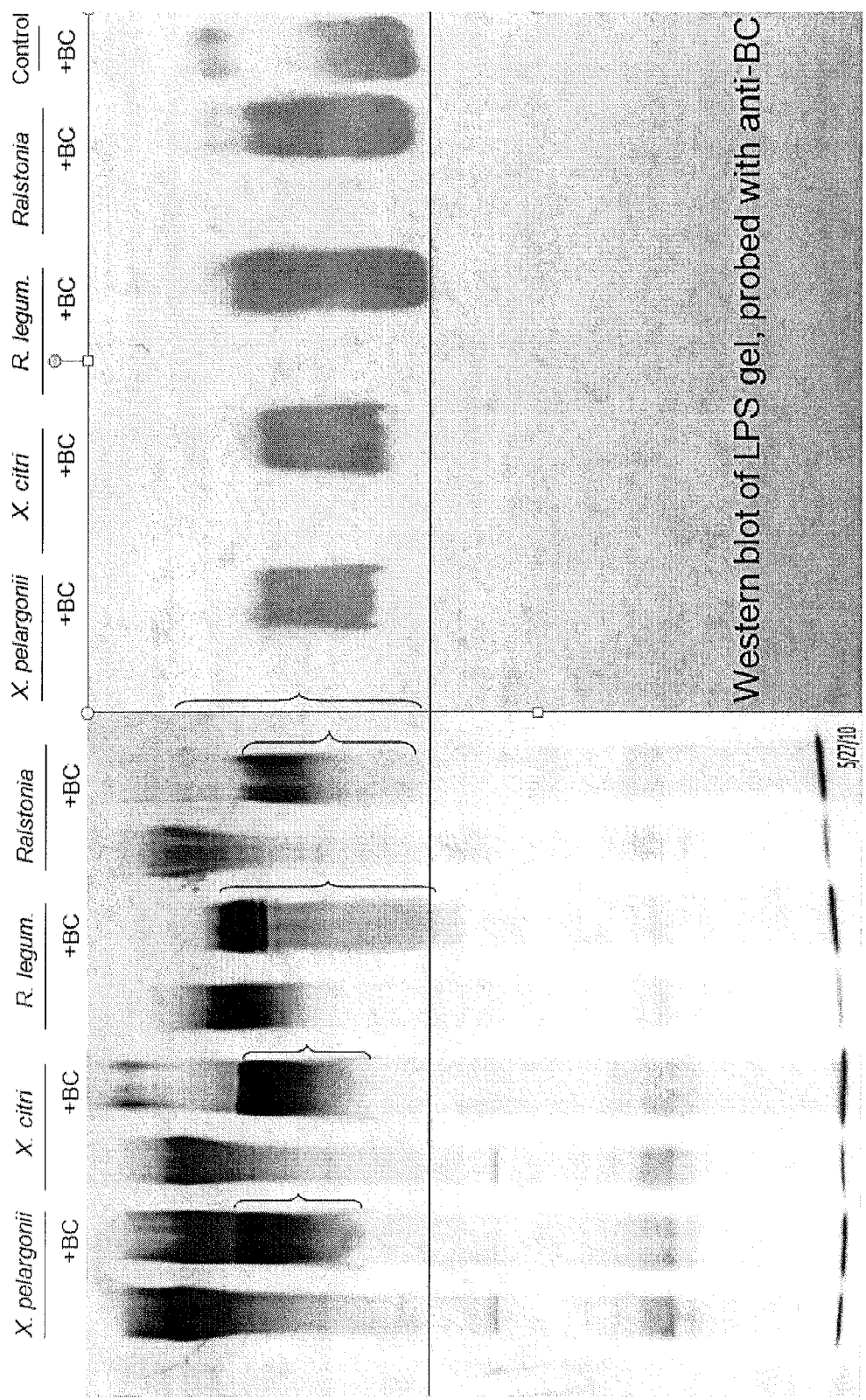

The codon optimized BC gene in pIPG973 is identical to that found in pIPG980, and both have 82% DNA sequence identity with the native, non-codon optimized BC gene (SEQ ID 1 of INTE_004_02US_SeqList_ST25.txt), not counting the intron. The BC protein predicted to be expressed from the codon optimized BC gene in pIPG973 and pIPG980 has 100% protein sequence identity with the predicted BC protein expressed from the native BC gene (refer FIG. 8). A non-codon optimized BC gene in pIPG786 has 99% DNA sequence identity with the native BC gene and encodes a predicted BC protein with a single amino acid substitution that has 99% protein sequence identity with the predicted BC protein expressed from the native BC gene (refer FIG. 8). pIPG786 is functional in various transgenic plants created to provide bacterial resistance (U.S. Ser. No. 12/176,874).

pIPG980 was transferred into *S. meliloti*/pTWBi3 by electroporation and confirmed by PCR analysis of miniprep DNA. pIPG973 was transferred into *A. tumefaciens* AGL1/pTiBo542 by electroporation and confirmed by similar PCR analysis.

Example 25

Comparative Efficacy of Bacterial Resistance Conferred by Codon-Optimized BC Vs. Non-Codon-Optimized BC in Transgenic Tobacco Both pIPG973 and pIPG980 were used to transform tobacco as described by Broothaerts et al. (2005). Selected plants exhibiting good BC protein expression by Western blots were sexually reproduced. Comparative pathogen challenge inoculations of transgenic tobacco (*Nicotiana tabaccum* cv. *Xanthi*) plants expressing BC were conducted using *Ralstonia solanacearum*. Sexually propagated (seeded, T1 generation) tobacco plants were inoculated and compared. *R. solanacearum* strain Rsp446, which is strongly pathogenic to tobacco, was inoculated by adding 5 ml of a liquid culture containing $5\times10^7$ to $2\times10^8$ colony forming units (cfu)/ml of Rsp446 cells directly to the soil of the potted tobacco plants. Following inoculation, plants were held at 32° C. to encourage pathogen growth and symptom development. Plants were examined daily and wilted plants exhibiting black vein symptoms were noted and discarded. The results, recorded as number of survivors/total tested after 60 days are shown in FIG. 9.

Three experiments each were performed using pIPG786, carrying the non-codon optimized BC gene (refer U.S. Pat. No. 8,212,110) encoding 786BC (refer FIG. 8) and three experiments each with pIPG973 (FIG. 7) encoding 973BC (SEQ ID 3; refer FIG. 8). These results are shown in FIG. 3. Survival of transgenic (dark bars) tobacco transformed with the indicated plasmids was much greater than survival of nontransgenic (light bars) tobacco in each experiment. A minimum of 40 plants were used in each experimental comparison; results were averaged and are presented as per cent survivors. Both pIPG786 and pIPG973 conferred strong resistance to transgenic tobacco expressing 786BC and 973BC, respectively. There were no significant differences detected in levels of expressed resistance. These results demonstrate that a BC gene with only 82% DNA identity (i.e., SEQ ID 3) to the native BC gene can function well to provide plant resistance, and that a predicted BC protein that is 99% identical to the predicted native BC protein can function well to provide plant resistance.

Example 26

Comparative Effects of Single Amino Acid Substitutions and Also Large Truncations of BC on BC Activity in *E. coli*

The full length, native bombBC gene was cloned into the pTXB expression vector (New England Biolabs, Ipswich, Mass.), resulting in pTXB-BC (the predicted protein sequence is presented as "native" in FIG. 8). pTXB-M3 and pTXB-M4 were created by site directed mutagenesis of pTXB-BC using a QuickChange II XL kit (Agilent Technologies, Santa Clara, Calif.), resulting in pTXB-M3 and pTXB-M4; the predicted protein sequences are presented as "M3" (SEQ ID 4) and "M4" (SEQ ID 5) in FIG. 8. bombBC with the point mutation found in pIPG786 was also recloned into pTXB, resulting in pTXB-BC* (the predicted protein sequence is presented as 786* in FIG. 8). Extensive deletions of bombBC were made by PCR amplification of pTXB-BC using primers to amplify the entire pTXB vector and the desired regions of bombBC. The resulting plasmids carried deletions in the bombBC gene and resulted in: pTXB-D1 (aa26-169 of BC), pTXB-D2 (aa 77-169 of BC) and pTXB-D5 (aa135-169 of BC); the predicted protein sequences of each of these is presented as "D1" (SEQ ID 6), "D2" (SEQ ID 7), "D3" and "D4", respectively, in FIG. 8. The resulting constructs were transformed into *E. coli* expression strain ER2566 (New England Biolabs, Ipswich, Mass.).

Growth of ER2566 carrying each construct was monitored according to the following protocol: a single colony of ER2566 carrying each construct was inoculated in 5 ml of liquid Luria Broth (LB) medium containing 50 ug/ml of ampicillin and grown overnight at 37 degrees on an orbital shaker at 250 rpm. One ml of this overnight culture was transferred to 40 ml of fresh liquid LB medium containing 50 ug/ml of ampicillin and allowed to grow until the optical density of the culture at 600 nm ($OD_{690}$) reached 0.2. Berberine chloride (Sigma-Aldrich, St. Louis, Mo.) and isopropyl β-D-1-thiogalactopyranoside (IPTG; Promega, Madison, Wis.) were both then added to final concentrations to 250 ug/ml and 0.25 mM, respectively. IPTG was added to induce strong expression of the BC gene or derivative gene. Berberine chloride was added to induce bacterial stasis in the presence of BC protein (which degrades the chemical barrier performance of the outer bacterial membrane). After addition of IPTG and berberine chloride, the cultures were allowed to continue to grow at 37 degrees on an orbital shaker at 250 rpm. The $OD_{600}$ of the culture was measured every hour after these additions for six hours (data not shown), and a final measurement made after 20 hrs. Each growth experiment on each strain was repeated at least three times, and the results after 20 hrs of induction were averaged and are shown in FIG. 10. Bacterial stasis was clearly induced in the presence of berberine chloride by expression of BombBC protein and mutants D1 (SEQ ID 6), D2 (SEQ ID 7), BC*, M3 (SEQ ID 4) and M4 (SEQ ID 5), which are 85%, 55%, 99%, 99% and 99% identical, respectively, to BC in amino acid composition (refer FIG. 8). In the absence of berberine chloride, no stasis was induced by expression of BC or any of these mutants (data not shown). These results demonstrate that full BombBC activity was observed in versions of BombBC truncated up to the point of 55% remaining identity.

Example 27

Confirmation of Full BC Activity in a Version of BC Truncated by 55% and Applied from Outside the Bacterium The results presented in Example X-3 demonstrated that a version of BC truncated by up to 55% retained full activity on bacterial outer membranes when the protein is made within the bacterial cell. In order to confirm that activity was preserved when a truncated version of BC or is presented externally to the bacterial cell (as would be the case in a transgenic plant expressing the BC gene or a truncated version of BC), an assay was used that specifically detects damage to the bacterial outer membrane. This is done using the P3rpoH::lacZ reporter system found in engineered into *E. coli* strain ADA410 as described by Bianchi and Baneyx, 1999. In this system, when the outer membrane is damaged, the P3 promoter of ADA410 is activated and drives expression of the lacZ gene. When lacZ is expressed, it creates an enzyme with beta-galactosidase activity, which is readily detected by conversion of a colorless substrate, such as X-gal (5-bromo-4-chloro-indolyl-β-D-galactopyranoside) into a dark blue color that can be quantified using a spectrophotometer.

In these experiments, purified BombBC, BC-D2 and 786* proteins were made using cultures of ER2566 carrying the expression vectors pTXB (empty vector), pTXB-BC, pTXB-BC* or pTXB-D2 (aa 77-169 of BC; SEQ ID 7). Cultures were grown and protein expression was induced as described in Example X-3, except that berberine chloride was omitted and cells were grown only 4 hours after induction. Protein was then purified from the induced cells using the IMPACT protein purification kit (New England Biolabs, Ipswich, Mass.), exactly as described by the manufacturer. Following protein extraction and quantification, protein was directly added to ADA410 bacterial cells. The ADA410 reporter cells were prepared from a single colony of ADA410, incubated in 5 ml of LB medium overnight at 25 degrees with orbital shaking at 250 rpm, collected by centrifugation at 6000 g for 5 min and resuspended in 100 ul of 50 mM monobasic potassium phosphate buffer (pH=6.5). 100 microliters of resuspended ADA410 culture was mixed with 10 micrograms of purified BC, BC-D2 or 786* protein (predicted sequences provided in FIG. 8) and kept at 25 degrees for 2 hours. Beta-galactosidase activity was measured using a beta-galactosidase assay kit (Agilent Technologies, Santa Clara, Calif.) and spectrophotometer set to read at 420 nm. Results shown in FIG. 11 are averages of 3 experiments. These results confirm and extend results presented in Example 3, and demonstrate that externally applied BC or a truncated version of BC with only 55% remaining identity were equally efficacious in damaging the bacterial outer membrane.

Example 28

Localization of Beta Strands Predicted to Form Beta Barrels in BombBC and Use in Identifying Candidate Proteins in Existing Phage Genomes with Function Similar to BombBC A useful web based program for the prediction of Beta barrel structures in proteins of known primary sequence is PRED-TMBB (Bagos, 2004). This program was used first to evaluate BombBC, which appeared to breach the bacterial outer membrane of *E. coli*, based upon the experimental evidence obtained in Examples 3 and 4. When run in PRED-TMBB, BombBC revealed two anti-parallel beta strands predicted to form a beta barrel and therefore be localized to the outer membrane of Gram-negative bacteria. The graphical output from PRED-TMBB is shown in FIG. 12. The antiparallel Beta strands that form the Beta barrel structure are shown embedded within the outer membrane and span from amino acids (aa) 28-IAVVALARF-36 and 68-AYVTADF-74. The N terminal region (aa 1-27), and the intervening loop region (37-GSQSTTTTKAAADALGTTVGKIDDIRKN-RNF-68) were shown to be dispensable for activity in BombBC mutant D2 (SEQ ID No. 7); refer FIG. 10 and Examples 3 and 4.

The PRED-TMBB program was then used to examine the predicted protein sequences of ORFs from a variety of different bacterial phage found in GenBank, including: 1) phage PhiKMV from *Pseudomonas aeruginosa*, encoding the BombORF35PA peptide in SEQ ID 9; 2) phage RSB1 from *Ralstonia solanacearum*, encoding the BombORF35RS peptide in SEQ ID 11; 3) phage Xp13 from *Xanthomonas campestris* pv. *pelargonii* encoding the BombOrf9 peptide in SEQ ID 13, and 4) phage Xp15 from *Xanthomonas campestris* pv. *pelargonii* (GenBank Accession AY986977.1) encoding the BombOrfL peptide in SEQ ID 15. In each of these 4 phage, putative Bomb proteins were discovered based upon the PRED-TMBB prediction of the presence of beta strands likely to form a outer membrane beta barrel structure.

Genes encoding the four putative Bomb proteins were either commercially synthesized (in the cases of SEQ ID 8 and 10) or PCR amplified (in the cases of SEQ ID 12 and 14), and cloned into the pTXB vector between the NdeI and SpaI sites. The clones were confirmed by sequecing and re-transformed into ER2566 cells (NEB). A single colony of each strain was incubated in LB medium (Amp 50) overnight with shaking at 250 rpm. One ml of the overnight culture was transerred into 20 ml of LB medium (Amp 50) and continued to shake at 250 rpm. Once the $OD_{600}$ of the culture reached 0.2, 20 ml of LB medium containing 500 mg/ml berberine chloride (freshly prepared) and 0.25 mM IPTG was added to the culture. The bacteria growth was monitored for $OD_{600}$ every hour. The results are shown in FIG. 13.

Clearly, the new phage gene with the strongest activity in *E. coli* was BombORF35RS from phage RSB1 from *Ralstonia solanacearum*, followed by BombBC and BombOrfL, both from phage Xp15 from *X. campestris* pv. *pelargonii*, followed by Bomb ORF35PA from phage PhiKMV from *Pseudomo-*

*nas aeruginosa*. Weak activity was observed with BombOrf9 from phage Xp13 from *Xanthomonas campestris* pv. *pelargonii*.

BombORF35PA, BombORF35RS and BombOrfL have no significant amino acid identities to BombBC using pairwise BLAST and standard settings (low complexity filter off and Word size=3), while BombOrf9 has 50% identity over a very short stretch of 14 amino acids to BombBC. Taken together, these four genes provide examples that the methodology of first screening a sequenced phage genome for genes predicted to form beta barrels and second expressing these genes in a *E. coli* in the presence of a phytoalexin provides a practical method of discovering one or two gene candidates likely to have Bomb activity.

Based on TMBBPred, exactly two anti-parallel beta strands were found in all of these phage genes that were predicted to form beta barrels and therefore be localized in Gram-negative bacterial outer membrane. This beta strand domain and linker region, which was found to be similar in appearance to that illustrated in FIG. 12 in all of these phage genes, and which was also found in a similar N-terminal location in all of these phage genes, corresponds to amino acids 1-39 of ORF35 PA, amino acids 1-32 of ORF35 RS, amino acids 1-45 of Orf9, and amino acids 1-54 of ORFL. Based on deletion analyses of BombBC, these amino acids, if deleted, would still allow the remaining protein domain to retain outer membrane breaching properties, since these Beta strands are structural elements involved in outer membrane insertion.

Example 29

Biochemical Function of BombBC

In order to attempt to determine the exact mechanism by which BombBC was able to breach the bacterial outer membrane, the lipopolysaccharide (LPS), which forms the unique outer leaflet of the Gram-negative bacterial outer membrane, was extracted from a variety of plant pathogenic or symbiotic bacteria, including *X. campestris* pv. *pelargonii* (causes geranium blight, a representative Gammaproteobacteria), *X. citri* (causes citrus canker, also a Gammaproteobacteria), *Rhizobium leguminosarum* (nodulates beans, a representative Alphaproteobacterium), and *Ralstonia solanacearum* (causes brown rot and wilt, a representative Beta proteobacteria. The LPS of each species, particularly those from different classes, are quite different in composition.

For LPS extractions, bacteria were inoculated in 50 ml of appropriate growth medium with shaken at 200 rpm at 28° C. overnight. The cells were collected by centrifugation at 6000 g for 10 min. The pellet was washed with 0.7% NaCl twice. The cell pellet was suspended in 1 ml of 45% aqueous phenol (pH=6.8) solution. The suspension was incubated at 65° C. for 1 h with vortexing every 30 min. The water and phenol layers were separated by centrifugation at 10,000×g for 30 min. The water layer was collected and digested by ribonuclease (100 Kunitz units) for 2 hr. Following the digestion, the water layer was dialyzed against deionized water for 2 days.

In order to determine if BombBC enzymatically degraded the LPS of any or all of these bacteria, the following assay was performed. A single colony of *E. coli* ER2566 carrying expression clone pTXB-BombBC was inoculated in 5 ml of Luria Broth medium (containing the antibiotic ampicillin) with shaking at 200 rpm at 37° C. overnight. 1 ml of this overnight culture was transferred to 50 ml of fresh LB medium and incubated until the $OD_{600}$ reached 0.4. 12.5 microliters of 1M IPTG was added to the medium to make the final concentration 0.25 mM. The culture was incubated at 37° C. for another 2 hours with shaking. The cells were collected by centrifugation at 6000×g for 10 min. Total protein was extracted using Bugbuster master mix (EMD Biosciences, San Diego). The recombinant BombBC protein was purified using the IMPACT protein purification kit (NEB, Ipswich, Mass.).

The enzymatic assay was carried in a 20 ul volume with a mixture containing 5 ug of purified BC protein, 2 ul of 10×Tris buffer (0.5 M, pH7.6), 1 mM of $MgCl_2$ and 5 ul of extracted LPS. The mixture was incubated at room temperature for 2 hours. The reaction was terminated by adding 20 ul of 2×LPS sample buffer (175 mM Tris, pH 6.8, 10% glycerol, and 1% bromophenol blue) and boiled at 65° C. for 20 min. The samples were subjected to SDS-PAGE (sodium dodecyl sulfate-polyacrylamide gel electrophoresis).

To perform the electrophoresis, 20 ul of each protein sample was loaded onto a 15% SDS-PAGE gel in different lanes and the proteins were separated by running at 120 V for 120 min using standard Tris-borate EDTA (TBE) buffer. The gel was subjected to either silver staining or western blot assay, as indicated. The silver staining was performed using a silver staining kit (Bio-Rad, Hercules, Calif.).

For Western blots, the proteins in the SDS-PAGE gel were transferred onto a PVDF membrane using either a semi-dry or tank transfer method. The membrane was blocked in 15 ml of blocking buffer (3% BSA in TBST buffer) for 1 hr and incubated in 15 ml of 3% BSA containing 3 ul of anti-BC antiserum overnight. The blot was washed 6 times (5 min each) in 10 ml of TBST buffer followed by incubation at 3% BSA solution containing 1 ul of anti-rabbit secondary antibodies (Santa Cruz Biotechnology, Santa Cruz, Calif.) for 1 hr. After incubation, the blot was washed 6 times (5 min each) in 10 ml of TBST buffer and the signal was detected using Western lightning-ECL kit (PerkinElmer, Waltham, Mass.).

Results are shown in FIG. 14. A silver stained, SDS-PAGE gel, loaded with purified LPS extracted from *X. campestris* pv. *pelargonii, X. citri, Rhizobium leguminosarum* and *Ralstonia solanacearum* is shown on the left half of FIG. 14. Two lanes are shown for each bacterium, run side by side. The left lane under each indicated bacterium is untreated LPS from the indicated bacterium. The right lane under each indicated bacterium is the same LPS, but treated with purified BombBC protein for 2 hours (treated lanes labeled "BC"). Brackets are added to the figure to indicate degraded LPS products that do not appear in the untreated lanes. These results were repeated several times (not shown), with similar results. These results demonstrate that BombBC enzymatically degrades LPS.

On the right half of FIG. 14 is shown a Western blot of the same gel shown on the left, probed with polyclonal antisera raised against BombBC. As expected, untreated LPS lanes have no BombBC detected; only treated lanes reveal BombBC present. An additional control of purified BC protein was run on the gel (not shown in the left photo) and appears on the Western blot. Note that BombBC appears attached to the degraded LPS of all species tested, since it is found in an identical pattern of distribution observed by the LPS that it is degrading. These results demonstrate that BombBC attaches to the LPS that it is engaged in degrading.

It must be noted that as used in this specification and the appended claims, the singular forms "a," "and," and "the" include plural referents unless the contexts clearly dictates otherwise. Thus, for example, reference to "Bomb proteins" includes any one, two, or more of the Bomb proteins or fragments thereof, regardless of source; reference to "a transgenic plant" includes large numbers of transgenic plants and mixtures thereof, and reference to “the method” includes one or more methods or steps of the type described herein.

Example 30

Additional Truncated Bomb Polypeptides

Bomb proteins derived from other phages, such as BombORF35PA (SEQ ID NO. 9), BombORF35RS (SEQ ID NO. 11); BombOrf9 (SEQ ID NO. 13); and BombOrfL (SEQ ID NO. 15) were subjected to the PRED-TMBB program analysis, and it was determined that the following beta strand-linker-beta strand regions are dispensable and/or interchangeable: (1) aa 1-39 of the BombORF35PA peptide (SEQ ID NO. 9); (2) aa 1-32 of the BombORF35RS peptide (SEQ ID NO. 11); (3) aa 1-45 of the BombOrf9 peptide (SEQ ID NO. 13); and (4) aa 1-54 of the BombOrfL peptide (SEQ ID NO. 15). That is, a truncated Bomb protein derived from these Bomb proteins without such dispensable regions are still functional in causing quasilysis in Gram-negative bacteria, such as *E. coli*.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the exemplary methods and materials are described herein. All publications cited herein are incorporated herein by reference for the purpose of disclosing and describing specific aspects of the invention for which the publication is cited.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

LITERATURE CITED

Arce P et al. 1999. Enhanced resistance to bacterial infection by *Erwinia carotovora* subsp. Atroseptica in transgenic potato plants by expressing the attacin or the cecropin SB-37 genes. American Journal of Potato Research 76:169-177.

Bagos P G, Liakopoulos T D, Spyropoulos I C and Hamodrakas S J. 2004. A Hidden Markov Model method, capable of predicting and discriminating beta-barrel outer membrane proteins. BMC Bioinformatics 5:29.

Balsanelli, E., Serrato, R. V., de Baura, V. A., Sassaki, G., Yates, M. G., Rigo, L. U., Pedrosa, F. O., de Souza, E. M., and Monteiro, R. 2010. *Herbaspirillum seropedicae* rfbB and rfbC genes are required for maize colonization. Env. Microbiol. 12(8):2233-2244.

Bianchi, A. A. and Baneyx, F. 1999. Stress Responses as a Tool To Detect and Characterize the Mode of Action of Antibacterial Agents. Applied and Enviromental Microbiology. 65: 5023-5027.

Bolton, E. T. and McCarthy, B. J. 1962. A general method for the isolation of RNA complementary to DNA. Proc. Natl. Acad. Sci. USA 48:1390.

Broekaert, W. F. et al. 1997. Antimicrobial peptides from plants. Critical Reviews in Plant Sciences 16:297-323.

Broothaerts, W. et al., 2005. Gene transfer to plants by diverse species of bacteria. Nature 433:629-633.

Callis, J., M. Fromm, and V. Walbot. 1987. Introns increase gene-expression in cultured maize cells. Genes & Development 1:1183-1200.

Calvo, M. V. and Fontecha, J. 2004. Purification and characterization of a pregastric esterase from a hygienized kid rennet paste. J. Dairy Sci. 87:1132-1142.

Ceccardi, T. L., G. A. Barthe, and K. S. Derrick. 1998. A novel protein associated with citrus blight has sequence similarities to expansin. Plant Molecular Biology 38:775-783.

Desnuelle, P. and Savary, P. 1963. Specificity of lipases. J. Lipid Research 4:309-384.

Donlan R M (2009) Preventing biofilms of clinically relevant organisms using bacteriophage. Trends Microbiol 17:66-72.

Doyle, M. P. 2000. Reducing foodborne disease: What are the priorities? Nutrition 16:647-649.

Duan Y P et al. 1999. Expression of a single, host-specific gene in citrus cells elicits division, enlargement and cell death. Molecular Plant-Microbe Interactions 12:556-560

During K et al. 1993. Transgenic potato plants resistant to the phytopathogenic bacterium *Erwinia carotovora*. Plant J 3:587-598

During, K., P. Porsch, A. Mahn, O. Brinkmann, and W. Gieffers. 1999. The non-enzymatic microbicidal activity of lysozymes. FEBS Letters 449:93-100.

Flachowsky, H.; Richter, K.; Kim, W.-S.; et al. 2008. Transgenic expression of a viral EPS-depolymerase is potentially useful to induce fire blight resistance in apple. Ann. Appl. Biol. 153: 345-355.

Francischini et al., 2007. First Report on the Transmission of Candidatus Liberibacter *americanus*' from Citrus to *Nicotiana tabacum* cv. *Xanthi*. Plant Disease 91:631.

Gabriel, D. W., Allen, C., Schell, M., Denny, T. P., Greenberg, J. T., Duan, Y. P., Flores-Cruz, Z., Huang, Q., Clifford, J. M., Presting, G., Gonzalez, E. T., Reddy, J. D., Elphinstone, J., Swanson, J., Yao, J., Mulholland, V., Liu, L., Farmerie, W., Patnaikuni, M., Balogh, B., Norman, D., Alvarez, A., Castillo, J. A., Jones, J., Saddler, G., Walunas, T., Zhukov, A., Mikhailova, N. 2006. Identification of open reading frames unique to a Select Agent: *Ralstonia solanacearum* race 3 biovar 2. Molec. Plant-Microbe Interact. 19:69-79.

Grimmecke, H., Knirel, Y., Shashkov, A., Kiesel, B., Lauk, W., Voges, M. 1994. Structure of the capsular polysaccharide and the O-side-chain of the lipopolysaccharide from *Acetobacter-methanolicus* Mb-70, and of oligosaccharides resulting from their degradation by the bacteriophage-Acm6. Carb. Res. 253: 277-282.

Gruber, V., Berna, B. P., Arnaud, T., et al. 2001. Large-scale production of a therapeutic protein in transgenic tobacco plants: effect of subcellular targeting on quality of a recombinant dog gastric lipase. Molec. Breeding 7:329-340.

Grundling, A., Manson, M. D., Young, R. 2001. Holins kill without warning. Proc. Natl. Acad. Sci. USA 98: 9348-9352

Gupta, R., Rathi, P., Gupta, N., Bradoo, S. 2003. Lipase assays for conventional and molecular screening: an overview. Biotechnol. Appl. Biochem. 37:63-71.

Hiei Y, Komari T, Kubo T., 1997. Transformation of rice mediated by *Agrobacterium tumefaciens*. Plant Mol Biol. 35:205-18.

Horsch, R. B., Fry, J. E., Hoffmann, N. L., Eichholtz, D., Rogers, S. G. and Fraley, R. T. 1985. A simple and general method for transferring genes into plants. Science 227: 1229-1231.

Ibrahim, H. R., Thomas, U., and Pellegrini, A. 2001. A helix-loop-helix peptide at the upper lip of the active site cleft of lysozyme confers potent antimicrobial activity with membrane permeabilization action. J. Biol. Chem. 276:43767-43774.

Jaynes J M et al. 1987. Increasing bacterial disease resistance in plants utilizing antibacterial genes from insects. Bioassays 6:263-270

Jaeger, K. E. and Reetz, M. T. 1998. Microbial lipases form versatile tools for biotechnology. Trends Biotechnol. 16:396-403.

Janin, J. and Wodak, S. J (1983). "Structural domains in proteins and their role in the dynamics of protein function". Prog Biophys Mol Biol 42 (1): 21-78.

Jette, J. F. and Ziomek, E. 1994. Determination of lipase activity by a Rhodamine-Triglyceride-Agarose assay. Analytical Biochemistry 219:256-260.

Kapila, J., R. De Rycke, M. Van Montagu, and G. Angenon. 1997. An *Agrobacterium*-mediated transient gene expression system for intact leaves. Plant Science 122:101-108.

Kato, A., S. Nakamura, H. Ibrahim, T. Matsumi, C. Tsumiyama, and M. Kato. 1998. Production of genetically modified lysozymes having extreme heat stability and antimicrobial activity against Gram-negative bacteria in yeast and in plant. Nahrung-Food 42:128-130.

Kawasaki, T., Shimizu, M., Satsuma, H., et al. 2009. Genomic Characterization of *Ralstonia solanacearum* Phage phi RSB1, a T7-Like Wide-Host-Range Phage. J. Bact. 191: 422-427.

Kim, I. G., Lee, M. S., Jin, T. E., Hwang, B. K., Lee, J. H., Suh, S. C., and Rhim, S. L. 2004. Inhibitory effect of bacteriophage EPS-depolymerase on growth of Asian pear blight pathogen *Erwinia pyritbliae*. J. Microbiol. Biotech. 14: 872-876

Kingsley, M. T., D. W. Gabriel, G. C. Marlow, and P. D. Roberts. 1993. The opsX locus of *Xanthomonas campestris* affects host range and biosynthesis of lipopolysaccharide and extracellular polysaccharide. J. Bacteriol. 175: 5839-5850.

Koebnik, R., Locher, K. P. and P. Van Gelder. 2000. Structure and function of bacterial outer membrane proteins: barrels in a nutshell. Molec. Microbiol. 37:239-253, Ko K. 1999. Attacin and T4 lysozyme transgenic in Galaxy apple: Regulation of transgene expression and plant resistance to fire blight (*Erwinia amylovora*). PhD dissertation, Cornell University, Ithaca N.Y. 194 pp.

Ko K et al. 2000. Effect of untranslated leader sequence of AMV RNA 4 and signal peptide of pathogenesis-related protein 1b on attacin gene expression, and resistance to fire blight in transgenic apple. Biotechnology Letters 22:373-381Li Q et al. 2001. Enhanced disease resistance conferred by expression of an antimicrobial magainin analog in transgenic tobacco. Planta 212:635-639.

Lavigne, R., Burkal'tseva, M. V., Robben, J., et. Al., 2003. The genome of bacteriophage phiKMV, a T7-like virus infecting *Pseudomonas aeruginosa*. Virology 312: 49-59.

Lifson S. and Sander C., 1979. Antiparallel and parallel beta-strands differ in amino-acid residue preferences. Nature 282:109-111.

Malnoy, M., Faize, M., Venisse, J. S, Geider, K., Chevreau, E., 2005. Expression of viral EPS-depolymerase reduces fire blight susceptibility in transgenic pear. Plant Cell Rep 23:632-638.

Mitra A and Zhang Z. 1994. Expression of a human lactoferrin cDNA in tobacco cells produces antibacterial protein(s). Plant Physiol 106:977-981.

Moore G. A., Jacono, C. C., Neidigh J. L., Lawrence S. D. and Cline K., 1992. *Agrobacterium*-mediated transformation of citrus stem segments and regeneration of transgenic plants. Plant Cell Rep 11:238-242.

Moore, I., et al. 1998. A transcription activation system for regulated gene expression in transgenic plants. Proc. Natl. Acad. Sci. USA 95:376-381.

Mun, J. H., Lee, S. Y., Yu, H. J., Jeong, Y. M., Shin, M. Y., Kim, H., Lee, I., and Kim, S. G. *Petunia* actin-depolymerizing factor is mainly accumulated in vascular tissue and its expression is enhanced by the first intron. Gene 292, 233-243. 2004.

Murashige, T. and Skoog, F. 1962. A revised medium for rapid growth and bioassays with tobacco tissue cultures. Physiol. Plant 15: 473-497.

Nakajima H et al. 1997. Fungal and bacterial disease resistance in transgenic plants expressing human lysozyme. Plant Cell Rep 16:674-679.

Norelli J L et al 1994. Transgenic Mailing 26 apple expressing the attacin E gene has increased resistance to *Erwinia amylovora*. Euphytica 77:123-128.

Norelli J L et al. 1998. Effect of cercropin-type transgenes on fire blight resistance of apple. Acta Hort 489:273-278.

Norelli J L et al. 1999. Genetic transformation for fire blight resistance in apple. Acta Hort 489:295-296.

Owens, L. D. and Heutte, T. M. (1997) A single amino acid substitution in the antimicrobial defense protein cecropin B is associated with diminished degradation by leaf intercellular fluid. Molecular Plant-Microbe Interactions. 10, 525-528.

Pace, C N and Scholtz J M 1998. Biophysical Journal 75: 422-427.

Reddy, JD, Reddy, SL, Hopkins, DL, and Gabriel, D W. 2007. TolC is required for pathogenicity of *Xylella fastidiosa* in grape plants. Molec. Plant-Microbe Interact. 20:403-410.

Rendueles, O., and J. M. Ghigo. 2012. Multi-species biofilms: how to avoid unfriendly neighbors. FEMS Micro. Rev. 36:972-989.

Reynoird J P et al. 1999. First evidence for differences in fire blight resistance among transgenic pear clones expressing attacin gene. Plant Science 149:23-31.

Riggs, C. D., K. Zeman, R. DeGuzman, A. Rzepczyk and A. A. Taylor. 2001. Antisense inhibition of a tomato meiotic proteinase suggests functional redundancy of proteinases during microsporogenesis Genome 44: 644-650.

Robichon, M. P., J. P. Renou and R. Jalouzot, 1995. Genetic transformation of *Pelargonium* X *hortorum*. Plant Cell Reports 15:63-67.

Rose, A. B. and Beliakoff, J. A. Intron-mediated enhancement of gene expression independent of unique intron sequences and splicing. Plant Physiol. 122, 535-542. 2004.

Rose, A. B. 2002. Requirements for intron-mediated enhancement of gene expression in *Arabidopsis*. Rna-A Publication of the Rna Society 8:1444-1453.

Rost, B. and J. Liu 2003. The PredictProtein server. Nucl Acids Res 31: 3300-3304

Sambrook, J., Fritsch, E. F. and Maniatis, T., 1989. Molecular Cloning: A Laboratory Manual, Cold Spring Harbor Laboratory Press, NY Schmeller, T., Latz-Bruning, B., and Wink, M. 1997. Biochemical activities of berberine, palmatine and sanguinarine mediating chemical defence against microorganisms and herbivores. Phytochemistry 44:257-266

Schultz, G. E., 2002. The structure of bacterial outer membrane proteins. Biochim. Biophys Acta 1565:308-317).

Schulz, G. E. 2000. Beta-barrel membrane proteins. Curr. Opin. Struct. Biol., 10, 443-447).

Segura, A., Moreno, M., Molina, A., Garcia-Olmedo, F., 1998. Novel defensin subfamily from spinach (*Spinacia oleracea*). FEBS Letters 435:159-162.

Shapiro, E., and Baneyx, F. 2002. Stress-based identification and classification of antibacterial agents: second generation *Escherichia coli* reporter strains and optimization of detection. Antimicrobial Agents Chemotherapy 46: 2490-2497.

Simpson, G. G. and Filipowicz, W. Splicing of precursors to mRNA in higher plants: mechanism, regulation an subnuclear organization of the spliceosomal machinery. Plant Mol. Biol. 32, 1-41. 1996.

Singh, R., Gupta, N., Goswami, V. K. and R. Gupta. 2006. A simple activity staining protocol for lipases and esterases. Appl. Microbiol. Biotechnol. 70:679-682.

Taguchi S et al. 2000. Functional mapping against *Escherichia coli* for the broad-spectrum antimicrobial peptide, thanatin, based on an in vivo monitoring assay system. J Biochem 128:745-754.

Taylor W R. (1999). "Protein structural domain identification". *Protein Eng* 12 (3): 203-16

Timmermans, M. Y. J., Teuchy, H., and Kupers, L P M. 1998. The cDNA sequence encoding boving pregastric esterase. Gene 147: 259-262.

Trudel J et al. 1995. Secreted hen lysozyme in transgenic tobacco: Recovery of bound enzyme and in vitro growth inhibition of plant pathogens. Plant Science 106:55-62.

Vunnam S et al. 1997. Synthesis and antibacterial action of cecropin and proline-arginine-rich peptides from pig intestine. J Peptide Res 49:59-66.

Wang Y et al. 1999. Porcine pulmonary surfactant preparations contain the antibacterial peptide prophenin and a C-terminal 18-residue fragment thereof. FEBS Lett 460: 257-262.

Wroblewski, T., Tomczak, A. and Michelmore, R. 2005. Optimization of *Agrobacterium* mediated transient assays of gene expression in lettuce, tomato and *Arabidopsis*. Plant Biotechnology J. 3:259-273.

Zhou, L. J., Gabriel, D. W., Duan, Y. P, Halbert, S., and Dixon, W. 2007. First Report of Dodder Transmission of Huanglongbing from Naturally Infected *Murraya paniculata* to Citrus. Plant Disease 91:227.

The invention claimed is:

1. A transgenic plant, plant part, plant cell, or plant tissue culture comprising a DNA molecule, wherein the DNA molecule encodes a Bacterial Outer Membrane Breaching (BOMB) polypeptide sharing at least 90% amino acid identity with a BOMB polypeptide selected from the group consisting of SEQ ID NO:9, SEQ ID NO:11, SEQ ID NO:13, SEQ ID NO:15, and SEQ ID NO:17.

2. The transgenic plant, plant part, plant cell, or plant tissue culture of claim 1, wherein the DNA molecule encodes a BOMB polypeptide sharing at least 95% amino acid identity with a BOMB polypeptide selected from the group consisting of SEQ ID NO:9, SEQ ID NO:11, SEQ ID NO:13, SEQ ID NO:15, and SEQ ID NO:17.

3. The transgenic plant, plant part, plant cell, or plant tissue culture of claim 1, wherein the DNA encoding the BOMB polypeptide is any codon-optimized version of said DNA.

4. A method for enhancing resistance of a plant to infection or infestation by Gram-negative bacteria, said method comprising introducing into the genome of the plant an expression cassette comprising:
  1) a plant promoter;
  2) a gene comprising a nucleic acid sequence selected from the group consisting of
     (a) a nucleic acid sequence encoding a BOMB polypeptide sharing at least 90% amino acid identity with a BOMB polypeptide selected from the group consisting of SEQ ID NO:9, SEQ ID NO:11, SEQ ID NO:13, SEQ ID NO:15, and SEQ ID NO:17; and
     (b) any codon optimized version of a nucleic acid of a sequence of (a), wherein the nucleic acid sequence is operably fused to said promoter; and
  3) a plant terminator.

5. The method of claim 4, wherein the Gram-negative bacteria are pathogenic.

6. The method of claim 4, wherein the expression cassette further comprises a nucleic acid sequence encoding a secretion signal and/or an intron.

7. The method of claim 4 wherein the expression cassette further comprises an endoplasmic reticulum (ER) retention signal.

8. The method of claim 4, wherein said BOMB polypeptide is used in combination with, whether separately cloned and transformed or not, whether operably fused with or not, an additional protein, polypeptide, or peptide fragment selected from the group consisting of:
  (1) a nonenzymatic lytic peptide or peptide fragment,
  (2) an enzymatic lytic peptide or peptide fragment or protein, and
  (3) an enzymatic peptidoglycan degrading peptide or peptide fragment.

9. The method of claim 8, wherein the additional protein, polypeptide, or peptide fragment is selected from the group consisting of lysozymes, endolysins, proteases, chitinases, mureinolytic enzymes, enzymes with transglycosylase activity, lipases and esterases, and functional fragments thereof.

10. The plant, plant part, plant cell, or plant tissue culture of claim 3, wherein the plant is a dicot plant or a monocot plant.

11. The plant, plant part, plant cell, or plant tissue culture of claim 3, wherein the plant is selected from the group consisting of geranium plants, citrus plants, tobacco plants, and rice plants.

12. Progeny of the plant of claim 3, wherein the progeny comprises the DNA molecule encoding the BOMB polypeptide.

13. The transgenic plant, plant part, plant cell, or plant tissue culture of claim 1, wherein the DNA molecule encoding the BOMB polypeptide comprises a plant intron.

14. The transgenic plant, plant part, plant cell, or plant tissue culture of claim 1, wherein the BOMB polypeptide originates from a bacteriophage.

15. The transgenic plant, plant part, plant cell, or plant tissue culture of claim 1, wherein the BOMB polypeptide has the following properties:
   (a) originating from a bacteriophage;
   (b) lacking a bacterial secretion signal sequence;
   (c) lacking a functional alphahelical transmembrane domain;
   (d) contains a beta strand-linker-beta strand domain, wherein the domain is predicted to localize in an outer membrane of a bacterium when contacted with the bacterium; and
   (e) contains a globular domain.

16. The method of claim 4, wherein the BOMB polypeptide shares at least 90% or at least 95% amino acid identity with a BOMB polypeptide selected from the group consisting of SEQ ID NO:9, SEQ ID NO:11, SEQ ID NO:13, SEQ ID NO:15, and SEQ ID NO:17.

* * * * *

SEQUENCE LISTING

```
<160> NUMBER OF SEQ ID NOS: 18

<210> SEQ ID NO 1
<211> LENGTH: 9561
<212> TYPE: DNA
<213> ORGANISM: Artificial Sequence
<220> FEATURE:
<223> OTHER INFORMATION: Plasmid pIPG973

<400> SEQUENCE: 1
gttaacgcta gccaccacca ccaccaccac gtgtgaatta caggtgacca gctcgaattt      60
ccccgatcgt tcaaacattt ggcaataaag tttcttaaga ttgaatcctg ttgccggtct     120
tgcgatgatt atcatataat ttctgttgaa ttacgttaag catgtaataa ttaacatgta     180
atgcatgacg ttatttatga gatgggtttt tatgattaga gtcccgcaat tatacattta     240
atacgcgata gaaaacaaaa tatagcgcgc aaactaggat aaattatcgc gcgcggtgtc     300
atctatgtta ctagatcggg aattaaacta tcagtgtttg acaggatata ttggcgggta     360
aacctaagag aaaagagcgt ttattagaat aacggatatt taaaagggcg tgaaaaggtt     420
tatccgttcg tccatttgta tgtgcatgcc aaccacaggg ttccctcgg gatcaaagta      480 ctttgatcca accctccgc tgctatagtg cagtcggctt ctgacgttca gtgcagccgt     540
cttctgaaaa cgacatgtcg cacaagtcct aagttacgcg acaggctgcc gccctgccct     600
tttcctggcg ttttcttgtc gcgtgtttta gtcgcataaa gtagaatact tgcgactaga     660
accggagaca ttacgccatg aacaagagcg ccgccgctgg cctgctgggc tatgcccgcg     720
tcagcaccga cgaccaggac ttgaccaacc aacgggccga actgcacgcg gccggctgca     780
ccaagctgtt ttccgagaag atcaccggca ccaggcgcga ccgcccggag ctggccagga     840
tgcttgacca cctacgccct ggcgacgttg tgacagtgac caggctagac cgcctggccc     900
gcagcacccg cgacctactg gacattgccg agcgcatcca ggaggccggc gcgggcctgc     960
gtagcctggc agagccgtgg gccgacacca ccacgccggc cggccgcatg gtgttgaccg    1020
```

```
tgttcgccgg cattgccgag ttcgagcgtt ccctaatcat cgaccgcacc cggagcgggc    1080
gcgaggccgc caaggcccga ggcgtgaagt ttggccccg ccctaccctc accccggcac     1140
agatcgcgca cgcccgcgag ctgatcgacc aggaaggccg caccgtgaaa gaggcggctg    1200
cactgcttgg cgtgcatcgc tcgaccctgt accgcgcact tgagcgcagc gaggaagtga    1260
cgcccaccga ggccaggcgg cgcggtgcct tccgtgagga cgcattgacc gaggccgacg    1320
ccctggcggc cgccgagaat gaacgccaag aggaacaagc atgaaaccgc accaggacgg    1380
ccaggacgaa ccgttttca ttaccgaaga gatcgaggcg gagatgatcg cggccgggta    1440
cgtgttcgag ccgcccgcgc acgtctcaac cgtgcggctg catgaaatcc tggccggttt    1500
gtctgatgcc aagctggcgg cctggccggc cagcttggcc gctgaagaaa ccgagcgccg    1560
ccgtctaaaa aggtgatgtg tatttgagta aaacagcttg cgtcatgcgg tcgctgcgta    1620
tatgatgcga tgagtaaata acaaatacg caaggggaac gcatgaaggt tatcgctgta     1680
cttaaccaga aaggcgggtc aggcaagacg accatcgcaa cccatctagc ccgcgccctg    1740
caactcgccg ggccgatgt tctgttagtc gattccgatc cccagggcag tgcccgcgat     1800
tgggcggccg tgcgggaaga tcaaccgcta accgttgtcg gcatcgaccg cccgacgatt    1860
gaccgcgacg tgaaggccat cggccggcgc gacttcgtag tgatcgacgg agcgccccag    1920
gcggcggact ggctgtgtc cgcgatcaag gcagccgact tcgtgctgat tccggtgcag     1980
ccaagccctt acgacatatg gccaccgcc gacctggtgg agctggttaa gcagcgcatt     2040
gaggtcacgg atggaaggct acaagcggcc tttgtcgtgt cgcgggcgat caaaggcacg    2100
cgcatcggcg gtgaggttgc cgaggcgctg gccgggtacg agctgcccat tcttgagtcc    2160
cgtatcacgc agcgcgtgag ctacccaggc actgccgccg ccggcacaac cgttcttgaa    2220
tcagaacccg agggcgacgc tgcccgcgag gtccaggcgc tggccgctga aattaaatca    2280
aaactcattt gagttaatga ggtaaagaga aatgagcaa agcacaaac acgctaagtg      2340 ccggccgtcc gagcgcacgc agcagcaagg ctgcaacgtt ggccagcctg cagacacgc     2400 cagccatgaa gcgggtcaac tttcagttgc cggcggagga tcacaccaag ctgaagatgt    2460
acgcggtacg ccaaggcaag accattaccg agctgctatc tgaatacatc gcgcagctac    2520
cagagtaaat gagcaaatga ataaatgagt agatgaattt tagcggctaa aggaggcggc    2580
atggaaaatc aagaacaacc aggcaccgac gccgtggaat gccccatgtg tggaggaacg    2640
ggcggttggc caggcgtaag cggctgggtt gtctgccggc cctgcaatgg cactggaacc    2700
cccaagcccg aggaatcggc gtgacggtcg caaaccatcc ggcccggtac aaatcggcgc    2760
ggcgctgggt gatgacctgg tggagaagtt gaaggccgcg caggccgccc agcggcaacg    2820
catcgaggca gaagcacgcc ccggtgaatc gtggcaagcg gccgctgatc gaatccgcaa    2880
agaatcccgg caaccgccgg cagccggtgc gccgtcgatt aggaagccgc ccaagggcga    2940
cgagcaacca gatttttcg ttccgatgct ctatgacgtg gcacccgcg atagtcgcag      3000 catcatggac gtggccgttt tccgtctgtc gaagcgtgac cgacgagctg gcgaggtgat    3060
ccgctacgag cttccagacg ggcacgtaga ggtttccgca gggccggccg gcatggccag    3120
tgtgtgggat tacgacctgg tactgatggc ggtttcccat ctaaccgaat ccatgaaccg    3180
ataccgggaa gggaagggag acaagcccgg ccgcgtgttc cgtccacacg ttgcggacgt    3240
actcaagttc tgccggcgag ccgatggcgg aaagcagaaa gacgacctgg tagaaacctg    3300
cattcggtta aacaccacgc acgttgccat gcagcgtacg aagaaggcca agaacggccg    3360
cctggtgacg gtatccgagg gtgaagcctt gattagccgc tacaagatcg taaagagcga    3420
```

```
aaccgggcgg ccggagtaca tcgagatcga gctagctgat tggatgtacc gcgagatcac   3480
agaaggcaag aacccggacg tgctgacggt tcaccccgat tacttttga tcgatcccgg    3540 catcggccgt tttctctacc gcctggcacg ccgcgccgca ggcaaggcag aagccagatg   3600
gttgttcaag acgatctacg aacgcagtgg cagcgccgga gagttcaaga agttctgttt   3660
caccgtgcgc aagctgatcg ggtcaaatga cctgccggag tacgatttga aggaggaggc   3720
ggggcaggct ggcccgatcc tagtcatgcg ctaccgcaac ctgatcgagg gcgaagcatc   3780
cgccggttcc taatgtacgg agcagatgct agggcaaatt gccctagcag gggaaaaagg   3840
tcgaaaaggt ctctttcctg tggatagcac gtacattggg aacccaaagc cgtacattgg   3900
gaaccggaac ccgtacattg ggaacccaaa gccgtacatt gggaaccggt cacacatgta   3960
agtgactgat ataaagaga aaaaggcga ttttccgcc taaaactctt taaaacttat     4020
taaaactctt aaaacccgcc tggcctgtgc ataactgtct ggccagcgca cagccgaaga   4080
gctgcaaaaa gcgcctaccc ttcggtcgct gcgctcccta cgcccgccg cttcgcgtcg    4140 gcctatcgcg gccgctggcc gctcaaaaat ggctggccta cggccaggca atctaccagg   4200
gcgcggacaa gccgcgccgt cgccactcga ccgccggcgc ccacatcaag gcaccctgcc   4260
tcgcgcgttt cggtgatgac ggtgaaaacc tctgacacat gcagctcccg gagacggtca   4320
cagcttgtct gtaagcggat gccgggagca gacaagcccg tcaggcgcg tcagcgggtg    4380 ttggcgggtg tcggggcgca gccatgaccc agtcacgtag cgatagcgga gtgtatactg   4440
gcttaactat gcggcatcag agcagattgt actgagagtg caccatatgc ggtgtgaaat   4500
accgcacaga tgcgtaagga gaaaataccg catcaggcgc tcttccgctt cctcgctcac   4560
tgactcgctg cgctcggtcg ttcggctgcg gcgagcggta tcagctcact caaaggcggt   4620
aatacggtta tccacagaat caggggataa cgcaggaaag aacatgtgag caaaaggcca   4680
gcaaaaggcc aggaaccgta aaaggccgc gttgctggcg ttttccata ggctccgccc     4740 ccctgacgag catcacaaaa atcgacgctc aagtcagagg tggcgaaacc cgacaggact   4800
ataaagatac caggcgtttc ccctggaag ctccctcgtg cgctctcctg ttccgaccct    4860
gccgcttacc ggatacctgt ccgcctttct cccttcggga agcgtggcgc tttctcatag   4920
ctcacgctgt aggtatctca gttcggtgta ggtcgttcgc tccaagctgg gctgtgtgca   4980
cgaacccccc gttcagcccg accgctgcgc cttatccggt aactatcgtc ttgagtccaa   5040
cccggtaaga cacgacttat cgccactggc agcagccact ggtaacagga ttagcagagc   5100
gaggtatgta ggcggtgcta cagagttctt gaagtggtgg cctaactacg gctacactag   5160
aaggacagta tttggtatct gcgctctgct gaagccagtt accttcggaa aaagagttgg   5220
tagctcttga tccggcaaac aaaccaccgc tggtagcggt ggtttttttg tttgcaagca   5280
gcagattacg cgcagaaaaa aaggatctca agaagatcct ttgatctttt ctacggggtc   5340
tgacgctcag tggaacgaaa actcacgtta agggattttg gtcatgcatt ctaggtacta   5400
aaacaattca tccagtaaaa tataatattt tattttctcc caatcaggct tgatccccag   5460
taagtcaaaa aatagctcga catactgttc ttccccgata tcctccctga tcgaccggac   5520
gcagaaggca atgtcatacc acttgtccgc cctgccgctt ctcccaagat caataaagcc   5580
acttactttg ccatctttca caaagatgtt gctgtctccc aggtcgccgt gggaaaagac   5640
aagttcctct tcgggctttt ccgtctttaa aaaatcatac agctcgcgcg gatctttaaa   5700
tggagtgtct tcttcccagt tttcgcaatc cacatcggcc agatcgttat tcagtaagta   5760
```

```
atccaattcg gctaagcggc tgtctaagct attcgtatag ggacaatccg atatgtcgat    5820
ggagtgaaag agcctgatgc actccgcata cagctcgata atcttttcag ggctttgttc    5880
atcttcatac tcttccgagc aaaggacgcc atcggcctca ctcatgagca gattgctcca    5940
gccatcatgc cgttcaaagt gcaggaccTT tggaacaggc agctttcctt ccagccatag    6000
catcatgtcc tttTccgtt ccacatcata ggtggtccct ttataccggc tgtccgtcat    6060
ttttaaatat aggttttcat tttctcccac cagcttatat accttagcag gagacattcc    6120
ttccgtatct tttacgcagc ggtattttc gatcagtttt ttcaattccg gtgatattct    6180
cattttagcc atttattatt tccttcctct tttctacagt atttaaagat accccaagaa    6240
gctaattata acaagacgaa ctccaattca ctgttccttg cattctaaaa ccttaaatac    6300
cagaaaacag ctttttcaaa gttgtttca aagttggcgt ataacatagt atcgacggag    6360
ccgattttga aaccgcggtg atcacaggca gcaacgctct gtcatcgtta caatcaacat    6420
gctaccctcc gcgagatcat ccgtgtttca aacccggcag cttagttgcc gttcttccga    6480
atagcatcgg taacatgagc aaagtctgcc gccttacaac ggctctcccg ctgacgccgt    6540
cccggactga tgggctgcct gtatcgagtg gtgattttgt gccgagctgc cggtcgggga    6600
gctgttggct ggctggtggc aggatatatt gtggtgtaaa caaattgacg cttagacaac    6660
ttaataacac attgcggacg tttttaatgt actgaattaa cgccgaatta attcggggga    6720
tctggatttt agtactggat tttggtttta ggaattagaa attttattga tagaagtatt    6780
ttacaaatac aaatacatac taagggtttc ttatatgctc aacacatgag cgaaaccCta    6840
taggaaccct aattccctta tctgggaact actcacacat tattatggag aaactcgagc    6900
ttgtcgatcg actctagcta gaggatcgat ccgaacccca gagtcccgct cagaagaact    6960
cgtcaagaag gcgatagaag gcgatgcgct gcgaatcggg agcggcgata ccgtaaagca    7020
cgaggaagcg gtcagcccat tcgccgccaa gctcttcagc aatatcacgg gtagccaacg    7080
ctatgtcctg atagcggtcc gccacaccca gccggccaca gtcgatgaat ccagaaaagc    7140
ggccattttc caccatgata ttcggcaagc aggcatcgca atgggtcacg acgagatcat    7200
cgccgtcggg catgcgcgcc ttgagcctgg cgaacagttc ggctggcgcg agccctgat    7260 gctcttcgtc cagatcatcc tgatcgacaa gaccggcttc catccgagta cgtgctcgct    7320
cgatgcgatg tttcgcttgg tggtcgaatg ggcaggtagc cggatcaagc gtatgcagcc    7380
gccgcattgc atcagccatg atggatactt tctcggcagg agcaaggtga gatgacagga    7440
gatcctgccc cggcacttcg cccaatagca gccagtccct tcccgcttca gtgacaacgt    7500
cgagcacagc tgcgcaagga acgcccgtcg tggccagcca cgatagccgc gctgcctcgt    7560
cctgcagttc attcagggca ccggacaggt cggtcttgac aaaaagaacc gggcgcccct    7620
gcgctgacag ccggaacacg gcggcatcag agcagccgat tgtctgttgt gcccagtcat    7680
agccgaatag cctctccacc caagcggccg gagaacctgc gtgcaatcca tcttgttcaa    7740
tcatgcgaaa cgatccagat ccggtgcaga ttatttggat tgagagtgaa tatgagactc    7800
taattggata ccgaggggaa tttatggaac gtcagtggag cattttTgac aagaaatatt    7860
tgctagctga tagtgacctt aggcgacttt tgaacgcgca ataatggttt ctgacgtatg    7920
tgcttagctc attaaactcc agaaacccgc ggctgagtgg ctccttcaat cgttgcggtt    7980
ctgtcagttc caaacgtaaa acggcttgtc ccgcgtcatc ggcgggggtc ataacgtgac    8040
tcccttaatt ctccgctcat gatcagattg tcgtttcccg ccttcagttt ccaagcttgg    8100
cactggccgt cgttttacaa cgtcgtgact gggaaaaccc tggcgttacc caacttaatc    8160
```

```
gccttgcagc acatccccct tcgccagct ggcgtaatag cgaagaggcc cgcaccgatc   8220
gcccttccca acagttgcgc agcctgaatg gcgaatgcta gagcagcttg agcttggatc   8280
agattgtcgt ttcccgcctt cagtttagct tcatggagtc aaagattcaa atagaggacc   8340
taacagaact cgccgtaaag actggcgaac agttcataca gagtctctta cgactcaatg   8400
acaagaagaa atcttcgtc aacatggtgg agcacgacac acttgtctac tccaaaaata   8460
tcaaagatac agtctcagaa gaccaaaggg caattgagac ttttcaacaa agggtaatat   8520
ccggaaacct cctcggattc cattgcccag ctatctgtca ctttattgtg aagatagtgg   8580
aaaaggaagg tggctcctac aaatgccatc attgcgataa aggaaaggcc atcgttgaag   8640
atgcctctgc cgacagtggt cccaaagatg gacccccacc cacgaggagc atcgtggaaa   8700
aagaagacgt tccaaccacg tcttcaaagc aagtggattg atgtgatatc tccactgacg   8760
taagggatga cgcacaatcc cactatcctt cgcaagaccc ttcctctata taggaagtt    8820
catttcattt ggagagaaca cgggggactc ttgaacatgt ctgatcagac cgataccacc   8880
cagaccactc ctgccgagaa ggctcctcca aaagaaatta tcaggggtag aatgcctatc   8940
gcagttgtag ctcttgcaag attcggctct cagtcaacta ccacaactaa ggctgcaggt   9000
aaatttctag ttttttctcct tcattttctt ggttaggacc cttttctctt tttattttttt 9060
tgagcttcga tctgttttta aactgatcta tttttaatt gattggttat ggtgtaaata   9120
ttacatagct ttaactgata atctgattac tttatttcgt gtgtaattga ttaattctgc   9180
agccgatgct cttggcacta cagttggtaa gattgatgac atcagaaaga acaggaactt   9240
cgcttacgtt acagcagatt tcaagcctac cgaagcccag aaggctgatg gcatcgagtg   9300
gcttaagaga catccagttg gtgctgatgc cttgattgaa gagcttcaga acctccctgt   9360
tgctactgcc gaagagtctg ctgcattcga gcaggttagg gcatcagcta gaggccagaa   9420
cgccaagact gctgagggag aagttgctca ggctggcggc ggaaatagaa ggaagaaaaa   9480
ggaaaagcct gccgaagctg gtgaggtgca gaaccctcca gcagctgatg gcgactctct   9540
tttgtcataa tctagactag t                                             9561
```

<210> SEQ ID NO 2
<211> LENGTH: 694
<212> TYPE: DNA
<213> ORGANISM: Artificial Sequence
<220> FEATURE:
<223> OTHER INFORMATION: Codon Optimized bombBC interrupted with
      catalase intron

<400> SEQUENCE: 2

```
atgtctgatc agaccgatac cacccagacc actcctgccg agaaggctcc tccaaaagaa    60
attatcaggg gtagaatgcc tatcgcagtt gtagctcttg caagattcgg ctctcagtca   120
actaccacaa ctaaggctgc aggtaaattt ctagtttttc tccttcattt tcttggttag   180
gacccttttc tcttttattt ttttgagct tcgatctgtt tttaaactga tctattttt   240
aattgattgg ttatggtgta aatattacat agctttaact gataatctga ttactttatt   300
tcgtgtgtaa ttgattaatt ctgcagccga tgctcttggc actacagttg gtaagattga   360
tgacatcaga aagaacagga acttcgctta cgttacagca gatttcaagc ctaccgaagc   420
ccagaaggct gatggcatcg agtggcttaa gagacatcca gttggtgctg atgccttgat   480
tgaagagctt cagaacctcc ctgttgctac tgccgaagag tctgctgcat tcgagcaggt   540
tagggcatca gctagaggcc agaacgccaa gactgctgag ggagaagttg ctcaggctgg   600
```

-continued cggcggaaat agaaggaaga aaaaggaaaa gcctgccgaa gctggtgagg tgcagaaccc    660
tccagcagct gatggcgact ctcttttgtc ataa    694

<210> SEQ ID NO 3
<211> LENGTH: 510
<212> TYPE: DNA
<213> ORGANISM: Artificial Sequence
<220> FEATURE:
<223> OTHER INFORMATION: Codon Optimized bombBC

<400> SEQUENCE: 3
atgtctgatc agaccgatac cacccagacc actcctgccg agaaggctcc tccaaaagaa     60
attatcaggg gtagaatgcc tatcgcagtt gtagctcttg caagattcgg ctctcagtca    120
actaccacaa ctaaggctgc agccgatgct cttggcacta cagttggtaa gattgatgac    180
atcagaaaga acaggaactt cgcttacgtt acagcagatt tcaagcctac cgaagcccag    240
aaggctgatg gcatcgagtg gcttaagaga catccagttg gtgctgatgc cttgattgaa    300
gagcttcaga acctccctgt tgctactgcc gaagagtctg ctgcattcga gcaggttagg    360
gcatcagcta gaggccagaa cgccaagact gctgagggag aagttgctca ggctggcggc    420
ggaaatagaa ggaagaaaaa ggaaaagcct gccgaagctg tgaggtgca gaaccctcca    480 gcagctgatg gcgactctct tttgtcataa    510

<210> SEQ ID NO 4
<211> LENGTH: 169
<212> TYPE: PRT
<213> ORGANISM: Artificial Sequence
<220> FEATURE:
<223> OTHER INFORMATION: mutant M3 predicted amino acid sequence

<400> SEQUENCE: 4

Met Ser Asp Gln Thr Asp Thr Thr Gln Thr Thr Pro Ala Glu Lys Ala
1               5                   10                  15

Pro Pro Lys Glu Ile Ile Arg Gly Arg Met Pro Ile Ala Val Val Ala
            20                  25                  30

Leu Ala Arg Phe Gly Ser Gln Ser Thr Thr Thr Thr Lys Ala Ala Ala
        35                  40                  45

Asp Ala Leu Gly Thr Thr Val Gly Lys Ile Asp Asp Ile Arg Lys Asn
    50                  55                  60

Arg Asn Phe Ala Tyr Val Thr Ala Asp Phe Lys Pro Thr Glu Ala Gln
65                  70                  75                  80

Lys Ala Asp Gly Ile Glu Trp Leu Lys Arg His Pro Val Gly Ala Asp
                85                  90                  95

Ala Leu Ile Glu Glu Leu Gln Asn Leu Pro Val Ala Thr Ala Glu Glu
            100                 105                 110

Ser Ala Ala Phe Glu Gln Val Arg Ala Ser Ala His Gly Gln Asn Ala
        115                 120                 125

Lys Thr Ala Glu Gly Glu Val Ala Gln Ala Gly Gly Gly Asn Arg Arg
    130                 135                 140

Lys Lys Lys Glu Lys Pro Ala Glu Ala Gly Glu Val Gln Asn Pro Pro
145                 150                 155                 160

Ala Ala Asp Gly Asp Ser Leu Leu Ser
                165

<210> SEQ ID NO 5
<211> LENGTH: 169

```
<212> TYPE: PRT
<213> ORGANISM: Artificial Sequence
<220> FEATURE:
<223> OTHER INFORMATION: mutant M4 predicted amino acid sequence

<400> SEQUENCE: 5

Met Ser Asp Gln Thr Asp Thr Thr Gln Thr Thr Pro Ala Glu Lys Ala
1               5                   10                  15

Pro Pro Lys Glu Ile Ile Arg Gly Arg Met Pro Ile Ala Val Val Ala
            20                  25                  30

Leu Ala Arg Phe Gly Ser Gln Ser Thr Thr Thr Lys Ala Ala Ala
        35                  40                  45

Asp Ala Leu Gly Thr Thr Val Gly Lys Ile Asp Asp Ile Arg Lys Asn
50                  55                  60

Arg Asn Phe Ala Tyr Val Thr Ala Asp Phe Lys Pro Thr Glu Ala Gln
65                  70                  75                  80

Lys Ala Asp Gly Ile Glu Trp Leu Lys His His Pro Val Gly Ala Asp
                85                  90                  95

Ala Leu Ile Glu Glu Leu Gln Asn Leu Pro Val Ala Thr Ala Glu Glu
            100                 105                 110

Ser Ala Ala Phe Glu Gln Val Arg Ala Ser Ala Arg Gly Gln Asn Ala
        115                 120                 125

Lys Thr Ala Glu Gly Glu Val Ala Gln Ala Gly Gly Asn Arg Arg
130                 135                 140

Lys Lys Lys Glu Lys Pro Ala Glu Ala Gly Glu Val Gln Asn Pro Pro
145                 150                 155                 160

Ala Ala Asp Gly Asp Ser Leu Leu Ser
                165

<210> SEQ ID NO 6
<211> LENGTH: 144
<212> TYPE: PRT
<213> ORGANISM: Artificial Sequence
<220> FEATURE:
<223> OTHER INFORMATION: mutant D1 predicted amino acid sequence

<400> SEQUENCE: 6

Met Pro Ile Ala Val Val Ala Leu Ala Arg Phe Gly Ser Gln Ser Thr
1               5                   10                  15

Thr Thr Thr Lys Ala Ala Ala Asp Ala Leu Gly Thr Thr Val Gly Lys
            20                  25                  30

Ile Asp Asp Ile Arg Lys Asn Arg Asn Phe Ala Tyr Val Thr Ala Asp
        35                  40                  45

Phe Lys Pro Thr Glu Ala Gln Lys Ala Asp Gly Ile Glu Trp Leu Lys
50                  55                  60

Arg His Pro Val Gly Ala Asp Ala Leu Ile Glu Leu Gln Asn Leu
65                  70                  75                  80

Pro Val Ala Thr Ala Glu Glu Ser Ala Ala Phe Glu Gln Val Arg Ala
                85                  90                  95

Ser Ala Arg Gly Gln Asn Ala Lys Thr Ala Glu Gly Glu Val Ala Gln
            100                 105                 110

Ala Gly Gly Gly Asn Arg Arg Lys Lys Lys Glu Lys Pro Ala Glu Ala
        115                 120                 125

Gly Glu Val Gln Asn Pro Pro Ala Ala Asp Gly Asp Ser Leu Leu Ser
130                 135                 140

<210> SEQ ID NO 7
```

<210> SEQ ID NO 7
<211> LENGTH: 94
<212> TYPE: PRT
<213> ORGANISM: Artificial Sequence
<220> FEATURE:
<223> OTHER INFORMATION: mutant D2 predicted amino acid sequence

<400> SEQUENCE: 7

```
Met Thr Glu Ala Gln Lys Ala Asp Gly Ile Glu Trp Leu Lys Arg His
1               5                   10                  15

Pro Val Gly Ala Asp Ala Leu Ile Glu Glu Leu Gln Asn Leu Pro Val
            20                  25                  30

Ala Thr Ala Glu Glu Ser Ala Ala Phe Glu Gln Val Arg Ala Ser Ala
        35                  40                  45

Arg Gly Gln Asn Ala Lys Thr Ala Glu Gly Val Ala Gln Ala Gly
    50                  55                  60

Gly Gly Asn Arg Arg Lys Lys Lys Glu Lys Pro Ala Glu Ala Gly Glu
65                  70                  75                  80

Val Gln Asn Pro Pro Ala Ala Asp Gly Asp Ser Leu Leu Ser
                85                  90
```

<210> SEQ ID NO 8
<211> LENGTH: 546
<212> TYPE: DNA
<213> ORGANISM: Pseudomonas aeruginosa

<400> SEQUENCE: 8

```
atggctttct ggctaccact attggccgct ggcggcatgt ccgcccttca acagggattg      60
gccaacaagg aagagcgcaa caagatcaag gccgagaaca aggctcgact gaagacggac     120
ctcgacaacc tgggcgccgc tgcccgcgat atcgccaacc tcggagtcat ggccgctagc     180
taccgcaagc aagccgtggc ctcgcaggtg gaggccaagc gccagggat gctagccggc      240
ggaagcgccg aggctcaggc cggggcgttc ggcgtcaagg gtgcatccgt cgatgcggtg     300
gccctggata tcgagcggga ggtcggcgag gccctgatcc agattgacga caacctggac     360
aatcagatgt ggaacctcgc cgagcaggcg cactccatcc aggctcaggc taaggccggc     420
ctgctgggtc agaagagtac cacgcgggg caacggtccc cgctggtggc cggtctgatg     480
tcggcgggtt ccctgtacgc aagtcaatac ttcaagttcg gcgccacgcc taaaggaggc     540
aactga                                                                546
```

<210> SEQ ID NO 9
<211> LENGTH: 181
<212> TYPE: PRT
<213> ORGANISM: Pseudomonas aeruginosa

<400> SEQUENCE: 9

```
Met Ala Phe Trp Leu Pro Leu Leu Ala Ala Gly Gly Met Ser Ala Leu
1               5                   10                  15

Gln Gln Gly Leu Ala Asn Lys Glu Glu Arg Asn Lys Ile Lys Ala Glu
            20                  25                  30

Asn Lys Ala Arg Leu Lys Thr Asp Leu Asp Asn Leu Gly Ala Ala Ala
        35                  40                  45

Arg Asp Ile Ala Asn Leu Gly Val Met Ala Ala Ser Tyr Arg Lys Gln
    50                  55                  60

Ala Val Ala Ser Gln Val Glu Ala Lys Arg Gln Gly Met Leu Ala Gly
65                  70                  75                  80

Gly Ser Ala Glu Ala Gln Ala Gly Ala Phe Gly Val Lys Gly Ala Ser
                85                  90                  95
```

```
Val Asp Ala Val Ala Leu Asp Ile Glu Arg Glu Val Gly Glu Ala Leu
            100                 105                 110
Ile Gln Ile Asp Asp Asn Leu Asp Asn Gln Met Trp Asn Leu Ala Glu
        115                 120                 125
Gln Ala His Ser Ile Gln Ala Gln Ala Lys Ala Gly Leu Leu Gly Gln
    130                 135                 140
Lys Ser Thr Thr Ala Gly Gln Arg Ser Pro Leu Val Ala Gly Leu Met
145                 150                 155                 160
Ser Ala Gly Ser Leu Tyr Ala Ser Gln Tyr Phe Lys Phe Gly Ala Thr
                165                 170                 175
Pro Lys Gly Gly Asn
            180
```

<210> SEQ ID NO 10
<211> LENGTH: 861
<212> TYPE: DNA
<213> ORGANISM: Ralstonia solanacearum

<400> SEQUENCE: 10

```
atgtggatgg cagcaatcgg cgcagtaatg agcatggcaa atgctcaggc ccagaaggag      60
gagcaggcgg cgcagcagta cgctcagaag acaatcgacc aagccaaagc cgatgccgcc     120
aacactgtga acgcagcgaa cgacgcaggt aagaatgcga ttcgcggcgc gaccaacgag     180
ttcgaggcgg cgcaggctgc cttgagcacg accacgcgct ccatcggcaa ccaacagaag     240
ctacgggcct acggcgagca gtacaacgcg ctccagacga gcatcatgcg ccagaatgac     300
atgatgatcc gaggccggct tacagaccag ctacaggccg cgtcgaatct cggagcactt     360
cgggccgacg ctgcggcgcg cggggttggc gggtcgagtg cggacatcat gcgctcagtc     420
gcggccctca acttcggcag caaggaaaca ctgcatcagg agcagcgggc caacatgtcg     480
tacgatcaag ctctgcaacg cgcaggcatg atccgcacgg cgatcctctc gcaagacctc     540
tcggtcgatc tcccgtcgct ggactacggc ttcagcagca cgccgcagca gacagcgggc     600
acgtacttcc aatcgagcaa cggtgtgaag caagcaatca tctcgggcct cccagcgcta     660
gcgcaagcag caggggcaat cgggagcgcg ttcacgggtg gcggggatac ctcgtccttc     720
tacaacgcag gagcaaagag cgcggctgac tacggcctga ccttcgggct gggcggttcg     780
agctatcaat caacggcagg cacgtcgtcg ctgacctacg ggtcgagcac tccgacctcg     840
ggcatgttca cttcagcata a                                               861
```

<210> SEQ ID NO 11
<211> LENGTH: 286
<212> TYPE: PRT
<213> ORGANISM: Ralstonia solanacearum

<400> SEQUENCE: 11

```
Met Trp Met Ala Ala Ile Gly Ala Val Met Ser Met Ala Asn Ala Gln
1               5                   10                  15

Ala Gln Lys Glu Glu Gln Ala Ala Gln Gln Tyr Ala Gln Lys Thr Ile
            20                  25                  30

Asp Gln Ala Lys Ala Asp Ala Ala Asn Thr Val Asn Ala Ala Asn Asp
        35                  40                  45

Ala Gly Lys Asn Ala Ile Arg Gly Ala Thr Asn Glu Phe Glu Ala Ala
    50                  55                  60

Gln Ala Ala Leu Ser Thr Thr Thr Arg Ser Ile Gly Asn Gln Gln Lys
65                  70                  75                  80
```

Leu Arg Ala Tyr Gly Glu Gln Tyr Asn Ala Leu Gln Thr Ser Ile Met
            85                  90                  95

Arg Gln Asn Asp Met Met Ile Arg Gly Arg Leu Thr Asp Gln Leu Gln
        100                 105                 110

Ala Ala Ser Asn Leu Gly Ala Leu Arg Ala Asp Ala Ala Arg Gly
        115                 120                 125

Val Gly Gly Ser Ser Ala Asp Ile Met Arg Ser Val Ala Ala Leu Asn
    130                 135                 140

Phe Gly Ser Lys Glu Thr Leu His Gln Glu Gln Arg Ala Asn Met Ser
145                 150                 155                 160

Tyr Asp Gln Ala Leu Gln Arg Ala Gly Met Ile Arg Thr Ala Ile Leu
                165                 170                 175

Ser Gln Asp Leu Ser Val Asp Leu Pro Ser Leu Asp Tyr Gly Phe Ser
            180                 185                 190

Ser Thr Pro Gln Gln Thr Ala Gly Thr Tyr Phe Gln Ser Ser Asn Gly
        195                 200                 205

Val Lys Gln Ala Ile Ile Ser Gly Leu Pro Ala Leu Ala Gln Ala Ala
    210                 215                 220

Gly Ala Ile Gly Ser Ala Phe Thr Gly Gly Asp Thr Ser Ser Phe
225                 230                 235                 240

Tyr Asn Ala Gly Ala Lys Ser Ala Ala Asp Tyr Gly Leu Thr Phe Gly
                245                 250                 255

Leu Gly Gly Ser Ser Tyr Gln Ser Thr Ala Gly Thr Ser Ser Leu Thr
            260                 265                 270

Tyr Gly Ser Ser Thr Pro Thr Ser Gly Met Phe Thr Ser Ala
        275                 280                 285

<210> SEQ ID NO 12
<211> LENGTH: 774
<212> TYPE: DNA
<213> ORGANISM: Xanthomonas campestris

<400> SEQUENCE: 12
atggtggtcg ttgcacaggg tacggtccca gccaaggtcc atccgcagct caccaacctc        60
accgcactct tcgcagacgc agtaggtctc ttcctcgatg tcagcgacaa ggtggcggac       120
ctcctcgttc gcttcgccga tgtagaagcg cagggtgccg aacttctcct tgatctggcg       180
cacctcgccg ttccagccag cgtcgtacat ccgacgcatg ccggtcagga tcagaccgtg       240
ccagccgcgt ccgacatact tcacggcgtt ctcgaaggtc agccagtcgc ccttgtggtc       300
aaccagcggg cgctccgggc ggcgcagctg aatccactcc tcgccctgcg actcgacgta       360
gaagccgttg cggaccagga cgccgaagga ggcgcggttg cccacgcgca cgcaggcgat       420
cagctcgcgg ttgaacagaa gctccagata ctgcttgagc gcttcggtca tgacgccctt       480
gcgggacatc gccgggtcga gccaatagcc tacttggtag acgtgaggag ctgggaagcc       540
ggtgctcttg acgctgatca gccccgcgac gataccgccg acggtgatga cgcgcatgcg       600
cagcgcttcg ttcgccacgt ggaacgcgac ggattcggga gtggcgtgct tcacccaagc       660
caggttcgac agcgcctcgc ggttcttgtc gatgattttg tagagggaag ccgcgtcgcc       720
cttgatgaca gggcgaatca tggtgaggtc ggagtagatc gtgttcatca gtaa            774

<210> SEQ ID NO 13
<211> LENGTH: 257
<212> TYPE: PRT
<213> ORGANISM: Xanthomonas campestris

<400> SEQUENCE: 13

```
Met Val Val Val Ala Gln Gly Thr Val Pro Ala Lys Val His Pro Gln
1               5                   10                  15
Leu Thr Asn Leu Thr Ala Leu Phe Ala Asp Ala Val Gly Leu Phe Leu
            20                  25                  30
Asp Val Ser Asp Lys Val Ala Asp Leu Leu Val Arg Phe Ala Asp Val
        35                  40                  45
Glu Ala Gln Gly Ala Glu Leu Leu Asp Leu Ala His Leu Ala Val
    50                  55                  60
Pro Ala Ser Val Val His Pro Thr His Ala Gly Gln Asp Gln Thr Val
65              70                  75                  80
Pro Ala Ala Ser Asp Ile Leu His Gly Val Leu Glu Gly Gln Pro Val
                85                  90                  95
Ala Leu Val Val Asn Gln Arg Ala Leu Arg Ala Ala Gln Leu Asn Pro
            100                 105                 110
Leu Leu Ala Leu Arg Leu Asp Val Glu Ala Val Ala Asp Gln Asp Ala
        115                 120                 125
Glu Gly Gly Ala Val Ala His Ala His Ala Gly Asp Gln Leu Ala Val
    130                 135                 140
Glu Gln Lys Leu Gln Ile Leu Leu Glu Arg Phe Gly His Asp Ala Leu
145             150                 155                 160
Ala Gly His Arg Arg Val Glu Pro Ile Ala Tyr Leu Val Asp Val Arg
                165                 170                 175
Ser Trp Glu Ala Gly Ala Leu Asp Ala Asp Gln Pro Arg Asp Asp Thr
            180                 185                 190
Ala Asp Gly Asp Asp Ala His Ala Gln Arg Phe Val Arg His Val Glu
        195                 200                 205
Arg Asp Gly Phe Gly Ser Gly Val Leu His Pro Ser Gln Val Arg Gln
    210                 215                 220
Arg Leu Ala Val Leu Val Asp Asp Phe Val Glu Gly Ser Arg Val Ala
225             230                 235                 240
Leu Asp Asp Arg Ala Asn His Gly Glu Val Gly Val Asp Arg Val His
                245                 250                 255
Gln
```

<210> SEQ ID NO 14
<211> LENGTH: 513
<212> TYPE: DNA
<213> ORGANISM: Xanthomonas campestris

<400> SEQUENCE: 14

```
atgccgaccg tagacgccac tcccggttcg atcacggcca acagctacgt tactgtagcc        60
gaggcaaaact cgtacttcga tggttcctac ggtcggcctc tttggacttc ggctagcgag      120
gatgaaaaag cctcgctagt gatctctgcc tccagatatc tggaccagat gatggcgtgg      180
atcggcgctc cgaccaatcc cgaacagtca atgtggtggc cttgcaaaaa tgcagttatt      240
gggggggatga cgctgagcca agtgtctatc cctgtaaaag ttaaaatagc ggtcttcgag      300
ctcgcatact tcatgctgga gagcggggct gcactgtcat cgcggatca aaccatcgac        360
agcgtgaagg tcggcacaat tcgagtcgaa ttcacgaaga actccacgga tgcgggcctg      420
cccactttcg tcgaggcgat gttgagcgga tttggttctc cggtcctgta tggatcgaat      480
gccgcaagaa gtattgactt ggtgagagca tga                                    513
```

<210> SEQ ID NO 15
<211> LENGTH: 170
<212> TYPE: PRT
<213> ORGANISM: Xanthomonas campestris

<400> SEQUENCE: 15

Met Pro Thr Val Asp Ala Thr Pro Gly Ser Ile Thr Ala Asn Ser Tyr
1               5                   10                  15

Val Thr Val Ala Glu Ala Asn Ser Tyr Phe Asp Gly Ser Tyr Gly Arg
            20                  25                  30

Pro Leu Trp Thr Ser Ala Ser Glu Asp Glu Lys Ala Ser Leu Val Ile
        35                  40                  45

Ser Ala Ser Arg Tyr Leu Asp Gln Met Met Ala Trp Ile Gly Ala Pro
    50                  55                  60

Thr Asn Pro Glu Gln Ser Met Trp Trp Pro Cys Lys Asn Ala Val Ile
65                  70                  75                  80

Gly Gly Met Thr Leu Ser Gln Val Ser Ile Pro Val Lys Val Lys Ile
                85                  90                  95

Ala Val Phe Glu Leu Ala Tyr Phe Met Leu Glu Ser Gly Ala Ala Leu
            100                 105                 110

Ser Phe Ala Asp Gln Thr Ile Asp Ser Val Lys Val Gly Thr Ile Arg
        115                 120                 125

Val Glu Phe Thr Lys Asn Ser Thr Asp Ala Gly Leu Pro Thr Phe Val
    130                 135                 140

Glu Ala Met Leu Ser Gly Phe Gly Ser Pro Val Leu Tyr Gly Ser Asn
145                 150                 155                 160

Ala Ala Arg Ser Ile Asp Leu Val Arg Ala
                165                 170

<210> SEQ ID NO 16
<211> LENGTH: 510
<212> TYPE: DNA
<213> ORGANISM: Xanthomonas campestris

<400> SEQUENCE: 16
atgtccgacc agaccgatac cacccagacc acgccggccg agaaggcgcc gcccaaggaa      60
atcatccgcg tcgtatgcc gatcgcagtg gtcgccctgg cccgcttcgg cagccagtcc     120
accaccacca ccaaggccgc agcggatgcc ctgggcacca ccgtcggcaa gatcgacgac     180
atccgcaaga accgcaactt cgcctacgtc accgccgact tcaagccgac cgaagcccag     240
aaggccgacg gcatcgagtg gctgaagcgt catccggtcg gtgcggatgc cctgatcgaa     300
gagctgcaga acctgccggt cgccaccgcc gaagagtcgg ccgcattcga gcaggtccgc     360
gcatcggctc gcggcagaa cgccaagacc gccgagggtg aagtcgctca ggccggcggt     420
ggcaatcgtc gcaagaagaa ggaaaagccg gccgaagccg gtgaagtgca gaacccgccg     480
gccgccgatg cgactcgct cctgagctaa                                      510

<210> SEQ ID NO 17
<211> LENGTH: 169
<212> TYPE: PRT
<213> ORGANISM: Xanthomonas campestris

<400> SEQUENCE: 17

Met Ser Asp Gln Thr Asp Thr Thr Gln Thr Thr Pro Ala Glu Lys Ala
1               5                   10                  15

Pro Pro Lys Glu Ile Ile Arg Gly Arg Met Pro Ile Ala Val Val Ala

```
                  20                  25                  30
Leu Ala Arg Phe Gly Ser Gln Ser Thr Thr Thr Thr Lys Ala Ala Ala
            35                  40                  45

Asp Ala Leu Gly Thr Thr Val Gly Lys Ile Asp Asp Ile Arg Lys Asn
    50                  55                  60

Arg Asn Phe Ala Tyr Val Thr Ala Asp Phe Lys Pro Thr Glu Ala Gln
65                  70                  75                  80

Lys Ala Asp Gly Ile Glu Trp Leu Lys Arg His Pro Val Gly Ala Asp
                85                  90                  95

Ala Leu Ile Glu Glu Leu Gln Asn Leu Pro Val Ala Thr Ala Glu Glu
            100                 105                 110

Ser Ala Ala Phe Glu Gln Val Arg Ala Ser Ala Arg Gly Gln Asn Ala
            115                 120                 125

Lys Thr Ala Glu Gly Glu Val Ala Gln Ala Gly Gly Gly Asn Arg Arg
            130                 135                 140

Lys Lys Lys Glu Lys Pro Ala Glu Ala Gly Glu Val Gln Asn Pro Pro
145                 150                 155                 160

Ala Ala Asp Gly Asp Ser Leu Leu Ser
                165

<210> SEQ ID NO 18
<211> LENGTH: 182
<212> TYPE: DNA
<213> ORGANISM: Unknown
<220> FEATURE:
<223> OTHER INFORMATION: catalase intron sequence

<400> SEQUENCE: 18
aaatttctag tttttctcct tcattttctt ggttaggacc cttttctctt tttattttt      60 tgagcttcga tctgttttta aactgatcta tttttaatt gattggttat ggtgtaaata    120
ttacatagct ttaactgata atctgattac tttatttcgt gtgtaattga ttaattctgc   180
ag                                                                  182
```